United States Patent
Fang et al.

(10) Patent No.: US 8,507,696 B2
(45) Date of Patent: Aug. 13, 2013

(54) INTERMEDIATES IN THE SYNTHESIS ZEARALENONE MACROLIDE ANALOGS

(75) Inventors: Francis G. Fang, Andover, MA (US);
Xiang Niu, Watertown, MA (US);
Matthew J. Schnaderbeck, Methuen, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 105 days.

(21) Appl. No.: 12/746,675

(22) PCT Filed: Dec. 8, 2008

(86) PCT No.: PCT/US2008/013512
§ 371 (c)(1),
(2), (4) Date: Nov. 8, 2010

(87) PCT Pub. No.: WO2009/075823
PCT Pub. Date: Jun. 18, 2009

(65) Prior Publication Data
US 2011/0046398 A1    Feb. 24, 2011

Related U.S. Application Data

(60) Provisional application No. 61/012,411, filed on Dec. 7, 2007, provisional application No. 61/012,408, filed on Dec. 7, 2007, provisional application No. 61/012,409, filed on Dec. 7, 2007, provisional application No. 61/080,048, filed on Jul. 11, 2008.

(51) Int. Cl.
*C07D 313/00* (2006.01)

(52) U.S. Cl.
USPC .................................................. 549/268

(58) Field of Classification Search
None
See application file for complete search history.

(56) References Cited

U.S. PATENT DOCUMENTS

| | | | |
|---|---|---|---|
| 7,799,827 B2 | 9/2010 | Boivin et al. | |
| 7,915,306 B2 | 3/2011 | Chiba et al. | |
| 2006/0247448 A1 | 11/2006 | Boivin et al. | |

FOREIGN PATENT DOCUMENTS

| | | |
|---|---|---|
| EP | 0606044 A1 | 7/1994 |
| WO | 9613259 | 5/1996 |
| WO | 0248135 | 6/2002 |
| WO | 0248136 | 6/2002 |
| WO | 03076424 | 9/2003 |
| WO | 2008021213 | 2/2008 |
| WO | 2009075823 | 6/2009 |

OTHER PUBLICATIONS

F. Zaragoza Dorwald, Side Reactions in Organic Synthesis; A Guide to Successful Synthesis Design, Wiley-VCH, Weinheim, Preface, p. IX (2005).*
Fuhrhop, J., & Penzlin, G., Organic Synthesis: Concepts, Methods, Starting Materials, VCH Verlagsgesellschaft MBH, Weinheim, p. 157 (1994).*
Waters, Aromatic interactions in model systems, 6 Curr. Op. Chem. Bio. 736-741 (2002).*
International Preliminary Report on Patentability issued by WIPO for PCT/US2008/013512 on Jun. 8, 2010.
International Preliminary Report on Patentability issued by WIPO for PCT/US2008/013498 on Jun. 8, 2010.
Agatsuma, S. et al., "Revised Structure and Stereochemistry of Hypothemycin," Chem. Phar. Bull., vol. 41, (2):373-375 (1993).
Takehana, K. et al., "A Radicicol-Related Macrocyclic Nonaketide Compound, Antibiotic LL-Z1640-2, Inhibits the NJK/p38 Pathways in Signal-Specific Manner," Biochemical and Biophysical Research Communications, vol. 257:19-23 (1999).
Selles, P et al., "Convergent Stereospecific Synthesis of LL-Z1640-2 (orC292), Hypothemycin and related macrolides. Part 2," Tetrahedron Letters, vol. 43:4627-4631 (2002).
Selles, P et al., "Convergent Stereospecific Synthesis of C292 (or LL-Z1640-2), and Hypothemycin. Part 1," Tetrahedron Letters, vol. 43:4621-4625 (2002).
Nishioka, T. et al., "Concise Enantioselective Synthesis of (+) -Aspicilin Based on Ruthenium Catalyzed Olefin Methathesis Reaction," Tetrahedron Letters, vol. 39:5597-5600 (1998).
Henry, N., et al., "Fast and Efficient Synthesis of the Complete LL-Z1640-2 Framework," Tetrahedron Letter, vol. 48:6088-6091 (2007).
Tatsuta, K. et al., "The First Total Synthesis of a Macrocycli Antiprotozoan, LL-Z1640-2," Chemistry Letters, 172 (2001).

* cited by examiner

*Primary Examiner* — Janet Andres
*Assistant Examiner* — Timothy R Rozof
(74) *Attorney, Agent, or Firm* — Lathrop & Gage LLP; Brian C. Trinque

(57) ABSTRACT

Disclosed herein are methods and intermediates useful in the preparation of macrolides, e.g., compounds of formula (IV), wherein $R_1$-$R_{12}$ are as defined herein.

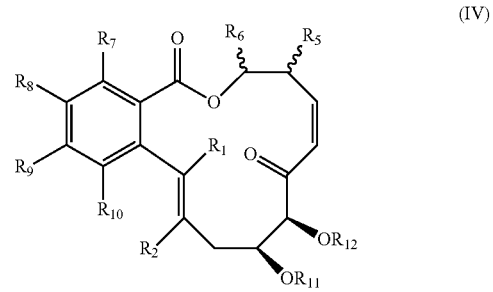

(IV)

18 Claims, 12 Drawing Sheets

Compound 002

Compound 011a

Compound 002

Compound 003

Compound 006

Compound 007

Compound 009

Compound 010

Compound 011

Compound 012

Compound 011a

Compound 009a

INTERMEDIATES IN THE SYNTHESIS ZEARALENONE MACROLIDE ANALOGS

RELATED APPLICATIONS

This application is a 35 U.S.C. §371 national stage filing of PCT Application No. PCT/US2008/013512 filed on Dec. 8, 2008, which claims priority to U.S. Provisional Application Ser. No. 61/012,411, filed on Dec. 7, 2007, U.S. Provisional Application Ser. No. 61/012,409, filed on Dec. 7, 2007, U.S. Provisional Application Ser. No. 61/012,408, filed on Dec. 7, 2007 and U.S. Provisional Application Ser. No. 61/080,048, filed on Jul. 11, 2008. The contents of the aforementioned applications are hereby incorporated by reference.

BACKGROUND OF THE INVENTION

Macrocyclic compounds, e.g., zearalenone-like macrolides such as F152 (LL-Z1640-2), have advantageous biological properties. For example, F152 and certain isomers

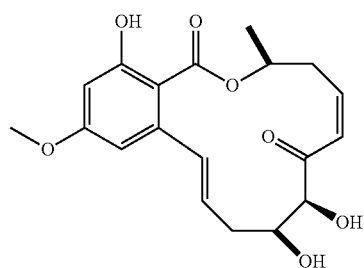

F152 thereof inhibit the phosphorylating enzyme Map/Erk kinase (MEK). Moreover, derivatives of F152 also have exhibited activity as tyrosine kinase inhibitors, inhibitors of other protein kinases, e.g., MEK1, inhibitors of NF-κB activation, and inhibitors AP-1 activation, to name a few. Often, however, F152 and derivatives thereof are obtained by fermentation techniques and modifications to the natural product and thus were limited in the number and types of derivatives that could be prepared and evaluated for biological activity.

Chemical synthesis of F152 and derivatives have also been disclosed (see, e.g., WO 03/076424), however, such syntheses are often complex and have many chromatographic purification steps in order to remove impurities.

BRIEF SUMMARY OF THE INVENTION

The present invention is based, at least in part, on the discovery of new methods and intermediates for the preparation of macrolides. Without wishing to be bound by any particular theory, it is believed that such intermediates may be useful, e.g., in providing purification points in the synthesis, thus decreasing or even removing the need for costly and time-consuming chromatographic steps up to that particular purification point. Without wishing to be bound by any particular theory, it is also believed that these new methods may be useful in providing compositions of macrolides having increased purity and increased yield in comparison with conventional methods.

Accordingly, in some embodiments, the present invention is directed to intermediates of formula (VII):

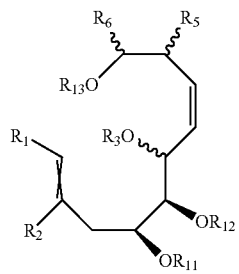

(VII)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_3$ is selected from the group consisting of hydrogen and a base stable oxygen protecting group;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

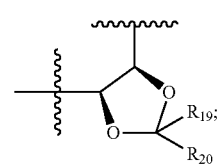

(a)

wherein $R_{19}$ and $R_{20}$ are each independently selected from the group consisting of hydrogen, $C_{1-6}$ alkyl, $C_{1-6}$ haloalkyl, $C_{1-6}$ alkoxy and phenyl, or $R_{19}$ and $R_{20}$ together represent a fluorenyl moiety of structure (b):

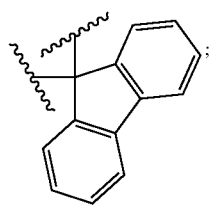

(b)

and R$_{13}$ is

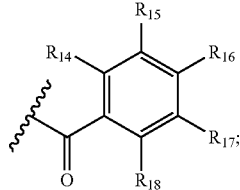

(VIII)

and
R$_{14}$, R$_{15}$, R$_{16}$, R$_{17}$, and R$_{18}$ are each independently selected from the group consisting of H, NO$_2$, —NH$_3^+$, —COH, —CO(C$_{1-4}$ alkyl), —COCl, —COOH, —COO(C$_{1-4}$ alkyl), —NR$_3^+$, —SO$_3$H, nitrile, —CF$_3$ and halogen.

In some embodiments, R$_3$ is a first aromatic ring-containing oxygen protecting group.

In other embodiments, the present invention is directed to intermediates of formula (VII):

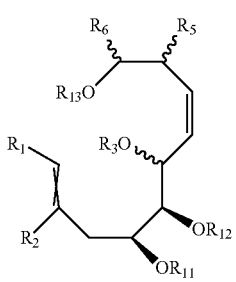

(VII)

wherein R$_1$ and R$_2$ are each independently selected from the group consisting of hydrogen, C$_{1-6}$ alkyl, C$_{3-6}$ unconjugated alkenyl and C$_{3-6}$ unconjugated alkynyl;
R$_3$ is a first aromatic ring-containing oxygen protecting group;
R$_5$ and R$_6$ are each independently selected from the group consisting of hydrogen, halogen, C$_{1-6}$ alkyl, C$_{2-6}$ alkenyl, C$_{2-6}$ alkynyl, C$_{1-6}$ haloalkyl, C$_{1-6}$ alkoxy, phenyl and benzyl, wherein the phenyl or benzyl are substituted with 0, 1, 2, or 3 substituents independently selected from halogen, hydroxyl, C$_{1-3}$ alkyl, and NH$_2$; or R$_5$ and R$_6$ are taken together with the carbons on which they are attached to form a 5-6 unconjugated membered carbocyclic ring;
R$_{11}$ and R$_{12}$ are each independently selected from the group consisting of hydrogen and a base stable oxygen protecting group; or R$_{11}$ and R$_{12}$ are taken together to form a 5 membered heterocyclyldiyl of structure (a):

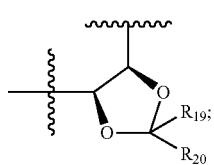

(a)

wherein R$_{19}$ and R$_{20}$ are each independently selected from the group consisting of hydrogen, C$_{1-6}$ alkyl, C$_{1-6}$ haloalkyl, C$_{1-6}$ alkoxy and phenyl, or R$_{19}$ and R$_{20}$ together represent a fluorenyl moiety of structure (b):

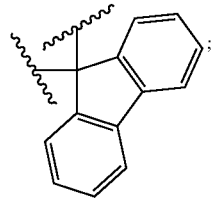

(b)

and
R$_{13}$ is a second aromatic ring-containing oxygen protecting group.

In some embodiments, R$_{13}$ is

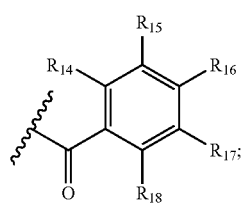

(VIII)

and
R$_{14}$, R$_{15}$, R$_{16}$, R$_{17}$, and R$_{18}$ are each independently selected from the group consisting of H, NO$_2$, —NH$_3^+$, —COH, —CO(C$_{1-4}$ alkyl), —COCl, —COOH, —COO(C$_{1-4}$ alkyl), —NR$_3^+$, —SO$_3$H, nitrile, —CF$_3$ and halogen.

In some embodiments, R$_1$ is hydrogen. In some embodiments, R$_2$ is hydrogen. In certain embodiments, R$_3$ is selected from benzoyl or benzyl, wherein the benzoyl or benzyl are each substituted with 0, 1, 2 or 3 substituents independently selected from —OH, —O(C$_{1-4}$alkyl), —NH$_2$, —NH(C$_{1-4}$alkyl), —N(C$_{1-4}$alkyl)$_2$, amides, —OCO(C$_{1-4}$ alkyl) and (C$_{1-4}$alkyl). In some embodiments, R$_3$ is 4-methoxybenzyl. In some embodiments, R$_5$ is selected from the group consisting of hydrogen and C$_{1-6}$ alkyl, e.g., hydrogen or methyl. In some embodiments, R$_6$ is selected from the group consisting of hydrogen and C$_{1-6}$ alkyl, e.g., hydrogen or methyl.

In some embodiments, the compound of formula (VII) is crystalline.

In some embodiments, one of R$_{14}$, R$_{15}$, R$_{16}$, R$_{17}$, and R$_{18}$ is selected from the group consisting of NO$_2$, —NH$_3^+$, —COH, —CO(C$_{1-4}$alkyl), —COCl, —COOH, —COO(C$_{1-4}$ alkyl), —NR$_3^+$, —SO$_3$H, nitrile, —CF$_3$ and halogen and the other four of R$_{14}$, R$_{15}$, R$_{16}$, R$_{17}$, and R$_{18}$ are hydrogen. In some embodiments, at least one of R$_{14}$, R$_{15}$, R$_{16}$, R$_{17}$, and R$_{18}$ is selected from the group consisting of NO$_2$, NH$_3^+$, —COH, —CO(C$_{1-4}$ alkyl), —COCl, —COOH, —COO(C$_{1-4}$ alkyl), —NR$_3^+$, —SO$_3$H, nitrile, —CF$_3$ and halogen and the other of R$_{14}$, R$_{15}$, R$_{16}$, R$_{17}$, and R$_{18}$ are hydrogen. In some embodiments, R$_{16}$ is NO$_2$ and each of R$_{14}$, R$_{15}$, R$_{17}$, and R$_{18}$ are independently hydrogen.

In some embodiments, the compound of formula (VII) is a compound of formula (VIIa):

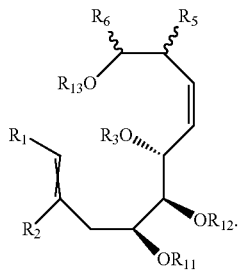

(VIIa)

In some embodiments, the compound of formula (VII) is a compound of formula (VIIb):

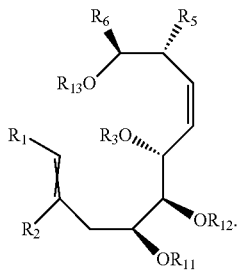

(VIIb)

In other embodiments, the present invention is directed to intermediates of formula (VIIc):

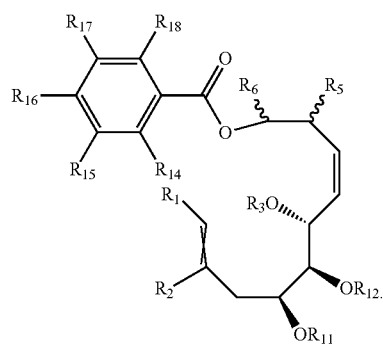

(VIIc)

wherein $R_1$ and $R_2$ are each independently selected from the group consisting of hydrogen and $C_{1-6}$ alkyl;

$R_3$ is selected from benzoyl or benzyl, wherein the benzoyl or benzyl are each substituted with 0, 1, 2 or 3 substituents independently selected from —OH, —O($C_{1-4}$alkyl), —NH$_2$, —NH($C_{1-4}$alkyl), —N($C_{1-4}$alkyl)$_2$, amides, —OCO($C_{1-4}$ alkyl) and ($C_{1-4}$alkyl);

$R_5$ and $R_6$ are each independently selected from the group consisting of hydrogen, halogen, $C_{1-6}$ alkyl, $C_{1-6}$ haloalkyl, and $C_{1-6}$ alkoxy;

$R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

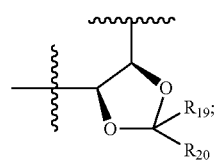

(a)

wherein $R_{19}$ and $R_{20}$ are each independently selected from the group
consisting of hydrogen, $C_{1-6}$ alkyl, $C_{1-6}$ haloalkyl and $C_{1-6}$ alkoxy; and at least one of $R_{14}$, $R_{15}$, $R_{16}$, $R_{17}$, and $R_{18}$ is selected from the group consisting of NO$_2$, —NH$_3^+$, —COH, —CO($C_{1-4}$ alkyl), —COCl, —COOH, —COO($C_{1-4}$ alkyl), —NR$_3^+$, —SO$_3$H, nitrile, —CF$_3$ and halogen and the remainder of $R_{14}$, $R_{15}$, $R_{16}$, $R_{17}$, and $R_{18}$ are each independently H.

In some embodiments, $R_1$ and $R_2$ are each independently hydrogen. In some embodiments, $R_3$ is 4-methoxybenzyl. In some embodiments, $R_5$ and $R_6$ are each independently hydrogen or methyl. In some embodiments, $R_{16}$ is NO$_2$ and each of $R_{14}$, $R_{15}$, $R_{17}$, and $R_{18}$ are independently hydrogen.

BRIEF DESCRIPTION OF THE DRAWINGS

FIG. 2 depicts single crystal X-rays of intermediates 002 and 011a.

DETAILED DESCRIPTION OF THE INVENTION

Figure 1:
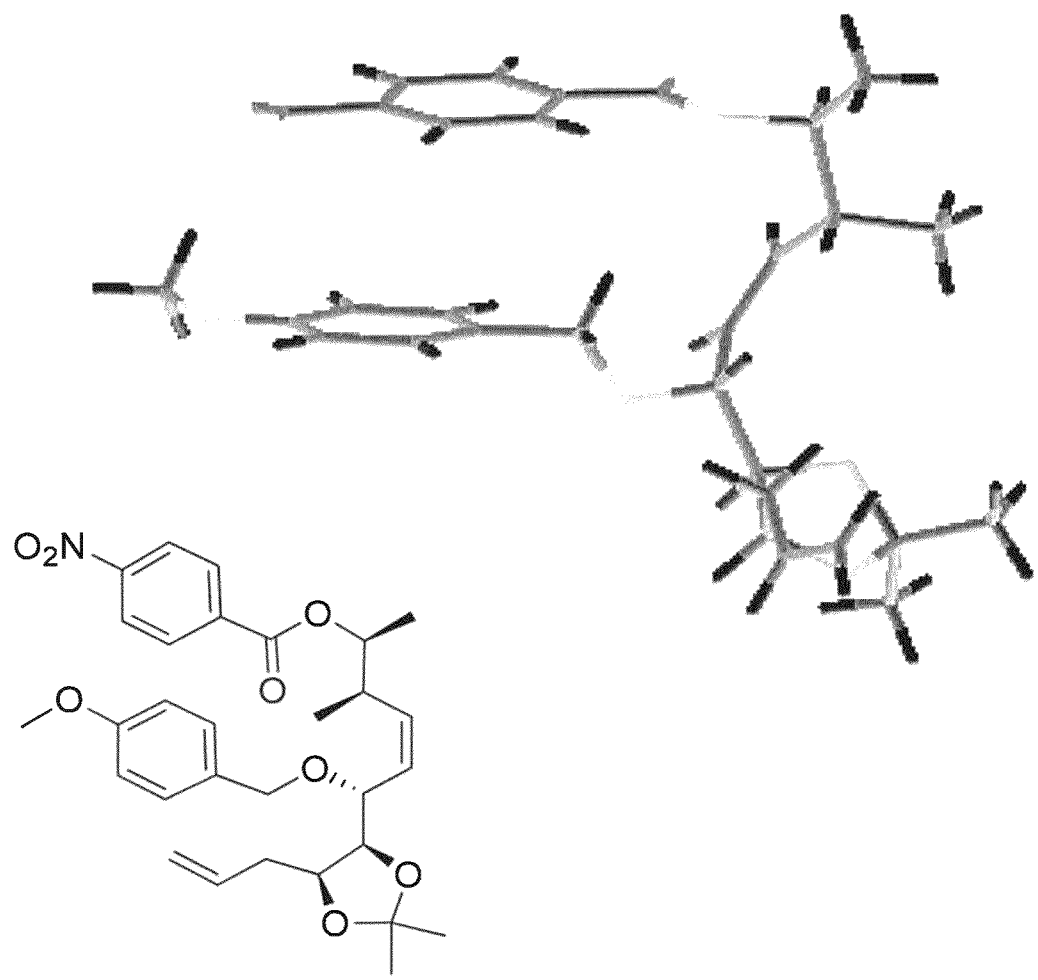
FIG. 1 is a single crystal X-ray of intermediate compound 011.

The present invention provides methods and intermediates for the preparation of macrolides, e.g., compounds of formula (IV)

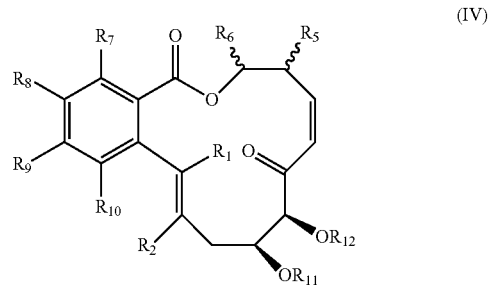

(IV)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and NH$_2$; or $R_5$ and $R_6$ are taken together with the carbons on which they are attached to form a 5-6 membered unconjugated carbocyclic ring;

$R_7$ is selected from the group consisting of hydrogen and —$OR_a$ wherein $R_a$ is hydrogen or a base stable oxygen protecting group;

$R_8$ is selected from the group consisting of hydrogen and —$OR_g$ wherein $R_g$ is hydrogen or a base stable oxygen protecting group;

$R_9$ is selected from the group consisting of hydrogen, halogen, —$OR_b$, $C_{1-6}$ alkyl, $C_{3-6}$ unconjugated alkenyl, $C_{3-6}$ unconjugated alkynyl, $C_{1-6}$ haloalkyl, —$SR_d$ and —$NR_eR_f$ wherein $R_b$ is hydrogen or a base stable oxygen protecting group, wherein $R_d$ is selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl and wherein $R_e$ and $R_f$ are each independently selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl or a base stable nitrogen protecting group; and $R_{10}$ is selected from the group consisting of hydrogen, halogen, —$OR_c$, $C_{1-6}$ alkyl, $C_{3-6}$ unconjugated alkenyl, $C_{3-6}$ unconjugated alkynyl, $C_{1-6}$ haloalkyl and $C_{1-6}$ alkoxy, wherein $R_c$ is hydrogen or a base stable oxygen protecting group; and $R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

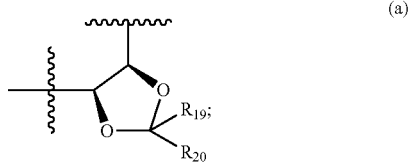

(a)

wherein $R_{19}$ and $R_{20}$ are each independently selected from the group consisting of hydrogen, $C_{1-6}$ alkyl, $C_{1-6}$ haloalkyl, $C_{1-6}$ alkoxy and phenyl, or $R_{19}$ and $R_{20}$ together represent a fluorenyl moiety of structure (b):

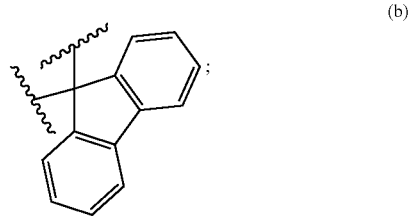 [SMILES: *C1(*)c2ccccc2-c2ccccc21]

(b)

and compositions comprising the same.

DEFINITIONS

In order to more clearly and concisely describe the subject matter of the claims, the following definitions are intended to provide guidance as to the meaning of specific terms used herein.

It is to be noted that the singular forms "a," "an," and "the" as used herein include "at least one" and "one or more" unless stated otherwise. Thus, for example, reference to "a pharmacologically acceptable carrier" includes mixtures of two or more carriers as well as a single carrier, and the like.

Numerous values and ranges are recited in connection with various embodiments of the present invention, e.g., amount of a compound of the invention present in a composition. It is to be understood that all values and ranges which fall between the values and ranges listed are intended to be encompassed by the present invention unless explicitly stated otherwise. Additionally, it is also to be understood that all numerical values listed herein are implicitly modified by the term "about" unless specifically stated otherwise. The term "about" as used herein in association with parameters, ranges and amounts, means that the parameter or amount is within ±1.0% of the stated parameter or amount.

As used herein, "alkyl" groups include saturated hydrocarbons having one or more carbon atoms, including straight-chain alkyl groups (e.g., methyl, ethyl, propyl, butyl, pentyl, hexyl, etc.), cyclic alkyl groups (or "cycloalkyl" or "alicyclic" or "carbocyclic" groups) (e.g., cyclopropyl, cyclopentyl, cyclohexyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). In certain embodiments, a straight-chain or branched-chain alkyl group may have 8 or fewer carbon atoms in its backbone, e.g., $C_1$-$C_8$ for straight-chain or $C_3$-$C_8$ for branched-chain. In certain embodiments, a straight-chain or branched-chain alkyl group may have 6 or fewer carbon atoms in its backbone, e.g., $C_1$-$C_6$ for straight-chain or $C_3$-$C_6$ for branched-chain. In still other embodiments, an alkyl group includes about 1 to 4 carbons. In other embodiments, an alkyl group includes about 1 to 3 carbons. In yet other embodiments, an alkyl group includes about 1 or 2 carbons. In some embodiments, preferred alkyl groups include $C_1$-$C_6$ alkyl groups. The terms "$C_1$-$C_6$" and "$C_{1-6}$" as in "$C_1$-$C_6$ alkyl" and "$C_{1-6}$ alkyl" are used interchangeably to mean alkyl groups containing 1 to 6 carbon atoms. The term "haloalkyl" means alkyl groups wherein one or more, e.g., 1 to 3, hydrogen atoms have been replaced with a halogen. The terms "alkenyl" and "alkynyl" refer to unsaturated aliphatic groups analogous to alkyls, but which contain at least one double or triple carbon-carbon bond respectively. In complex structures, carbon chains may be branched, bridged, or cross-linked. The terms "unconjugated alkenyl" and "unconjugated alkynyl" respectively refer alkenyl and alkynyl groups that are not conjugated with a portion of the core molecule.

The term "heteroalkyl group" includes straight-chain or branched-chain structures analogous to alkyl groups in which one or more of the carbon atoms in the chain is an element other than carbon, for example, nitrogen, sulfur, or oxygen. The term "heteroalkenyl group" includes straight-chain or branched-chain structures analogous to alkenyl groups in which one or more of the carbon atoms in the chain is an element other than carbon, for example, nitrogen, sulfur, or oxygen. The term "heteroalkynyl group" includes straight-chain or branched-chain structures analogous to alkynyl groups in which one or more of the carbon atoms in the chain is an element other than carbon, for example, nitrogen, sulfur, or oxygen. The term "$C_{1-6}$ heteroalkyl" and "$C_1$-$C_6$ heteroalkyl" are used interchangeably to refer to a moiety that has from 1-6 carbons and one or more heteroatoms.

The term "alkoxy" as used herein means an alkyl group having an oxygen atom attached thereto. In some embodiments, alkoxy groups include groups having 1 to about 8 carbon atoms. In other embodiments, alkoxy groups include groups having 1 to about 6 carbon atoms. In still other embodiments, alkoxy groups include groups having fewer than about 4 carbon atoms. In some embodiments, preferred alkoxy groups include $C_1$-$C_6$ alkoxy groups. Examples of alkoxy groups include, but are not limited to, methoxy, ethoxy, isopropyloxy, propoxy, butoxy, and pentoxy groups. The alkoxy groups can be straight-chain or branched.

The term "aromatic group" or "aryl group" includes unsaturated and aromatic cyclic hydrocarbons as well as unsaturated and aromatic heterocycles containing one or more rings. Aryl groups include, for example $C_{5-8}$ aryl groups. Aryl groups may also be fused or bridged with alicyclic or heterocyclic rings that are not aromatic so as to form a polycycle (e.g., tetralin).

The term "heterocyclic group" includes closed ring structures analogous to carbocyclic groups in which one or more, e.g., 1, 2 or 3, of the carbon atoms in the ring is an element other than carbon, for example, nitrogen, sulfur, or oxygen. Heterocyclic groups may be saturated or unsaturated. Additionally, heterocyclic groups (such as pyrrolyl, pyridyl, isoquinolyl, quinolyl, purinyl, and furyl) may or may not have aromatic character, in which case they may be referred to as "heteroaryl" or "heteroaromatic" groups. The term heterocyclic group includes rings which are attached to the core structure via either a bond to one of the heteroatoms in the ring or a bond to one of the carbons in the ring. Exemplary heterocyclic groups include, but are not e.g.,

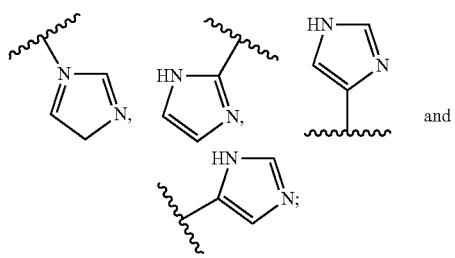

limited to imidazolyl,
morpholinyl, e.g.,

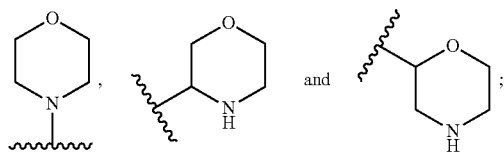 [SMILES: *N1CCOCC1 ; *C1COCCN1 ; *C1CNCCO1]

piperidinyl, e.g.,

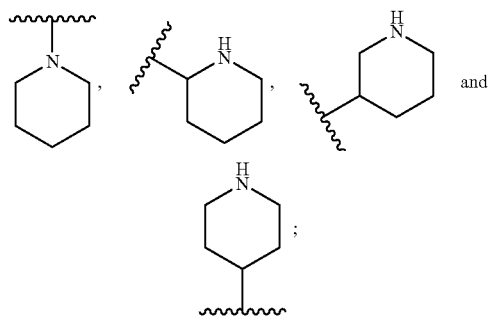

pyrrolidinyl, e.g., and

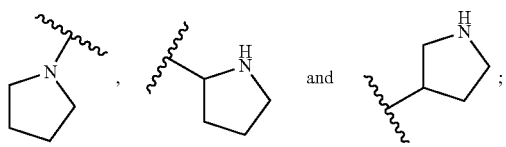 [SMILES: *N1CCCC1 ; *C1CCCN1 ; *C1CCNC1]

piperazinyl, e.g.;

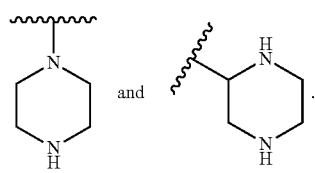 [SMILES: *N1CCNCC1 ; *C1CNCCN1]

The term "amine" or "amino," as used herein, refers to an unsubstituted or substituted moiety of the formula —$NR_xR_y$, in which $R_x$ and $R_y$ are each independently hydrogen, alkyl, aryl, or heterocyclyl, or $R_x$ and $R_y$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated.

The chemical moieties of the compounds of the invention, including those groups discussed above, may be "substituted or unsubstituted." In some embodiments, the term "substituted" means that the moiety has substituents placed on the moiety other than hydrogen (i.e., in most cases, replacing a hydrogen), which allow the molecule to perform its intended function. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, permissible substituents include acyclic and cyclic, branched and unbranched, carbocyclic and heterocyclic, aromatic and nonaromatic substituents of organic compounds. The compounds of the present invention may have one or more substitutions, as described herein.

When compounded chemical names, e.g., "alkylaryl," "aryloxy," and the like, are used herein, they are understood to have a specific connectivity to the core of the chemical structure. The moiety listed farthest to the right (e.g., aryl in "alkylaryl"), is the moiety which is directly connected to the core. Thus, an "arylalkyl" group, for example, is an alkyl group substituted with an aryl group (e.g., phenylmethyl (i.e., benzyl)). An "alkylaryl" moiety is an aryl group substituted with an alkyl group (e.g., p-methylphenyl (i.e., p-tolyl)).

The conventions

are used interchangeably to indicate a double bond having two substituents, where the substituents may be either cis or trans.

As used herein, the term "compound" is intended to mean a substance made up of molecules that further consist of atoms. A compound generally refers to a chemical entity, whether in the solid, liquid or gaseous phase, and whether in a crude mixture or purified and isolated. Compounds encompass the chemical compound itself as well as, where applicable: amorphous and crystalline forms of the compound, including polymorphic forms, said forms in mixture or in isolation; free acid and free base forms of the compound; isomers of the compound, including geometric isomers, optical isomers, and tautomeric isomers, said optical isomers to include enantiomers and diastereomers, chiral isomers and non-chiral isomers, said optical isomers to include isolated optical isomers or mixtures of optical isomers including racemic and non-racemic mixtures; said geometric isomers to include transoid and cisoid forms, where an isomer may be in isolated form or in admixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, including acid addition salts and base addition salts, including organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different.

The term "protecting group" as used herein, refers to a particular functional moiety, e.g., O, S, or N, being temporarily blocked so that a reaction can be carried out selectively at another reactive site in a multifunctional compound. In various embodiments, a protecting group reacts selectively in good yield to give a protected substrate that is stable to the projected reactions; is selectively removed in good yield by readily available, preferably nontoxic reagents that do not attack the other functional groups; forms an easily separable derivative (more preferably without the generation of new stereogenic centers); and has a minimum of additional functionality to avoid further sites of reaction. Compatibility of the protecting groups will typically take into consideration the reaction conditions in subsequent steps. Thus, if basic conditions are used, a protecting group readily cleavable by basic moieties may not be preferred. Similarly, if acidic conditions are used, a protecting group readily cleavable by acidic moieties may not be preferred. Protecting groups used in various embodiments of the present invention are described in more detail herein. Methods for removing protecting groups are well known in the art. For example, regarding typical oxygen protecting groups; acetyl groups can be removed under acidic conditions or basic conditions; methoxyethoxymethyl ether groups can be removed under acidic conditions; methoxymethyl ether groups can be removed under acidic conditions; methoxybenzyl ether groups can be removed under acidic conditions, by hydrogenolysis, or by oxidation; methylthiomethyl ether groups can be removed under acidic conditions; pivaloyl groups can be removed under acidic conditions, basic conditions or with reducing agents; tetrahydropyran groups can be removed under acidic conditions; silyl ether groups (including trimethylsilyl (TMS), tert-butyldimethylsilyl (TBDMS), and triisopropylsilyl (TIPS) ethers) can be removed under acidic conditions or with fluoride ion such as NaF or TBAF; and methyl ethers can be removed with TMSI in dichloromethane or MeCN or chloroform or $BBr_3$ in dichloromethane. In another example, regarding typical nitrogen protecting groups, carbobenzyloxy groups can be removed by hydrogenolysis; tert-Butyloxycarbonyl groups can be removed with concentrated, strong acid such as HCl or $CF_3COOH$; 9-Fluorenylmethyloxycarbonyl groups can be removed with base such as piperidine; benzyl groups can be removed by hydrogenolysis; and p-methoxyphenyl (PMP) group can be removed with ammonium cerium(IV) nitrate. As used herein, the term "base stable" protecting group refers to a protecting group that is stable under the basic conditions of any reaction of the compound which occurs subsequent to protection and prior to removal of the protecting group. Similarly, as used herein, the term "acid stable" protecting group refers to a protecting group that is stable under the acidic conditions of any reaction of the compound which occurs subsequent to protection and prior to removal of the protecting group. A skilled artisan would understand that a "base stable" protecting group is not necessarily stable to every base, (e.g., may not be stable to concentrated sodium hydroxide) but is stable to any bases utilised in any reaction of the compound which occurs subsequent to protection and prior to removal of the protecting group. Exemplary base stable protecting groups include, but are not limited to acetyl groups, methoxyethoxymethyl ether groups, methoxymethyl ether groups, methoxybenzyl ether groups, methylthiomethyl ether groups, pivaloyl groups, tetrahydropyran groups, silyl ether groups (including trimethylsilyl (TMS), tert-butyldimethylsilyl (TBDMS), and triisopropylsilyl (TIPS) ethers) and methyl ethers, carbobenzyloxy groups, tert-butyloxycarbonyl groups, benzyl groups and p-methoxyphenyl (PMP) groups. Similarly, a skilled artisan would understand that an "acid stable" protecting group is not necessarily stable to every acid, (e.g., may not be stable to concentrated hydrochloric acid) but is stable to any acids utilised in any reaction of the compound which occurs subsequent to protection and prior to removal of the protecting group.

The term "reacting," as used herein, refers to a chemical process or processes in which two or more reactants are allowed to come into contact with each other to effect a chemical change or transformation. For example, when reactant A and reactant B are allowed to come into contact with each other to afford one or more new chemical compound(s) C(C', C", etc.), A is said to have "reacted" with B to produce C.

The language "large scale" as used in the language "large scale preparation" includes reactions which result in product in an amount, e.g., greater than 26 g, e.g., greater than 30 g, e.g., greater than 35 g, e.g., greater than 40 g, e.g., greater than 45 g, e.g., greater than 50 g, e.g., greater than 60 g, e.g., greater than 70 g, e.g., greater than 80 g, e.g., greater than 90 g, e.g., greater than 100 g, e.g., greater than 200 g, e.g., greater than 500 g, e.g., greater than 1 kg, e.g., greater than 2 kg, e.g., greater than 5 kg, e.g., greater than 10 kg, e.g., greater than 20 kg, e.g., greater than 40 kg, e.g., greater than 60 kg, e.g., greater than 100 kg, e.g., greater than 300 kg e.g., greater than 500 kg.

The language "alpha-enhanced" is used in reference to the composition comprising the intermediates, e.g., compounds of formula (V) and/or (VI), which include a higher ratio of α isomer to β isomer than previously prepared compositions. The α and β isomers of formula (V) and (VI) are shown below.

Formula (V):

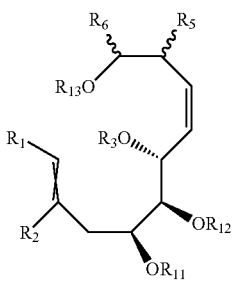
α isomer

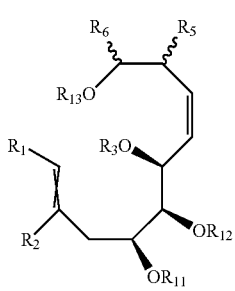
β isomer

Formula (VI):

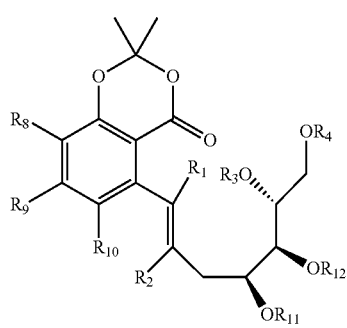
α isomer

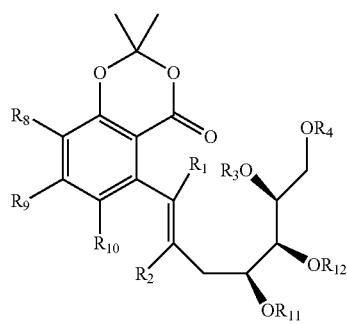
β isomer

Previously prepared compositions (see, e.g., U.S. Patent Application Publication No. 20060247448, published Nov. 2, 2006; paragraphs [1242]-[1248]) typically have a ratio of α isomer to β isomer of about 1:2. In some embodiments, the term "alpha-enhanced" refers compositions which include compounds of formula (V) and/or (VI) in an α to β ratio of at least about 1:1.5. In some embodiments, the term "alpha-enhanced" refers compositions which include compounds of formula (V) and/or (VI) in an α to β ratio of at least about 1:1, e.g., at least about 2:1, 3:1, 4:1, 5:1, 10:1, 25:1, 50:1, 100:1, 500:1, or 1000:1. In some embodiments, the term "alpha-enhanced" refers compositions which include compounds of formula (V) and/or (VI) having only the α isomer. It should be noted that alpha-enhanced compositions of the invention are not intended to be limited by scale of the reaction that produces the compounds. Similarly the language "alpha-intermediate" is used in reference to the intermediates, e.g., compounds of formula (V) and/or (VI), which represent the α isomer, as described in more detail herein.

The language "yield-enhanced" is used in reference to the composition comprising compounds of formula (IV) synthesized using alpha-enhanced intermediate compositions (see, e.g., U.S. Patent Application Publication No. 20060247448). These compositions have a higher yield of target compound (e.g., compounds of formula (IV)) in comparison with products synthesized using non-alpha-enhanced intermediate compositions. In some embodiments, the term "yield-enhanced" refers to at least 5% additional yield versus a non-alpha-enhanced composition. In some embodiments, the term "yield-enhanced" refers to at least 10%, 20%, 30%, 40%, 50%, 60%, 70%, 80%, 90%, 100% or 200% additional yield versus a non-alpha-enhanced composition. It should be noted that the percentages used in the context of percent yield is intended to describe percentages relative to the yield of the final product (i.e., weight by weight, w/w). It should also be noted that yield-enhanced compositions of the invention are not intended to be limited by scale of the reaction that produces the compounds.

The language "purity-enhanced" is used in reference to the composition comprising the final product, e.g., a composition comprising a compound of formula (IV) as the therapeutic agent, which is significantly free of impurities, e.g., impurities that are side-products of the reaction or residual starting material that would be considered unsuitable for administration to a subject, e.g., a human, or preferentially omitted by a skilled artisan from a pharmaceutical composition prepared for administration to a subject. In some embodiments, the term "purity-enhanced" refers to the purity of products synthesized using alpha-enhanced intermediate compositions versus products synthesized using intermediate compositions which are not alpha-enhanced (see, e.g., U.S. Patent Application Publication No. 20060247448). It should be noted that purity-enhanced compositions of the invention are not intended to be limited by scale of the reaction that produces the compounds.

The language "free of" is used herein, in reference to a composition of the present invention which is significantly, substantially or completely lacking a referenced item, for example, an impurity (such as p-anisaldehyde), which has been introduced into the reaction through the synthetic process. For example, in certain embodiments, the language "free of" is not intended to encompass impurities, for example, residual sodium, which has been introduced through environmental factors rather than through the synthetic process.

The language "significantly free of" as used in the language "significantly free of impurities" characterizes the presence of impurities, e.g., dimers, acetonide elimination products, compounds where an allylic methyl is eliminated, etc., in a final product, e.g., a composition comprising a compound of formula (IV) as the therapeutic agent, in an amount that is less than or equal to 10%, e.g., less than or equal to 9%, e.g., less than or equal to 8%, e.g., less than or equal to 7%, e.g., less than or equal to 6%, e.g., less than or equal to 5%, e.g., less than or equal to 4%, e.g., less than or equal to 3%, e.g., less than or equal to 2%, e.g., less than or equal to 1.5%, e.g., less than or equal to 1%, e.g., less than or equal to 0.5%, e.g., less than or equal to 0.4%, e.g., less than or equal to 0.3%, e.g., less than or equal to 0.2%, e.g., less than or equal to 0.175%, e.g., less than or equal to 0.15%, e.g., less than or equal to 0.125%, e.g., less than or equal to 0.1%, e.g., less than or equal to 0.75%, e.g., less than or equal to 0.5%, e.g., less than or equal to 0.25%, and e.g., 0%. In specific embodiments the purity-enhanced compositions of the present invention are significantly free of organic impurities, e.g., impurities composed, at least partially, of carbon atoms, e.g., p-anisaldehyde (or any other of possible intermediates or elimination products shown herein). The language "substantially free of as used in the language "substantially free of" impurities" characterizes the presence of impurities, e.g., dimers, acetonide elimination products, compounds where an allylic methyl is eliminated, etc., in a final product, e.g., a composition comprising a compound of formula (IV) as the therapeutic agent, in an amount that is less than or equal to 5%, e.g., less than or equal to 4%, e.g., less than or equal to 3%, e.g., less than or equal to 2%, e.g., less than or equal to 1.5%, e.g., less than or equal to 1%, e.g., less than or equal to 0.5%, e.g., less than or equal to 0.4%, e.g., less than or equal to 0.3%, e.g., less than or equal to 0.2%, e.g., less than or equal to 0.175%, e.g., less than or equal to 0.15%, e.g., less than or equal to 0.125%, e.g., less than or equal to 0.1%, e.g., less than or equal to 0.75%, e.g., less than or equal to 0.5%, e.g., less than or equal to 0.25%, and e.g., 0%. The language equal to 0.4%, e.g., less than or equal to 0.3%, e.g., less than or equal to 0.2%, e.g., less than or equal to 0.175%, e.g., less than or equal to 0.15%, e.g., less than or equal to 0.125%, e.g., less than or equal to 0.1%, e.g., less than or equal to 0.75%, e.g., less than or equal to 0.5%, e.g., less than or equal to 0.25%, and e.g., 0%. It should be noted that the percentages used in the context of percentage of impurities is intended to describe percentages relative to the weight of the final product, e.g., pharmaceutical composition (i.e., weight by weight, w/w). In some embodiments, the percent impurities are measured as area % impurity (e.g., by HPLC).

Methods of the Invention

The present invention is directed, at least in part, to novel methods for synthesizing macrolides. In some embodiments, the present invention is directed to large scale preparation of macrolides. Schemes 1 and 2 depict exemplary methods for synthesizing macrolides of the present invention. Scheme 1 is a schematic showing the protection and ring opening of a ribose molecule, followed by coupling to a triphenylphosphonium salt, coupling to a bicyclic triflate and ring closing to form the macrolide.

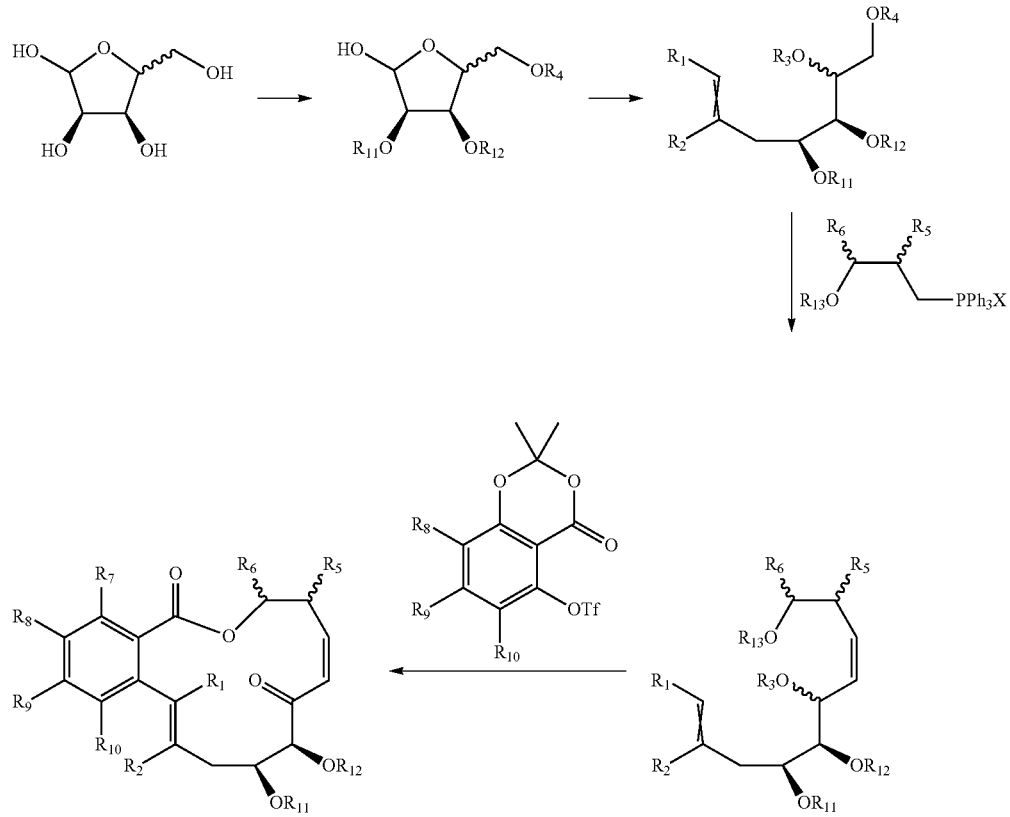

Scheme 1: Synthesis of formula (IV) from ribose-route 1

"substantially pure" as used herein, also refers to the presence of impurities of less than or equal to 5%, e.g., less than or equal to 4%, e.g., less than or equal to 3%, e.g., less than or equal to 2%, e.g., less than or equal to 1.5%, e.g., less than or equal to 1%, e.g., less than or equal to 0.5%, e.g., less than or Additionally, the same building blocks may be employed as in Scheme 2, which is a schematic showing the protection and ring opening of a ribose molecule, followed by coupling to a bicyclic triflate, coupling to a triphenylphosphonium salt and ring closing to form the macrolide.

Scheme 2: Synthesis of formula (IV) from ribose-route 2

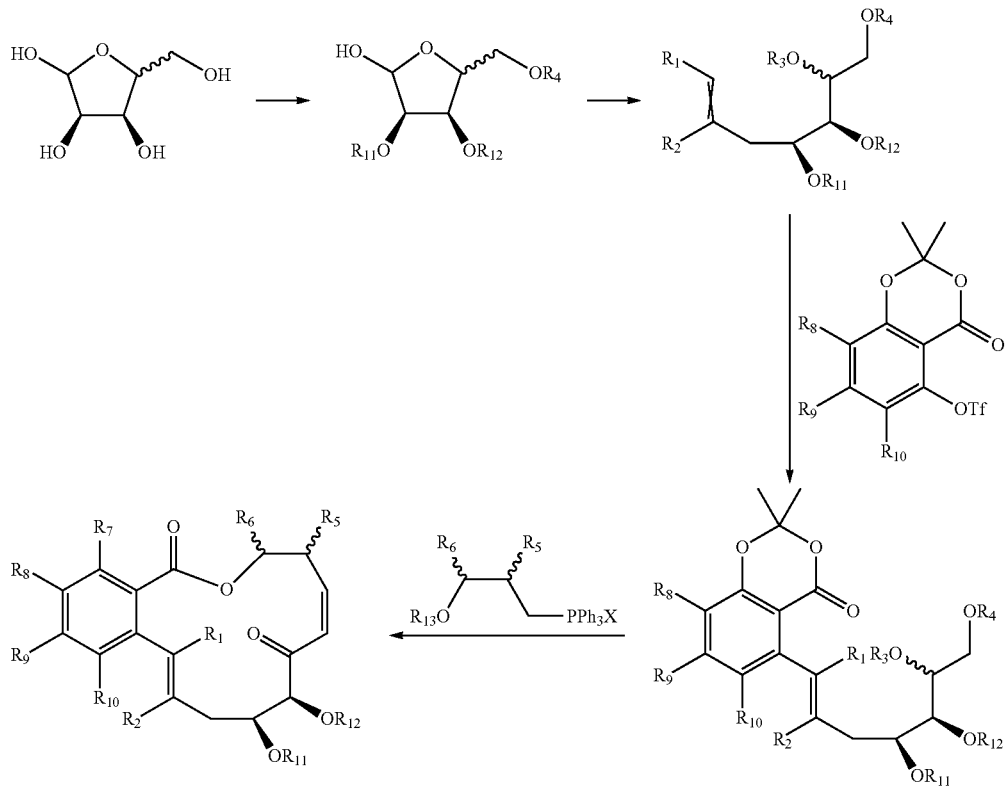

Accordingly, in some aspects, the present invention is directed to methods for making a compound of formula (V):

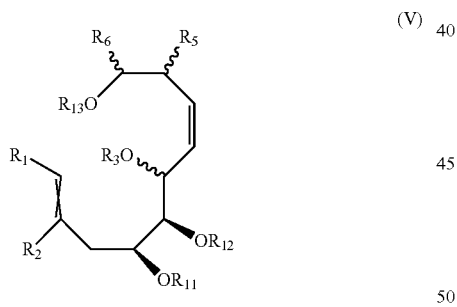

(V)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_3$ is selected from the group consisting of hydrogen and a base stable oxygen protecting group;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

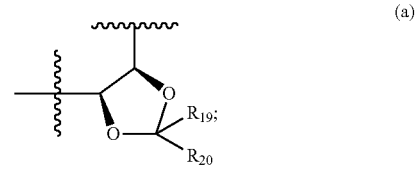

(a)

wherein $R_{19}$ and $R_{20}$ are each independently selected from the group consisting of hydrogen, $C_{1-6}$ alkyl, $C_{1-6}$ haloalkyl, $C_{1-6}$ alkoxy and phenyl, or $R_{19}$ and $R_{20}$ together represent a fluorenyl moiety of structure (b):

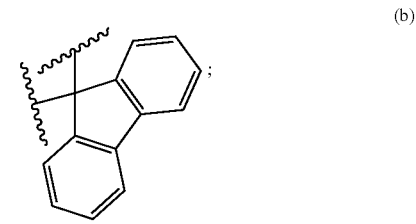 [SMILES: *C1(*)c2ccccc2-c2ccccc21]

(b)

and $R_{13}$ is selected from the group consisting of hydrogen and a base stable oxygen protecting group.

Compounds of formula (V) are synthesized by reacting a compound of formula I:

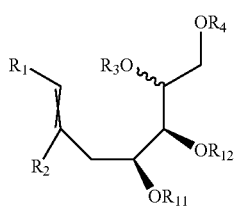

(I)

wherein $R_4$ is selected from the group consisting of hydrogen and a base stable oxygen protecting group;
with a compound of formula (II):

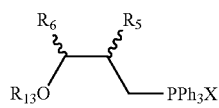

(II)

wherein X is a halogen; under suitable conditions, such that a compound of formula (V) is formed.

In some embodiments, suitable conditions for forming a compound of formula (V) are suitable basic conditions. In some embodiments, suitable conditions for forming a compound of formula (V) include the use of a base, e.g., a $C_{1-6}$ alkyl lithium, a potassium $C_{1-6}$ t-alkoxide, sodium hydroxide, sodium hydride, ammonia, dimethylsulfoxide sodium salt and sodium hexamethyldisilylamide. In some embodiments, suitable conditions for forming a compound of formula (V) include the use of a $C_{1-6}$ alkyl lithium base such as butyl lithium.

The compounds of formula (I) and formula (II) can have varying stereochemistries at each chiral carbon. In preferred embodiments, the compounds of formula (I) and formula (II) have a specific stereochemistry at each chiral carbon. Accordingly, the resulting compound of formula (V) can have varying stereochemistries at each chiral carbon. For example, in some embodiments, the compound of formula (V) is a compound of formula (Va):

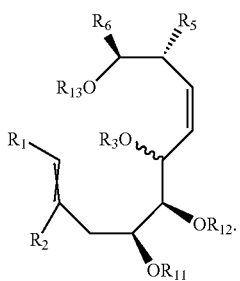

(Va)

That is, the compound of formula (II) can be a compound of formula (IIa):

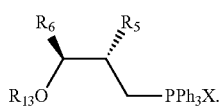

(IIa)

In some embodiments, the compound of formula (V) is a compound of (Vb):

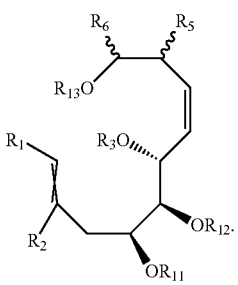

(Vb)

That is, the compound of formula (I) can be a compound of formula (Ib):

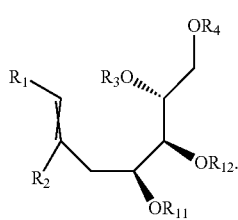

(Ib)

In some embodiments, the compound of formula (V) is a compound of (Vc):

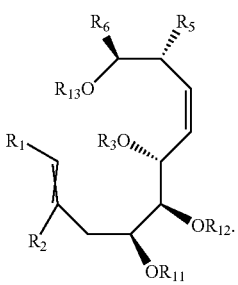

(Vc)

Suitable protecting groups vary depending on the nature of the reactions taking place, e.g., the suitable conditions for producing a compound of formula (V). In some embodiments, suitable oxygen protecting groups for $R_3$ include acetate groups, ester groups, benzyl groups and benzoate groups. In some embodiments, suitable oxygen protecting groups for $R_4$ include silyl groups. In some embodiments, suitable oxygen protecting groups for $R_{13}$ include silyl groups. In some embodiments, the protection of oxygen by $R_{13}$ results in a predominantly cis-olefin product, whereas if $R_{13}$ is a hydrogen, a predominantly trans olefin is formed. In some embodiments, the cis olefin is preferred.

In some embodiments, the double bond represented by

represents a double bond where the substituents are situated in a cis position, relative to each other.

In some aspects, the present invention is directed to methods for making a compound of formula (VI):

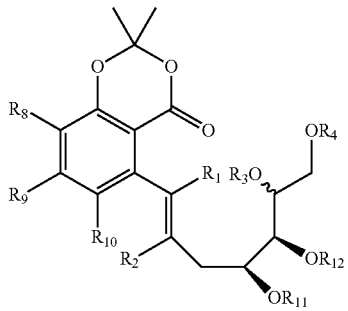

(VI)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_3$ is selected from the group consisting of hydrogen and a base stable oxygen protecting group;

$R_4$ is selected from the group consisting of hydrogen and a base stable oxygen protecting group;

$R_8$ is selected from the group consisting of hydrogen and —$OR_g$ wherein $R_g$ is hydrogen or a base stable oxygen protecting group, $R_9$ is selected from the group consisting of hydrogen, halogen, —$OR_b$, $C_{1-6}$ alkyl, $C_{3-6}$ unconjugated alkenyl, $C_{3-6}$ unconjugated alkynyl, $C_{1-6}$ haloalkyl, —$SR_d$ and —$NR_eR_f$ wherein $R_b$ is hydrogen or a base stable oxygen protecting group, wherein $R_d$ is selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl and wherein $R_e$ and $R_f$ are each independently selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl or a base stable nitrogen protecting group; and $R_{10}$ is selected from the group consisting of hydrogen, halogen, —$OR_c$, $C_{1-6}$ alkyl, $C_{3-6}$ unconjugated alkenyl, $C_{3-6}$ unconjugated alkynyl, $C_{1-6}$ haloalkyl and $C_{1-6}$ alkoxy, wherein $R_c$ is hydrogen or a base stable oxygen protecting group; and $R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

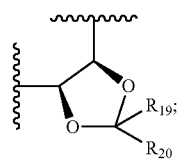

(a)

wherein $R_{19}$ and $R_{20}$ are each independently selected from the group consisting of hydrogen, $C_{1-6}$ alkyl, $C_{1-6}$ haloalkyl, $C_{1-6}$ alkoxy and phenyl, or $R_{19}$ and $R_{20}$ together represent a fluorenyl moiety of structure (b):

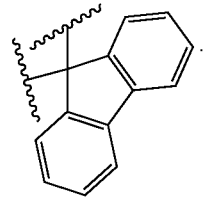

(b)

In some embodiments, suitable conditions for forming a compound of formula (VI) are suitable basic conditions. In some embodiments, suitable conditions for forming a compound of formula (V) include the use of a palladium catalyst. Palladium catalysts can be used in organic chemistry to facilitate carbon-carbon bond formation, e.g., by coordinating to a double bond of one fragment to form a pi-coordinated complex. Exemplary palladium catalysts include, but are not limited to tetrakis(triphenylphosphine)palladium(0), palladium chloride and palladium(II) acetate. In some embodiments, suitable conditions for forming a compound of formula (V) include Heck coupling conditions. In some embodiments suitable Heck coupling conditions include, but are not limited to the reaction of an unsaturated halide or triflate with an alkene and a strong base and palladium catalyst to form a substituted alkene.

Compounds of formula (VI) are synthesized by reacting a compound of formula (I):

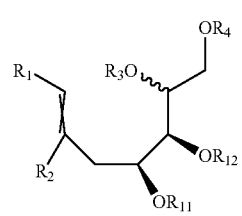

(I)

with a compound of formula (III):

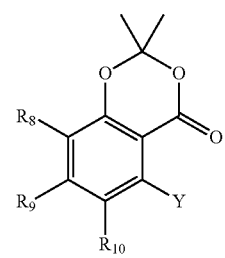

(III)

wherein Y is a halogen or a triflate (—O—$SO_2CF_3$) under suitable conditions, such that a compound of formula (VI) is formed.

The compounds of formula (I) and formula (III) can have varying stereochemistries at each chiral carbon. In preferred embodiments, the compounds of formula (I) and formula (III) have a specific stereochemistry at each chiral carbon. Accordingly, the resulting compound of formula (VI) can have varying stereochemistries at each chiral carbon. For example, in some embodiments, the compound of formula (VI) is a compound of formula (VIb):

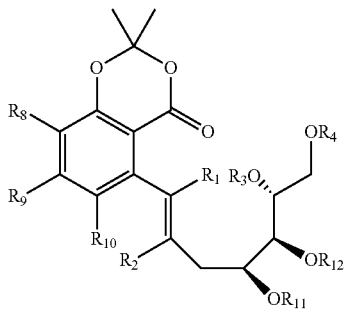

(VIb)

That is, the compound of formula (I) can be a compound of formula (Ib):

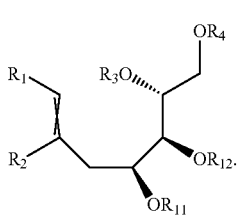

(Ib)

Suitable protecting groups vary depending on the nature of the reactions taking place, e.g., the suitable conditions for producing a compound of formula (VI). In some embodiments, suitable oxygen protecting groups for $R_3$ include acetate groups, ester groups, benzyl groups and benzoate groups. In some embodiments, suitable oxygen protecting groups for $R_4$ include silyl groups. Suitable protecting groups (oxygen and/or nitrogen) for the substituents of $R_8$, $R_9$ and $R_{10}$ (i.e., $R_b$—$R_g$) will be dependent upon the resulting substituent. For example, under the suitable basic conditions of the reaction to produce a compound of formula (VI) wherein $R_9$ is —$NR_eR_f$, $R_e$ and $R_f$ can each independently be a suitably base stable nitrogen protecting group, e.g., BOC. Similarly, under the suitable basic conditions of the reaction to produce a compound of formula (VI) wherein $R_9$ is —$OR_b$, $R_b$, can be a suitably base stable oxygen protecting group. In some embodiments, suitable oxygen protecting groups for $R_{13}$ include silyl groups.

In some embodiments, the double bond represented by

represents a double bond where the substituents are situated in a cis position, relative to each other.

In some aspects, the present invention is directed to methods for making a compound of formula (IV):

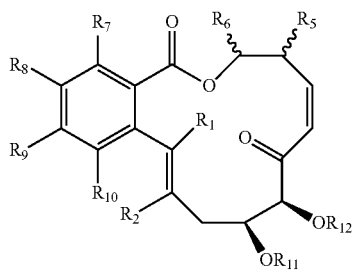

(IV)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_7$ is selected from the group consisting of hydrogen and —$OR_a$ wherein $R_a$ is hydrogen or a base stable oxygen protecting group;

$R_8$ is selected from the group consisting of hydrogen and —$OR_g$ wherein $R_g$ is hydrogen or a base stable oxygen protecting group;

$R_9$ is selected from the group consisting of hydrogen, halogen, —$OR_b$, $C_{1-6}$ alkyl, $C_{3-6}$ unconjugated alkenyl, $C_{3-6}$ unconjugated alkynyl, $C_{1-6}$ haloalkyl, —$SR_d$ and —$NR_eR_f$ wherein $R_b$ is hydrogen or a base stable oxygen protecting group, wherein $R_d$ is selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl and wherein $R_e$ and $R_f$ are each independently selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl or a base stable nitrogen protecting group; and $R_{10}$ is selected from the group consisting of hydrogen, halogen, —$OR_c$, $C_{1-6}$ alkyl, $C_{3-6}$ unconjugated alkenyl, $C_{3-6}$ unconjugated alkynyl, $C_{1-6}$ haloalkyl and $C_{1-6}$ alkoxy, wherein $R_c$ is hydrogen or a base stable oxygen protecting group; and $R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

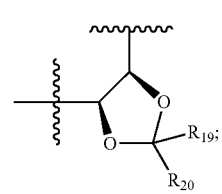

(a)

wherein $R_{19}$ and $R_{20}$ are each independently selected from the group consisting of hydrogen, $C_{1-6}$ alkyl, $C_{1-6}$ haloalkyl, $C_{1-6}$ alkoxy and phenyl, or $R_{19}$ and $R_{20}$ together represent a fluorenyl moiety of structure (b):

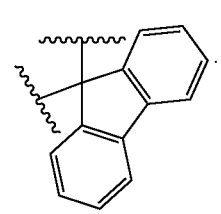

(b)

Compounds of formula (IV) are synthesized by combining a compound of formula (I) with a compound of formula (II) or a compound of formula (III) under suitable conditions, such that a compound of formula (IV) is formed. Compounds of formula (I), formula (II) and formula (III) are those listed above, in relation to the synthesis of compounds of formula (V) and formula (VI). In some embodiments, compounds of formula (IV) are synthesized by combining a compound of formula (I) with a compound of formula (II) or a compound of formula (III) under suitable conditions, such that an alpha-intermediate and a compound of formula (IV) are formed. In some embodiments, the alpha-intermediate is a compound of formula (V). In other embodiments, the alpha-intermediate is a compound of formula (VI).

In some embodiments, the synthesis of compounds of formula (IV) is not limited by inclusion of all three specific starting compounds (i.e., compounds of formula (I), formula (II) and formula (III)). That is, as long as compound (I) is reacted with either compound (II) or compound (III), the remainder of the synthesis may proceed via a route that does not specifically include the third compound. Accordingly, in some embodiments, the compound of formula (I) is reacted with the compound of formula (II) to form a compound of formula (V), which is subsequently used in the synthesis of a compound of formula (IV). In other embodiments, the compound of formula (I) is reacted with the compound of formula (III) to form a compound of formula (VI), which is subsequently used in the synthesis of a compound of formula (IV).

In some embodiments, the synthesis of compounds of formula (IV) is limited by inclusion of all three specific starting compounds (i.e., compounds of formula (I), formula (II) and formula (III)). That is, in some embodiments, the present invention includes a method for making a compound of formula (IV) comprising combining a compound of formula (I) with a compound of formula (II) and a compound of formula (III), under suitable conditions, such that a compound of formula (IV) is formed. Accordingly, in some embodiments, the compound of formula (I) is reacted with the compound of formula (II) to form a compound of formula (V), which is subsequently reacted with the compound of formula (III). In other embodiments, the compound of formula (I) is reacted with the compound of formula (III) to form a compound of formula (VI), which is subsequently reacted with the compound of formula (II).

Suitable protecting groups vary depending on the nature of the reactions taking place, e.g., the suitable conditions for producing a compound of formula (IV). In some embodiments, suitable oxygen protecting groups for $R_3$ include acetate groups, ester groups, benzyl groups and benzoate groups. In some embodiments, suitable oxygen protecting groups for $R_4$ include silyl groups. Again, suitable protecting groups (oxygen and/or nitrogen) for the substituents of $R_8$, $R_9$ and $R_{10}$ (i.e., $R_b$—$R_g$) will be dependent upon the resulting substituent. For example, under the suitable basic conditions of the reaction to produce a compound of formula (VI) wherein $R_9$ is —$NR_eR_f$, $R_e$ and $R_f$ can each independently be a suitably base stable nitrogen protecting group, e.g., BOC. Similarly, under the suitable basic conditions of the reaction to produce a compound of formula (VI) wherein $R_9$ is —$OR_b$, $R_b$ can be a suitably base stable oxygen protecting group. In some embodiments, suitable oxygen protecting groups for $R_{13}$ include silyl groups and/or ester groups or allylic groups.

As with the synthesis of compounds of formula (V) and formula (VI), the compounds of formula (I), formula (II) and formula (III) can have varying stereochemistries at each chiral carbon. In preferred embodiments, the compounds of formula (I), formula (II) and formula (III) have a specific stereochemistry at each chiral carbon. Accordingly, the resulting compound of formula (IV) can have varying stereochemistries at each chiral carbon. For example, in some embodiments, the compound of formula (IV) is a compound of formula (IVa):

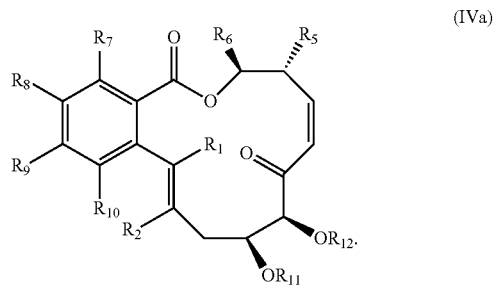

(IVa)

That is, the compound of formula (II) can be a compound of formula (IIa), as described above.

The various substituents on each of formulae (I)-(VI) can be present in any combination. In some embodiments, $R_1$ is hydrogen. In some embodiments, $R_2$ is hydrogen. In some embodiments, $R_1$ and $R_2$ are both hydrogen. In some embodiments, $R_5$ is hydrogen or a $C_{1-6}$ alkyl. In some embodiments, $R_6$ is hydrogen or a $C_{1-6}$ alkyl. In some embodiments, $R_5$ and $R_6$ are each independently hydrogen or methyl. In some embodiments, $R_5$ and $R_6$ are taken together to form a 5-6 membered unconjugated carbocyclic ring, e.g., cyclopentyl, unconjugated cyclopentenyl, cyclohexyl or unconjugated cyclohexenyl. In some embodiments, $R_7$ is hydrogen or hydroxyl. In some embodiments, $R_8$ is hydrogen or hydroxyl. In some embodiments, $R_9$ is —$OR_b$ or —$NR_eR_f$. In some embodiments, $R_b$ is hydrogen or a $C_{1-6}$ alkyl. In some embodiments, $R_9$ is —$NR_eR_f$. In some embodiments, $R_e$ is hydrogen or a $C_{1-6}$ alkyl. In some embodiments, $R_f$ is hydrogen, a $C_{1-6}$ alkyl or a base stable nitrogen protecting group. In some embodiments, $R_e$ is $C_{1-6}$ alkyl, e.g., methyl or ethyl, and $R_f$ is hydrogen or a base stable nitrogen protecting group. In some embodiments, $R_{10}$ is hydrogen.

The present invention is based, at least in part, on the control of the stereochemistry at the carbon indicated below in formula (V):

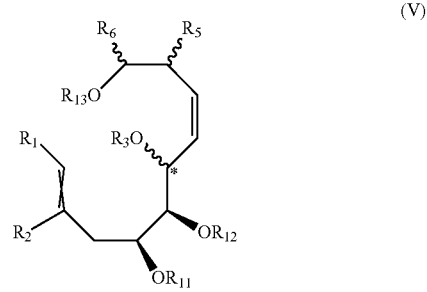

(V)

and/or the carbon indicated below in formula (VI):

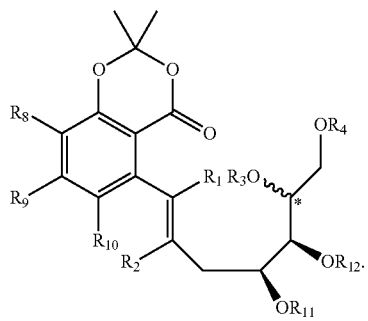

In previous methods of forming the compounds of formula (IV), the preparation of this fragment afforded a 1:2 mixture of the α and β isomers of formula (V). It was additionally determined by the present inventors that the α and β isomers produced vastly different yields when used in the subsequent synthesis of the final macrolide product. For example, in the production of compound 010, where the α and β isomers of the compounds of formula (V) were:

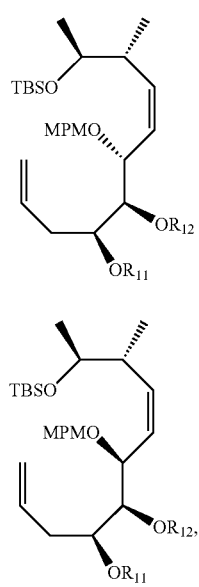

the yields obtained from subsequent reactions are shown below in Table 1.

TABLE 1

Yields of reaction steps in the production of compound 010

| Stage | α isomer yields† | β isomer yields‡ |
|---|---|---|
| Heck Coupling | 75% | 60-65% |
| Ethylation | 82% | ND* |
| TBS Cleavage | 75% | 42%** |
| Macrolactonization | 76% | 20%*** |

TABLE 1-continued

Yields of reaction steps in the production of compound 010

| Stage | α isomer yields† | β isomer yields‡ |
|---|---|---|
| Phenol Protection | 99% | ND |
| MPM Removal | 98% | 86% |
| PCC Oxidation | 81% | 82% |

*The ethylation reaction generated an ~1:1 mixture of the desired product and an elimination product. The 2 materials were not separable.
**Yield of the TBS cleavage reaction is based upon the 1:1 mixture mentioned above.
***The yield of the macrolactonization reaction can be improved to 63% by changing to lithium bis(trimethylsilyl)amide.

As can be seen in Table 1, the β isomer of the compound of formula (V) afforded significantly less yield in a number of the subsequent reactions steps. Moreover, the elimination byproduct which occurred in the ethylation of the β isomer is indicative of not only a significant loss in yield, but also to an impurity which is difficult to separate. Accordingly, and without wishing to be bound by any particular theory, it is believed that the elimination of the β isomer of the compound of formula (V) would produce not only a higher yield in subsequent reactions, but also a purer final product.

In some embodiments, the compounds and compositions are substantially free of elimination products, e.g., compounds of formula (XI):

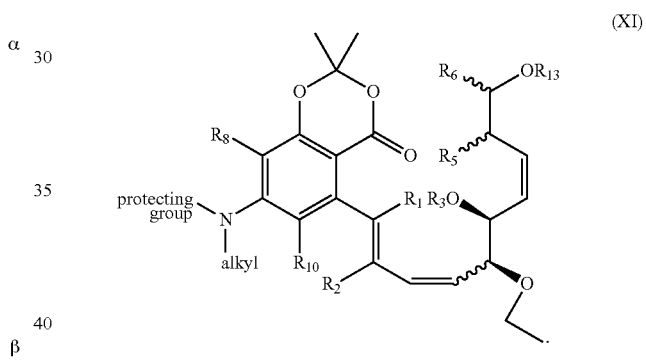

In some embodiments, the compounds and compositions are substantially free the elimination product represented by the following structure:

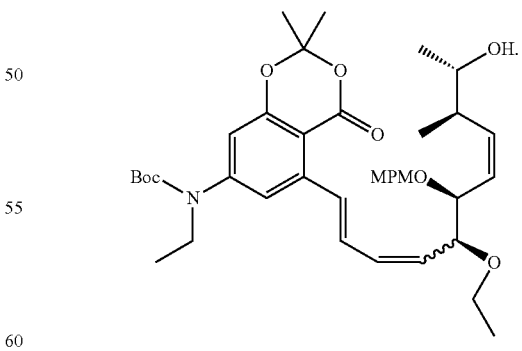

Accordingly, in some aspects, the present invention is directed to method for making an alpha-enhanced composition comprising a compound of formula (V). It was determined by the present inventors that an alpha-enhanced composition can be obtained by using starting materials having the appropriate stereochemistry. Accordingly, the alpha enhanced composition comprising a compound of formula (V) can be formed by reacting a compound of formula (I) with a compound of formula (II) under suitable conditions, such that an alpha-enhanced composition comprising a compound of formula (V) is formed. Similarly, in some aspects, the present invention is directed to method for making an alpha-enhanced composition comprising a compound of formula (VI). Such an alpha enhanced composition can be formed by reacting a compound of formula (I) with a compound of formula (III) under suitable conditions, such that an alpha-enhanced composition comprising a compound of formula (VI) is formed. In some embodiments, the compound of formula (I) is a compound of formula (Ib):

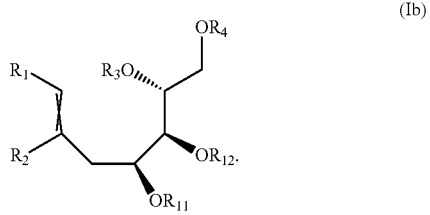

(Ib)

The present invention is also based, at least in part, on the fact that crystalline intermediates can be isolated, such that minimal chromatography is needed in the synthesis of the macrolide product. In previous methods of forming compounds of formula (IV), numerous chromatographic purifications were needed to remove impurities. (See, e.g., WO 03/076424, paragraphs [1099]-[1119]) Accordingly, and without wishing to be bound by any particular theory, it is believed that the elimination of chromatographic steps with maintenance of the appropriate purity and stereochemistry would improve the yield of the final macrolide product.

Accordingly, in some embodiments, the compound of formula (I) is crystalline. In other embodiments, the compound of formula (II) is crystalline. In still other embodiments, the compound of formula (III) is crystalline. In other embodiments, the compound of formula (IV) is produced in substantially pure form without the use of chromatography. In other embodiments, the compound of formula (V) is produced in substantially pure form without the use of chromatography. In other embodiments, the compound of formula (VI) is produced in substantially pure form without the use of chromatography.

In still other embodiments, the compound of formula (V) and/or the compound of formula (VI) is crystalline. It will be appreciated by the skilled artisan that the crystallization of intermediates does not necessarily proceed effortlessly or efficiently. Accordingly, in some embodiments, a crystallizable analog of the compound formula (V) and/or the compound of formula (VI) is formed as an intermediate. As used herein, the term "crystallizable analogs" refers to compounds of formula (V) and/or formula (VI) which have been modified such that they are able to be crystallized, while still maintaining their reactivity in subsequent reaction steps. For example, compounds of formula (V) and/or formula (VI) can be modified at one of the pendent oxygens with a protecting group, such that the protecting group facilitates crystallization. When the crystallizable analog is employed in subsequent steps, the protecting group can then be removed.

For example, without wishing to be bound by any particular theory, it is believed that introducing two conjugated rings into one or more of the molecules of the present invention can facilitate crystallization, e.g., by creating a favorable interaction between the two rings. Such interaction can be, for example, stacking of the rings due to the interaction of the pi-orbitals. This phenomenon may be referred to as "pi-stacking." Thus, in some embodiments, the molecules of the invention comprise two conjugated rings, which are capable of pi-stacking. In some embodiments, the rings comprise one or more substituents that facilitate pi-stacking. For example, pi-stacking may be enhanced by providing rings with dissimilar electronic characteristics (e.g., one electron-rich ring and one electron-poor ring). Such rings may be chosen, for example, based upon the presence of certain electron donating groups and/or electron withdrawing groups. That is, the presence of electron donating groups will typically render a ring more electron-rich, whereas the presence of electron withdrawing groups will typically render a ring more electron-poor. Exemplary electron donating groups include, but are not limited to $-O^-$, $-OH$, $-OR$, $-NH_2$, $-NR_2$, amides, $-OCOR$, alkyls (e.g., branched alkyls), phenyl groups and conjugated alkenyls. Exemplary electron withdrawing groups include, but are not limited to, $-NO_2$, $-NH_3^+$, $-NR_3^+$, $-SO_3H$, nitrile, $-CF_3$, carbonyl groups (e.g., $-COH$, $-COR$, $-COOH$ and $-COOR$) and halogens.

In some embodiments, the crystallizable analog of the compound of formula (V) is a compound of formula (VII):

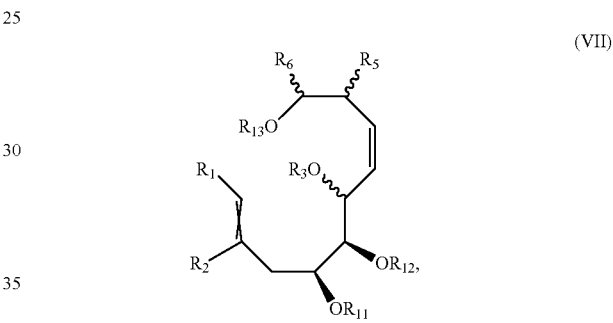

(VII)

e.g., formula (VII'):

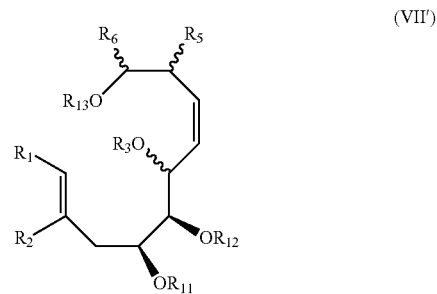

(VII')

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_3$ is selected from the group consisting of hydrogen and a base stable oxygen protecting group;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

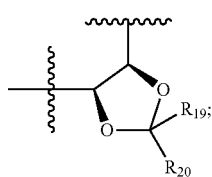

(a)

wherein $R_{19}$ and $R_{20}$ are each independently selected from the group consisting of hydrogen, $C_{1-6}$ alkyl, $C_{1-6}$ haloalkyl, $C_{1-6}$ alkoxy and phenyl, or $R_{19}$ and $R_{20}$ together represent a fluorenyl moiety of structure (b):

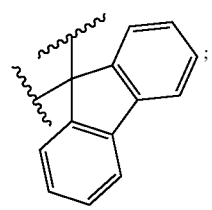

(b)

$R_{13}$ is a moiety of formula (VIII):

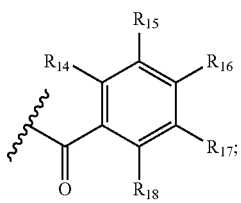

(VIII)

and $R_{14}, R_{15}, R_{16}, R_{17}$ and $R_{18}$ are each independently selected from the group consisting of H, $NO_2$, $-NH_3^+$, $-COH$, $-CO(C_{1-4}$ alkyl), $-COCl$, $-COOH$, $-COO(C_{1-4}$ alkyl), $-NR_3^+$, $-SO_3H$, nitrile, $-CF_3$ and halogen.

In some embodiments, $R_3$ is a first aromatic ring containing oxygen protecting group, e.g., a benzyl or benzoyl substituted with 0, 1, 2 or 3 substituents independently selected from $-OH$, $-O(C_{1-4}$alkyl), $-NH_2$, $-NH(C_{1-4}$alkyl), $-N(C_{1-4}$alkyl)$_2$, amides, $-OCO(C_{1-4}$alkyl) and $(C_{1-4}$alkyl).

In some embodiments, the crystallizable analog of the compound of formula (V) is a compound of formula (VII):

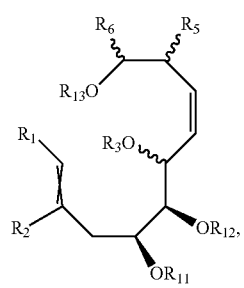

(VII)

e.g., formula (VII'):

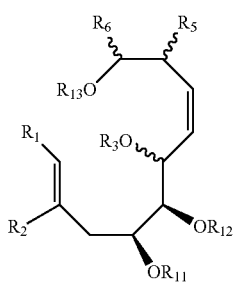

(VII')

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_3$ is a first aromatic ring-containing oxygen protecting group;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

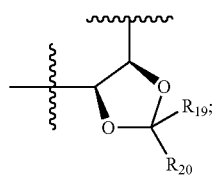

(a)

wherein $R_{19}$ and $R_{20}$ are each independently selected from the group consisting of hydrogen, $C_{1-6}$ alkyl, $C_{1-6}$ haloalkyl, $C_{1-6}$ alkoxy and phenyl, or $R_{19}$ and $R_{20}$ together represent a fluorenyl moiety of structure (b):

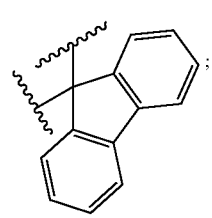

(b)

$R_{13}$ is a second aromatic ring-containing oxygen protecting group.

In some embodiments, $R_{13}$ is a benzoyl or benzyl substituted with at least one substituent, where each substituent is independently selected from $-NO_2$, $-NH_3^+$, $-NH_2(C_{1-4}$alkyl)$^+$, $-NH(C_{1-4}$alkyl)$_2^+$, $-N(C_{1-4}$alkyl)$_3^+$, $-SO_3H$, nitrile, $-CF_3$, $-COH$, $-CO(C_{1-4}$alkyl), $-COOH$ and $-COO(C_{1-4}$alkyl).

In some embodiments, $R_{13}$ is a moiety of formula (VIII):

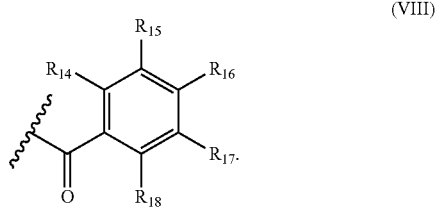

(VIII)

As used herein, the term "aromatic ring containing oxygen protecting group" refers to an oxygen protecting group as described in more detail herein, which possesses in the structure at least one aromatic ring. An aromatic ring refers to a ring system (e.g., benzene) containing conjugated double bonds. Such a structure typically results in electrons delocalized around the ring system. In some embodiments, the aromatic ring-containing oxygen protecting group is a substituted or unsubstituted benzoyl. In some embodiments, the aromatic ring-containing oxygen protecting group is a substituted or unsubstituted benzyl.

In some embodiments, the first aromatic ring-containing oxygen protecting group is a benzoyl or benzyl substituted with at least one electron withdrawing group and the second aromatic ring-containing oxygen protecting group is a benzoyl or benzyl substituted with at least one electron donating group. In other embodiments, the first aromatic ring-containing oxygen protecting group is a benzoyl or benzyl substituted with at least one electron donating group and the second aromatic ring-containing oxygen protecting group is a benzoyl or benzyl substituted with at least one electron withdrawing group. The electron donating and electron withdrawing groups may be any of those described above. In some embodiments, the first aromatic ring-containing oxygen protecting group is a benzoyl or benzyl substituted with at least one substituent, where each substituent is independently selected from —OH, —O($C_{1-4}$alkyl), —NH$_2$, —NH($C_{1-4}$alkyl), —N($C_{1-4}$alkyl)$_2$, amides, —OCO($C_{1-4}$ alkyl) and ($C_{1-4}$alkyl). In some embodiments, the second aromatic ring-containing oxygen protecting group is a benzoyl or benzyl substituted with at least one substituent, where each substituent is independently selected from —NO$_2$, —NH$_3^+$, —NH$_2$($C_{1-4}$alkyl)$^+$, —NH($C_{1-4}$alkyl)$_2^+$, —N($C_{1-4}$alkyl)$_3^+$, —SO$_3$H, nitrile, —CF$_3$, —COH, —CO($C_{1-4}$alkyl), —COOH and —COO($C_{1-4}$alkyl).

Regarding compounds of formula (VII), in some embodiments, $R_1$ is hydrogen. In some embodiments, $R_2$ is hydrogen. In some embodiments, $R_1$ and $R_2$ are both hydrogen. In some embodiments, $R_3$ is a benzyl substituted with 0, 1, 2, or 3 substituents independently selected from —OH, —O($C_{1-4}$alkyl), —NH$_2$, —NH($C_{1-4}$alkyl), —N($C_{1-4}$alkyl)$_2$, amides, —OCO($C_{1-4}$alkyl) and ($C_{1-4}$alkyl). In some embodiments, $R_3$ is 4-methoxybenzyl. In some embodiments, $R_5$ is hydrogen or a $C_{1-6}$ alkyl. In some embodiments, $R_6$ is hydrogen or a $C_{1-6}$ alkyl. In some embodiments, $R_5$ and $R_6$ are each independently hydrogen or methyl.

In some embodiments, one of $R_{14}$, $R_{15}$, $R_{16}$, $R_{17}$, and $R_{18}$ is selected from the group consisting of NO$_2$, —NH$_3^+$, —COH, —CO($C_{1-4}$ alkyl), —COCl, —COOH, —COO($C_{1-4}$ alkyl), —NR$_3^+$, —SO$_3$H, nitrile, —CF$_3$ and halogen and the other four of $R_{14}$, $R_{15}$, $R_{16}$, $R_{17}$, and $R_{18}$ are hydrogen. In some embodiments, at least one of $R_{14}$, $R_{15}$, $R_{16}$, $R_{17}$, and $R_{18}$ is selected from the group consisting of NO$_2$, —NH$_3^+$, —COH, —CO(C alkyl), —COCl, —COOH, —COO($C_{1-4}$ alkyl), —NR$_3^+$, —SO$_3$H, nitrile, —CF$_3$ and halogen and the other of $R_{14}$, $R_{15}$, $R_{16}$, $R_{17}$, and $R_{18}$ are hydrogen. In some embodiments, $R_{16}$ is NO$_2$ and each of $R_{14}$, $R_{15}$, $R_{17}$, and $R_{18}$ are independently hydrogen.

In some embodiments, the double bond represented by

represents a double bond where the substituents are situated in a cis position, relative to each other.

In some embodiments, the compound of formula (VII) is a compound of formula (VIIa)

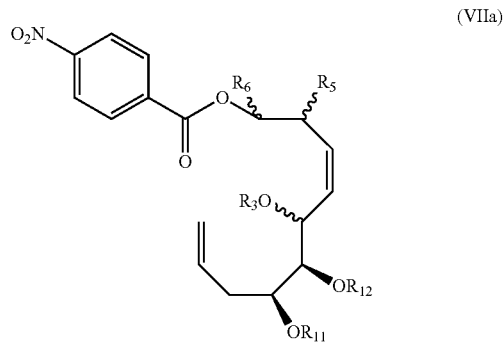

(VIIa)

In some embodiments, the compound of formula (VII) is a compound of formula (VIIb):

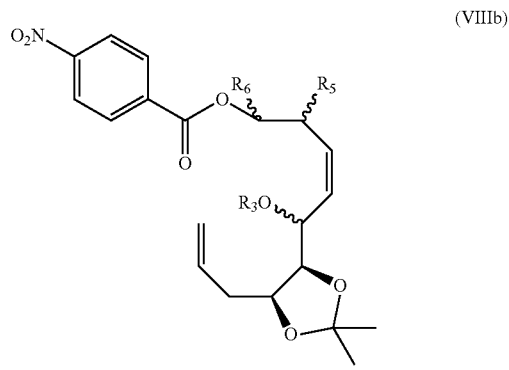

(VIIIb)

The present invention is also based, at least in part, on the fact that highly soluble intermediates can be separated from insoluble or sparingly soluble impurities, such that less chromatography is needed in the synthesis of the macrolide product. As indicated supra, previous methods of forming compounds of formula (IV) relied on numerous chromatographic purifications to remove impurities. Again, without wishing to be bound by any particular theory, it is believed that the elimination of one or more of such chromatographic steps with maintenance of the appropriate purity and stereochemistry would not only improve the yield of the final macrolide product, but also lower the time and cost of production and decrease the quantity of reagents, e.g., organic solvents, utilized in the synthesis of compounds of formula (IV).

Accordingly, in some embodiments, the intermediates of the present invention can be rendered highly soluble by the attachment of a solubility-promoting group. In some embodiments, the attachment of a solubility-promoting group is reversible. For example, in some embodiments the addition of the solubility-promoting group may be likened to the addition of a nitrogen or oxygen protecting group. Without wishing to be bound by any particular theory, it is believed that the attachment of a solubility-promoting group allows the target compound to be drawn into water, thus leaving any moiety that did not become derivatized with the solubility-promoting group in the organic media. Accordingly, in some embodiments, a soluble analog of the compound formula (I) is formed as an intermediate. As used herein, the term "soluble analogs" refers to compounds of formula (I) which have been modified (e.g., by the attachment of a solubility-promoting group) such that they are soluble in aqueous solutions. For example, compounds of formula (I) and/or formula (VI) can be modified at one of the pendent oxygens with a solubility-promoting group, such that the solubility-promoting group facilitates dissolution of the compound in aqueous medium. The skilled artisan may then take advantage of the difference in solubility of the compound of interest and the impurities to isolate the compound of interest without the use of chromatography. The solubility-promoting group can be removed subsequent to isolation of the compound If interest.

In some embodiments, the soluble analog of the compound of formula (I) is a compound of formula (XIII):

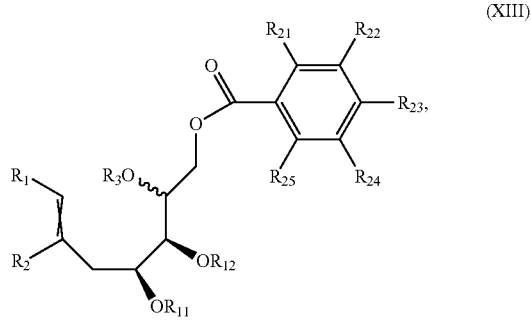

(XIII)

e.g., formula (XIII'):

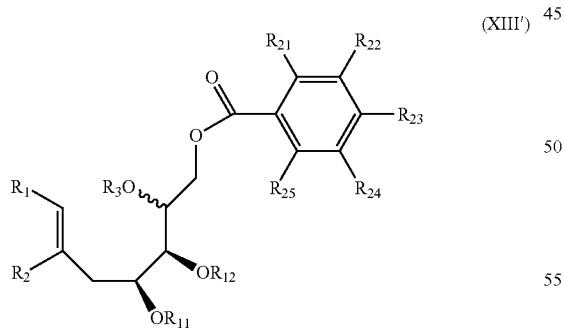

(XIII')

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_3$ is selected from the group consisting of hydrogen and a base stable oxygen protecting group;

$R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

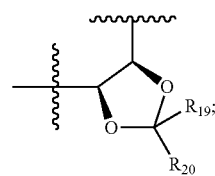

(a)

wherein $R_{19}$ and $R_{20}$ are each independently selected from the group consisting of hydrogen, $C_{1-6}$ alkyl, $C_{1-6}$ haloalkyl, $C_{1-6}$ alkoxy and phenyl, or $R_{19}$ and $R_{20}$ together represent a fluorenyl moiety of structure (b):

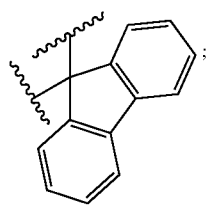

(b)

and one, two or three of $R_{21}$, $R_{22}$, $R_{23}$, $R_{24}$, and $R_{25}$ are acidic-hydrogen containing moieties or salts thereof, and the remainder of $R_{21}$, $R_{22}$, $R_{23}$, $R_{24}$, and $R_{25}$ are each independently hydrogen, methyl, hydroxyl or amino.

As used herein, the term "acidic-hydrogen containing moiety" refers to a substituent group that includes at least one acidic hydrogen. Acidic-hydrogen containing moieties include, for example, —COOH, —SO$_3$H, —SO$_4$H, —PO$_3$H$_2$ and —PO$_4$H$_2$. It is to be understood that an acidic-hydrogen containing moiety may be positioned ortho, meta or para to the core of the compound of formula (XII), i.e., the

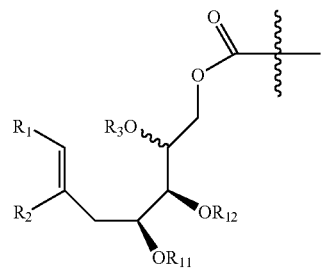

moiety. In some embodiments, an acidic-hydrogen containing moiety is ortho to the core of the compound of formula (XII).

In some embodiments, $R_{21}$ is —COOH or a salt thereof. In some embodiments $R_{21}$ is —SO$_3$H or a salt thereof. In some embodiments, $R_{22}$, $R_{23}$, $R_{24}$, and $R_{25}$ are each independently hydrogen. In some embodiments, $R_{22}$ is —COOH or a salt thereof. In some embodiments $R_{22}$ is —SO$_3$H or a salt thereof. In some embodiments, $R_{21}$, $R_{23}$, $R_{24}$, and $R_{25}$ are each independently hydrogen.

In some embodiments, $R_1$, $R_2$, $R_3$, $R_{11}$, $R_{12}$, $R_{19}$ and $R_{20}$ are selected from the substituents provided in connection with Compound (I). For example, in some embodiments, $R_1$ and $R_2$ are each independently hydrogen. In some embodiments, $R_{11}$ and $R_{12}$ are taken together to form a 5 membered heterocyclyldiyl of structure (a):

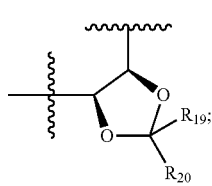

wherein $R_{19}$ and $R_{20}$ are each independently $C_{1-6}$ alkyl.

In some embodiments, the compounds of formula (I), formula (II) and formula (III) are reacted to form a compound of formula (IV'):

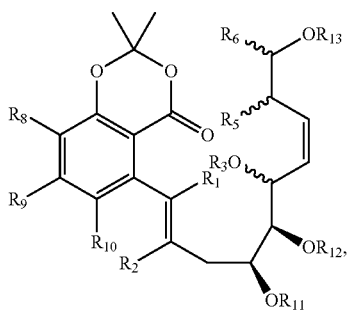

which is subsequently converted to a compound of formula (IV), e.g., by macrolactonization using potassium t-butoxide and subsequent deprotection/oxidation. It has also been determined that the removal of a protecting group at the $R_3$ position of formula (IV') (e.g., the DDQ removal of the p-methoxybenzyl ether to form a hydroxy moiety) generates p-anisaldehyde. p-Anisaldehyde has been found, in turn, to be responsible for the formation of a dimeric impurity:

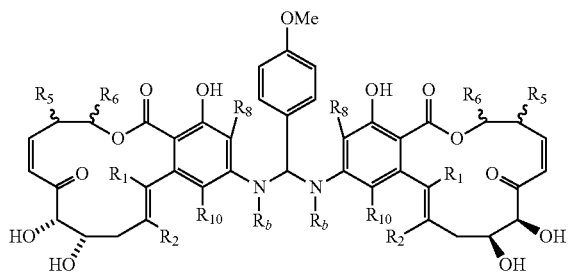

wherein substituents are as described above. Although the dimer was re-subjected to the reaction conditions, it did not degrade back to the monomer and p-anisaldehyde. This indicates that it is stable. Also, some initial biological testing indicated that the dimer had lower potency and greater cytotoxicity than the monomer, making it an undesirable impurity.

Accordingly, in some embodiments, the compounds and compositions of the present invention are substantially free of dimeric products. In some embodiments, a semicarbazide hydrochloride in the presence of sodium acetate is added to the reaction mixture. Without wishing to be bound by any particular theory, it is believed that this may form an imine derivative, which could precipitate from solution and be removed by filtration.

In some embodiments, the compounds of formula (I), formula (II) and formula (III) are reacted to form a compound of formula (IV"):

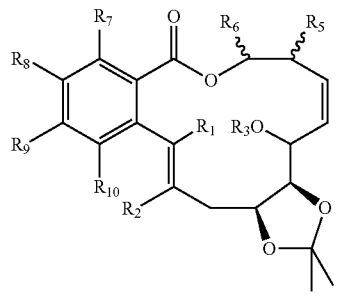

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_3$ is a base stable oxygen protecting group;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_7$ is $-OR_a$ wherein $R_a$ is a base stable oxygen protecting group;

$R_8$ is selected from the group consisting of hydrogen and $-OR_g$ wherein $R_g$ is hydrogen or a base stable oxygen protecting group;

$R_9$ is selected from the group consisting of hydrogen, halogen, $-OR_b$, $C_{1-6}$ alkyl, $C_{3-6}$ unconjugated alkenyl, $C_{3-6}$ unconjugated alkynyl, $C_{1-6}$ haloalkyl, $-SR_d$ and $-NR_eR_f$ wherein $R_b$ is hydrogen or a base stable oxygen protecting group, wherein $R_d$ is selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl and wherein $R_e$ and $R_f$ are each independently selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl or a base stable nitrogen protecting group; and $R_{10}$ is selected from the group consisting of hydrogen, halogen, $-OR_c$, $C_{1-6}$ alkyl, $C_{3-6}$ unconjugated alkenyl, $C_{3-6}$ unconjugated alkynyl, $C_{1-6}$ haloalkyl and $C_{1-6}$ alkoxy, wherein $R_c$ is hydrogen or a base stable oxygen protecting group;

which is subsequently converted to a compound of formula (IV), e.g., by subsequent deprotection/oxidation. Deprotection can occur at any or all of $R_3$, $R_7$ or the structure represented by the heterocyclyldiyl of formula XII:

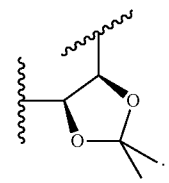

In some embodiments, deprotection occurs at all of $R_3$, $R_7$ and the structure represented by the heterocyclyldiyl of formula (XII) at the same time. In other embodiments, deprotection occurs at $R_7$ first, followed by subsequent deprotection at $R_3$ and the structure represented by the heterocyclyldiyl of formula (XII).

In other aspects, the present invention is directed to methods for making a purity-enhanced composition comprising a compound of formula (IV). It was also determined by the present inventors that a purity-enhanced composition can be obtained by using starting materials having the appropriate stereochemistry, and thus forming alpha-enhanced intermediates (e.g., alpha-enhanced compositions comprising formula (V) or formula (VI)) as well as targeting crystalline intermediates which can be isolated in substantially pure form without chromatography. The methods for making a purity-enhanced composition comprising a compound of formula (IV) typically include combining a compound of formula (I) with a compound of formula (II) and a compound of formula (III), under suitable conditions, such that a purity-enhanced composition comprising a compound of formula (IV) is formed.

Similarly, in other aspects, the present invention is directed to methods for making a composition comprising a compound of formula (IV), wherein the composition is substantially free of organic impurities. The methods typically include combining a compound of formula (I) with a compound of formula (II) and a compound of formula (III), under suitable conditions, such that a composition comprising a compound of formula (IV) substantially free of organic impurities is formed.

In still other aspects, the present invention is directed to methods for making a yield-enhanced composition comprising a compound of formula (IV). The methods typically include combining a compound of formula (I) with a compound of formula (II) and a compound of formula (III), under suitable conditions, such that a composition comprising a compound of formula (IV) is formed.

The skilled artisan would be able to appreciate that the reaction conditions employed herein may vary. For example, many reagents can be utilized in coupling the compounds of any of formulae (I)-(III) and (V)-(VI) with one another. Moreover, many reagents can be utilized in protection, deprotection, macrolactonization and oxidation of various intermediates. Additionally, the time taken for the reaction may vary depending upon reagents and concentrations. Additionally, the reactions of the present invention may occur at varying temperatures. Numerous solvents can also be employed in the reactions of the present invention. Suitable solvents are liquids at ambient room temperature and pressure or remain in the liquid state under the temperature and pressure conditions used in the reaction. Useful solvents are not particularly restricted provided that they do not interfere with the reaction itself (that is, they preferably are inert solvents), and they dissolve a certain amount of the reactants. Depending on the circumstances, solvents may be distilled or degassed. Solvents may be, for example, aliphatic hydrocarbons (e.g., hexanes, heptanes, ligroin, petroleum ether, cyclohexane, or methylcyclohexane) and halogenated hydrocarbons (e.g., methylenechloride, chloroform, carbontetrachloride, dichloroethane, chlorobenzene, or dichlorobenzene); aromatic hydrocarbons (e.g., benzene, toluene, tetrahydronaphthalene, ethylbenzene, or xylene); ethers (e.g., diglyme, methyl-tert-butyl ether, methyl-tert-amyl ether, ethyl-tert-butyl ether, diethylether, diisopropylether, tetrahydrofuran or methyltetrahydrofurans, dioxane, dimethoxyethane, or diethyleneglycol dimethylether); nitriles (e.g., acetonitrile); ketones (e.g., acetone); esters (e.g., methyl acetate or ethyl acetate); alcohols (e.g., methanol) and mixtures thereof. The skilled artisan would be able to determine, without undue experimentation, proper reaction conditions using the teachings of the present invention.

Analysis of Beneficial Reaction Properties

In one embodiment, the methods of preparation of the invention are advantageous over the methods that currently in use for the synthesis of macrolides of the present invention. In certain embodiments, a method of the invention possesses a beneficial reaction property (BRP).

The language "beneficial reaction property or BRP" includes a property of one reaction that is beneficial over an existing manner of performing the same reaction. The property may be any property suitable to comparison to the existing methodology, such that the property is equal to or better in nature than the property of the existing methodology. Examples of such properties include, without limitation, starting material safety, reaction time, energy cost, reaction safety, product mass balance (reduction of waste), reaction cleanliness, waste, throughput, workup, overall process time, and overall cost of the target product. Several particular examples of beneficial reaction properties as applied to the preparation of compound 010 are discussed below.

Cost Effectiveness

In preparing compound 010, the ethylation of the aromatic nitrogen (i.e., $R_9$ in formula (IV)) is a throughput-limiting step. In the methodology that has previously been used, the ethylation occurs late in the synthesis where the entire carbon skeleton is in place. Thus, any limitations of the ethylation reaction place the entire skeleton, including all starting materials, at risk. By performing the ethylation earlier, the risk to other fragments is eliminated and overall synthetic convergence is increased. Accordingly, in some embodiments, the substituent $R_9$ of the compound of formula (III) is such that no alkylation needs to occur in subsequent steps in the formation of a compound of formula (IV).

Waste/Impurities

Theoretically, for the previous methods for synthesizing compound 010, at least 33% of the mass on the product side is waste. For example, about 66% of the compound of formula (V) produced in previous methods is the β isomer, and about 50% of the product resulting from the β isomer is an inseparable elimination by-product of the structure:

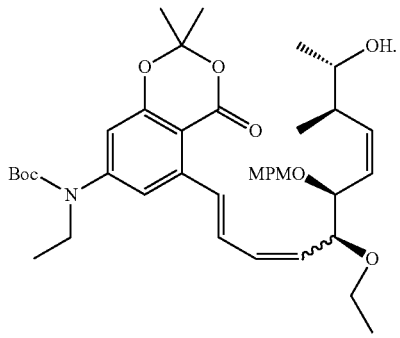

Moreover, with regard to the total amount of waste, the methods of the present invention can further reduce waste over previous methods by the elimination of chromatography steps. Such reduction of waste can lead, e.g., to further savings in time, cost, hazardous waste treatments, etc.

Intermediates of the Invention

The present invention is also directed, at least in part, to intermediates for use in the synthesis of compounds and compositions of the present invention, e.g., compounds of formula (IV). As discussed above, it is desirable to have crystalline intermediates in the synthesis of a final product, at least so that chromatography steps may be eliminated.

It is to be understood that, in addition to the specific intermediates listed in Schemes 1 and 2, above, the present invention also encompasses crystallizable analogs of such intermediates. In some embodiments, one or more of the specific intermediates listed in Schemes 1 and 2 will not readily or efficiently crystallize. As described in more detail above, intermediates can be modified such that they are able to be crystallized. Such modified intermediates will maintain their reactivity in subsequent reaction steps.

Accordingly, in some aspects the present invention is directed to intermediates of formula (VII):

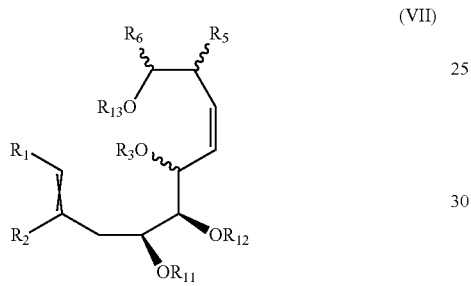

(VII)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_3$ is selected from the group consisting of hydrogen and a base stable oxygen protecting group;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

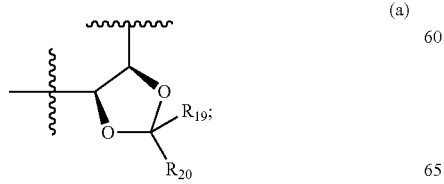

(a)

$R_{13}$ is a moiety of formula (VIII):

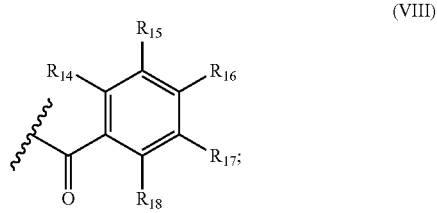

(VIII)

and $R_{14}$, $R_{15}$, $R_{16}$, $R_{17}$ and $R_{18}$ are each independently selected from the group consisting of H, $NO_2$, $-NH_3^+$, $-COH$, $-CO(C_{1-4}$ alkyl), $-COCl$, $-COOH$, $-COO(C_{1-4}$ alkyl), $-NR_3^+$, $-SO_3H$, nitrile, $-CF_3$ and halogen.

In certain aspects, the present invention is directed to intermediates of formula (VII):

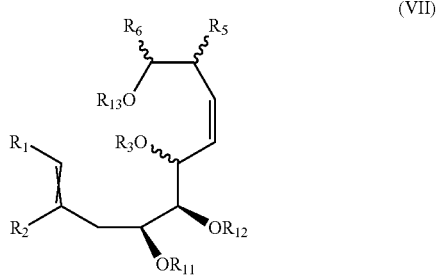

(VII)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_3$ is an aromatic ring-containing oxygen protecting group;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

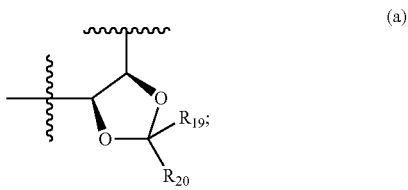

(a)

wherein $R_{19}$ and $R_{20}$ are each independently selected from the group consisting of hydrogen, $C_{1-6}$ alkyl, $C_{1-6}$ haloalkyl, $C_{1-6}$ alkoxy and phenyl, or $R_{19}$ and $R_{20}$ together represent a fluorenyl moiety of structure (b):

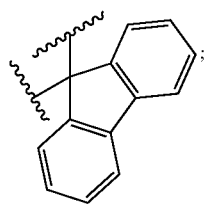

(b)

$R_{13}$ is a an aromatic ring-containing oxygen protecting group.

Exemplary values for $R_1$, $R_2$, $R_3$, $R_5$, $R_6$, $R_{11}$, $R_{12}$ and $R_{13}$ are described in more detail above in connection with the crystallizable analogs of formula (VII).

In some embodiments, the compound of formula (VII) is a compound of formula (VIIa)

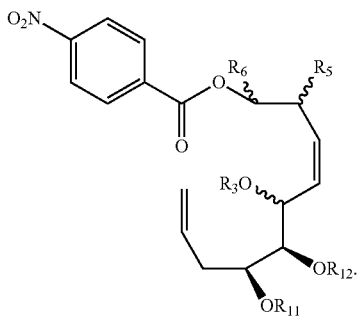

(VIIa)

In some aspects, the present invention is directed to an intermediate of formula (IX):

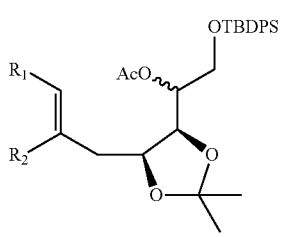

(IX)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl. In some embodiments, $R_1$ is hydrogen. In some embodiments, $R_2$ is hydrogen. In some embodiments, $R_1$ and $R_2$ are each independently hydrogen.

In still other aspects the present invention is directed to an intermediate of formula (X):

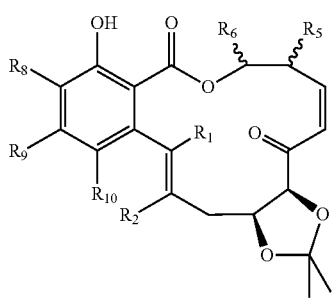

(X)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_8$ is selected from the group consisting of hydrogen and —$OR_g$ wherein $R_g$ is hydrogen or a base stable oxygen protecting group, $R_9$ is selected from the group consisting of hydrogen, halogen, —$OR_b$, $C_{1-6}$ alkyl, $C_{3-6}$ unconjugated alkenyl, $C_{3-6}$ unconjugated alkynyl, $C_{1-6}$ haloalkyl, —$SR_d$ and —$NR_eR_f$ wherein $R_b$ is hydrogen or a base stable oxygen protecting group, wherein $R^d$ is selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl and wherein $R_e$ and $R_f$ are each independently selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl or a base stable nitrogen protecting group; and $R_{10}$ is selected from the group consisting of hydrogen, halogen, —$OR_c$, $C_{1-6}$ alkyl, $C_{3-6}$ unconjugated alkenyl, $C_{3-6}$ unconjugated alkynyl, $C_{1-6}$ haloalkyl and $C_{1-6}$ alkoxy, wherein $R_c$ is hydrogen or a base stable oxygen protecting group.

In some embodiments, $R_1$ is hydrogen. In some embodiments, $R_2$ is hydrogen. In some embodiments, $R_1$ and $R_2$ are each independently hydrogen. In some embodiments, $R_5$ is hydrogen or a $C_{1-6}$ alkyl. In some embodiments, $R_6$ is hydrogen or a $C_{1-6}$ alkyl. In some embodiments, $R_5$ and $R_6$ are each independently hydrogen or methyl. In some embodiments, $R_8$ is hydrogen. In some embodiments, $R_{10}$ is hydrogen. In some embodiments, $R_9$ is —$OR_b$ or —$NR_eR_f$. In some embodiments, $R_b$ is hydrogen or a $C_{1-6}$ alkyl. In some embodiments, $R_9$ is —$NR_eR_f$. In some embodiments, $R_e$ is hydrogen or a $C_{1-6}$ alkyl. In some embodiments, $R_f$ is hydrogen, a $C_{1-6}$ alkyl or a base stable nitrogen protecting group. In some embodiments, $R_e$ is $C_{1-6}$ alkyl, e.g., methyl or ethyl, and $R_f$ is hydrogen or a base stable nitrogen protecting group.

In some embodiments, the compound of formula (X) is a compound of formula (Xa)

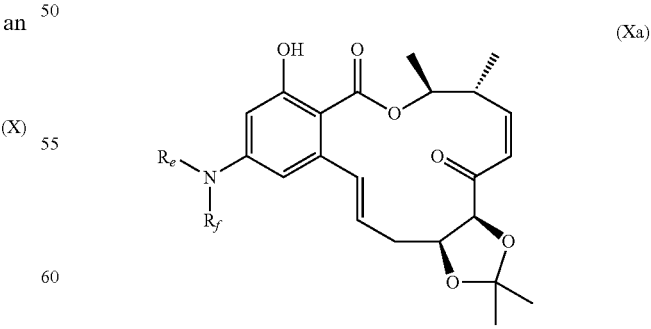

(Xa)

wherein $R_e$ is selected from the group consisting of hydrogen, $C_{1-6}$ alkyl, $C_{2-6}$ alkenyl, $C_{2-6}$ alkynyl, $C_{1-6}$ heteroalkyl, heteroaryl, and aryl; and $R_f$ is a base stable nitrogen protecting group.

In other embodiments, the present invention is directed to compositions that include intermediates of formula (X), wherein the composition is substantially free of compounds of formula (IV):

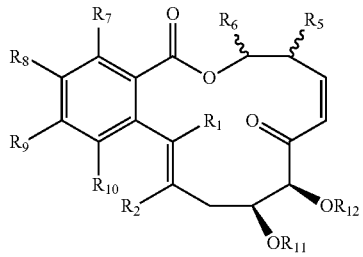

(IV)

wherein $R_1$ and $R_2$ are each independently selected from the group consisting of hydrogen, $C_{1-6}$ alkyl, $C_{3-6}$ unconjugated alkenyl and $C_{3-6}$ unconjugated alkynyl;

$R_5$ and $R_6$ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and $NH_2$; or $R_5$ and $R_6$ are taken together with the carbons on which they are attached to form a 5-6 membered unconjugated carbocyclic ring;

$R_7$ is —$OR_a$ wherein $R_a$ is a base stable oxygen protecting group;

$R_8$ is selected from the group consisting of hydrogen and —$OR_g$ wherein $R_g$ is hydrogen or a base stable oxygen protecting group;

$R_9$ is selected from the group consisting of hydrogen, halogen, —$OR_b$, $C_{1-6}$ alkyl, $C_{3-6}$ unconjugated alkenyl, $C_{3-6}$ unconjugated alkynyl, $C_{1-6}$ haloalkyl, —$SR_d$ and —$NR_eR_f$ wherein $R_b$ is hydrogen or a base stable oxygen protecting group, wherein $R_d$ is selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl and wherein $R_e$ and $R_f$ are each independently selected from the group consisting of hydrogen, $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl or a base stable nitrogen protecting group;

$R_{10}$ is selected from the group consisting of hydrogen, halogen, —$OR_c$, $C_{1-6}$ alkyl, $C_{3-6}$ unconjugated alkenyl, $C_{3-6}$ unconjugated alkynyl, $C_{1-6}$ haloalkyl and $C_{1-6}$ alkoxy, wherein $R_c$ is hydrogen or a base stable oxygen protecting group; and $R_{11}$ and $R_{12}$ are each independently hydrogen.

In other aspects the present invention is directed to an intermediate of formula (III):

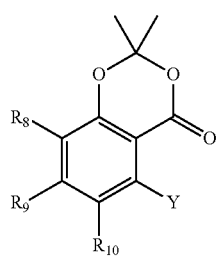

(III)

wherein Y is a halogen or a triflate (—O—$SO_2CF_3$);

$R_8$ is selected from the group consisting of hydrogen and —$OR_g$ wherein $R_g$ is hydrogen or a base stable oxygen protecting group, $R_9$ is —$NR_eR_f$; wherein $R_e$ is selected from the group consisting of $C_{1-6}$ alkyl, $C_{2-6}$ alkenyl, $C_{2-6}$ alkynyl, $C_{1-6}$ heteroalkyl, 5-7 membered heteroaryl comprising 1, 2 or 3 heteroatoms, and $C_{5-7}$ aryl, and wherein $R_f$ is a base stable nitrogen protecting group; and $R_{10}$ is selected from the group consisting of hydrogen, halogen, —$OR_c$, $C_{1-6}$ alkyl, $C_{2-6}$ alkenyl, $C_{2-6}$ alkynyl, $C_{1-6}$ haloalkyl and $C_{1-6}$ alkoxy, wherein $R_c$ is hydrogen or a base stable oxygen protecting group. In some embodiments, $R_8$ is hydrogen. In some embodiments, $R_{10}$ is hydrogen. In some embodiments, $R_e$ is a $C_{1-6}$ alkyl, e.g., methyl or ethyl. In some embodiments, $R_f$ is —BOC.

In still other aspects, the present invention is directed to an intermediate of any of formulae (I)-(III) or (V)-(VII) as described herein above in the Methods section.

In other aspects, the present invention is directed to the use of any one of the compounds of formulae (I)-(III) or (V)-(IX) as an intermediate in the synthesis of a compound of formula (IV). For example, in some embodiments, the present invention is directed to the use of any one of the compounds of formulae (I)-(III) or (V)-(IX) as an intermediate in the synthesis of a purity-enhanced or yield-enhanced composition comprising a compound of formula (IV). In some embodiments, the present invention is directed to the use of an alpha-enhanced composition comprising a compound of formula (V) and/or formula (VI) in the synthesis of a purity-enhanced or yield-enhanced composition comprising a compound of formula (IV).

Compounds and Compositions Prepared Using Methods of the Invention

In some aspects, the present invention is directed to compounds and compositions prepared using the methods of the present invention, e.g., alpha-enhanced compositions. In some embodiments, the compounds and compositions are appropriate for use in the therapeutic formulations. Such therapeutic formulations can be, e.g., those described in more detail below. In other embodiments, the compounds and compositions are appropriate for use in the synthesis of other products, e.g., compounds of formula (IV).

Uses of Compositions of the Invention

In general, the present invention provides compounds useful for the treatment of inflammatory or immune disorders and the treatment of cancer, particularly solid tumors. In some embodiments, the compounds of the invention inhibit NF-κB activity, and accordingly may be effective in inflammatory and immune disorders (see, generally, NF-κB in Defense and Disease, J. Clin. Investig 2001, 107, 7). Furthermore, certain compounds of the invention have also been shown to inhibit receptor tyrosine kinase activity such as VEGFr and PDGFr in vitro, and are useful for the treatment of cancer, including solid tumors (see, Angiogenesis: Potentials for Pharmacologic Intervention in the Treatment of Cancer, Cardiovascular Diseases, and Chronic Inflammation, Pharmacological Reviews, 2000, 52, 237).

Accordingly, in some embodiments, compounds of the present invention exhibited $IC_{50}$ values for NF-κB inhibition of less than 10 μM. In certain other embodiments, compounds of the present invention exhibited $IC_{50}$ values less than 7.5 μM. In certain embodiments, compounds of the present invention exhibited $IC_{50}$ values less than 5 μM, less than 2.5 μM, less than 1 μM. In certain embodiments, compounds of the present invention exhibited $IC_{50}$ values less than 0.75 μM, less than 0.5 μM, less than 0.25 μM, less than 0.1 μM, less than 75 nM, less than 50 nM or even less than 25 nM.

In still other embodiments, compounds of the present invention exhibited $IC_{50}$ values for inhibition of the growth of tumor cell lines in vitro of less than 10 µM. In certain other embodiments, compounds of the present invention exhibited $IC_{50}$ values less than 7.5 W. In certain embodiments, compounds of the present invention exhibited $IC_{50}$ values less than 5 µM, less than 2.5 µM, less than 1 µM. In certain embodiments, compounds of the present invention exhibited $IC_{50}$ values less than 0.75 µM, less than 0.5 µM, less than 0.25 µM, less than 0.1 µM, less than 75 nM, less than 50 nM or even less than 25 nM.

As discussed above, compounds of the invention exhibit immunomodulatory activity and exhibit activity for the inhibition of angiogenesis through inhibition of receptor tyrosine kinases. As such, the inventive compounds may by useful for the treatment of a variety of disorders, including, but not limited to, sepsis, glomerulonephropathy, rheumatoid arthritis (including ankylosing spondylitis), psoriatic arthritis, osteoarthritis, osteoporosis, allergic rhinitis, ocular inflammation, inflammatory bowel disease, atopic dermatitis, psoriasis, asthma, Crohn's disease, ulcerative colitis, inflammatory pulmonary disease, hepatitis, autoimmune disorders, diabetes, AIDS, solid tumor cancers, Leukemia, lymphomas, non-hodgkin's B-cell lymphomas, chronical lymphocytic leukemia (CLL), multiple myeloma, systemic lupus erythematosus, allograft rejection/graft versus host disease, eczema, uticaria, myasthenia gravis, idiopathic thrombocytopenia purpura, cardiovascular disease (e.g., myocardial infarction, atherosclerosis), hepatitis, productive nephritis, adenovirus, diseases/disorders of the central nervous system (stroke, Alzheimer's disease, epilepsy) and for the treatment of the symptoms of malaria, to name a few. In certain embodiments, compounds of the invention are particularly useful for the treatment of rheumatoid arthritis, psoriasis, multiple sclerosis, asthma and cancer. In certain embodiments, compounds of the invention are particularly useful for the treatment of psoriasis. In certain embodiments, compounds of the invention are particularly useful for the treatment of cancer. In certain embodiments, compounds of the invention are particularly useful for the treatment of atopic dermatitis. Additional information and guidance for the treatment of such diseases can be found, e.g., in U.S. Patent Application publication number 2006/0247448, the entire contents of which are incorporated herein by this reference.

Dosages and Modes of Administration

It will be appreciated that the compounds and compositions formed according to the methods of the present invention may be administered using any amount and any route of administration effective for the treatment of any of the disease states indicated herein. Thus, the expression "effective amount" as used herein for the treatment of cancer, refers to a sufficient amount of agent to inhibit the growth of tumor cells, or refers to a sufficient amount to reduce the effects of cancer. The exact amount required will vary from subject to subject, depending on the species, age, and general condition of the subject, the severity of the diseases, the particular anticancer agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

Pharmaceutical compositions can be administered systemically, e.g., enteral and parenteral methods of administration such as intravenous administration, intraperitoneal administration, intramuscular administration, intracoronary administration, intraarterial administration (e.g., into a carotid artery), intradermal administration, subcutaneous administration, transdermal delivery, intratracheal administration, subcutaneous administration, intraarticular administration, intraventricular administration, inhalation (e.g., aerosol), intracerebral, nasal, naval, oral, intraocular, pulmonary administration, impregnation of a catheter, by suppository and direct injection into a tissue, or systemically absorbed topical or mucosal administration. Guidance for systemic administration of compositions of the present invention, including appropriate dosage forms, dosages and dosing schedules can be found, e.g., in U.S. Patent Application publication number 2006/0247448, the entire contents of which are incorporated herein by this reference. In certain exemplary embodiments, the inventive compounds may be used as coating for stents. Guidance for using compounds of the invention in this capacity can be found, for example, in WO 05/023792.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The contents of all references, patents, and patent applications cited throughout this application are hereby incorporated by reference.

EXEMPLIFICATION

The following naming conventions are used herein:

| | |
|---|---|
| TMS | trimethylsilyl |
| TMSCL | trimethylsilyl chloride |
| TBDMS | t-butyl dimethyl silyl |
| TIPS | triisopropylsilyl |
| TBAF | tetrabutyl ammonium fluoride |
| TMSI | iodotrimethylsilane |
| PMP | p-methoxyphenyl |
| -OTf | triflate |
| BOC | t-butyl carbamate |
| MPM | 4-methoxybenzyl |
| PCC | pyridinium chlorochromate |
| TBME | t-butyl methyl ether |
| TBDPS | t-butyl diphenyl ether |

| | |
|---|---|
| DMAP | dimethylaminopyridine |
| THF | tetrahydrofuran |
| IPA | isopropyl alcohol |
| TBAI | tetrabutyl ammonium iodide |
| KOtBu | potassium t-butoxide |
| DMSO | dimethyl sulfoxide |
| TBS | t-butyl dimethyl silyl |
| TFA | trifluoroacetic anhydride |
| KHMDS | potassium bis(trimethylsilyl)amide |
| DCM | dichloromethane |

Amounts of reagents given below are in relation to the first listed reagent for any given scheme. When volumes are given, they are calculated using the conversion factor of 1 kg of weight=1 L of volume.

Example 1

Synthesis of Compound 010

Scheme 3: Synthesis of diol from D-ribose

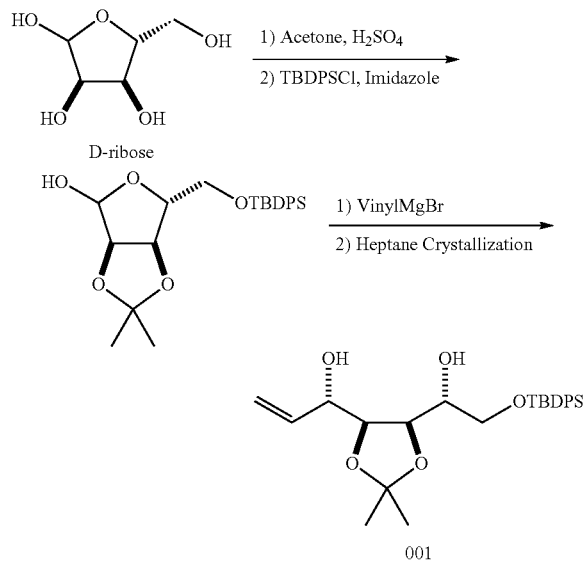

D-Ribose (1 wt) was suspended in acetone (5 volumes). Sulfuric acid (0.05 wts) was added and the mixture was stirred until homogeneous. Imidazole (0.6 wts) was added. The mixture was allowed to stir 15 minutes, and then the acetone was distilled off. Acetone (0.5 vol) was charged in to the reactor. The acetone was distilled off and the procedure was repeated. Dichloromethane (0.5 vol) was charged into the reactor and distilled off. The material was taken on crude to the next reaction.

To the acetonide (1 wts) was added imidazole (0.36 wts). The mixture was suspended in dichloromethane (5 vols) at 25° C. The mixture was cooled to 0° C. and tert-butyldiphenylsilyl chloride (1.4 wts) was added. A saturated solution of ammonium chloride (2 vols) and water (1 vol) was added and the mixture stirred 15 minutes. TBME (2.5 vols) was added to the organic solution and stirred 5 minutes. The organic solution was separated and washed with water (2 vols) and brine (2 vols). The organic layer was concentrated and the crude TBDPS protected lactol was obtained. The material was taken crude to the next step.

To a solution of the TBDPS-acetonide (1 wts) in THF (1.6 vols) at −20° C. was added a solution of vinyl magnesium bromide (1 M/THF, 5.8 vols) at a rate keeping the temp below −10° C. The solution was allowed to slowly warm up to 25° C. The reaction was transferred to a cold mixture of saturated aqueous ammonium chloride (4.5 vols), TBME (4.5 vols) and water (1.8 vol). The aqueous layer was separated and the organic solution was washed twice with water (2.25 vols). The organic solution was washed with brine (4.5 vols) and concentrated. Crude diol 001 (35.2% yield from d-ribose) was crystallized from heptane. The solids were collected and washed with cold heptanes, and air dried.

Scheme 4: Synthesis of Acetate by Allylic Reduction

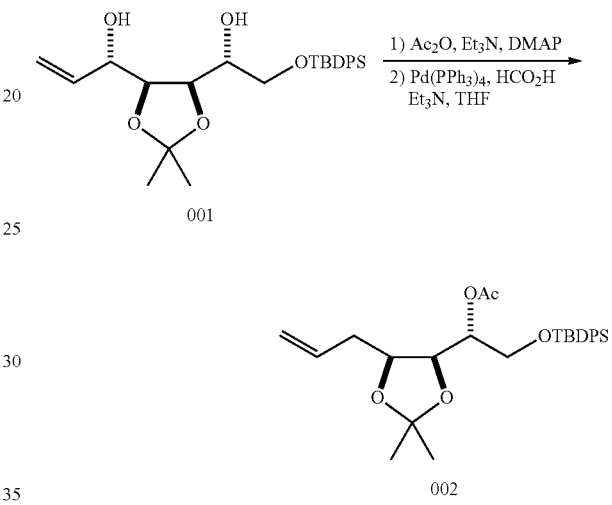

To a stirred solution of diol 001 (1 wts), dimethylaminopyridine (0.002 wts) and triethylamine (0.76 vols) in tert-butyl methyl ether (1.75 vols) at 0° C. was added acetic anhydride (0.46 vols). The solution was allowed to warm to 25° C. and was then stirred for about 1 h. The reaction mixture was cooled to 0° C. and quenched with saturated aqueous ammonium chloride (2 vols). TBME (1 vols) was added. The organic phase was separated and washed with water (2 vols) followed by brine (2 vols). The combined organic solution was concentrated to afford diacetate which was used without further purification.

Figure 3A:
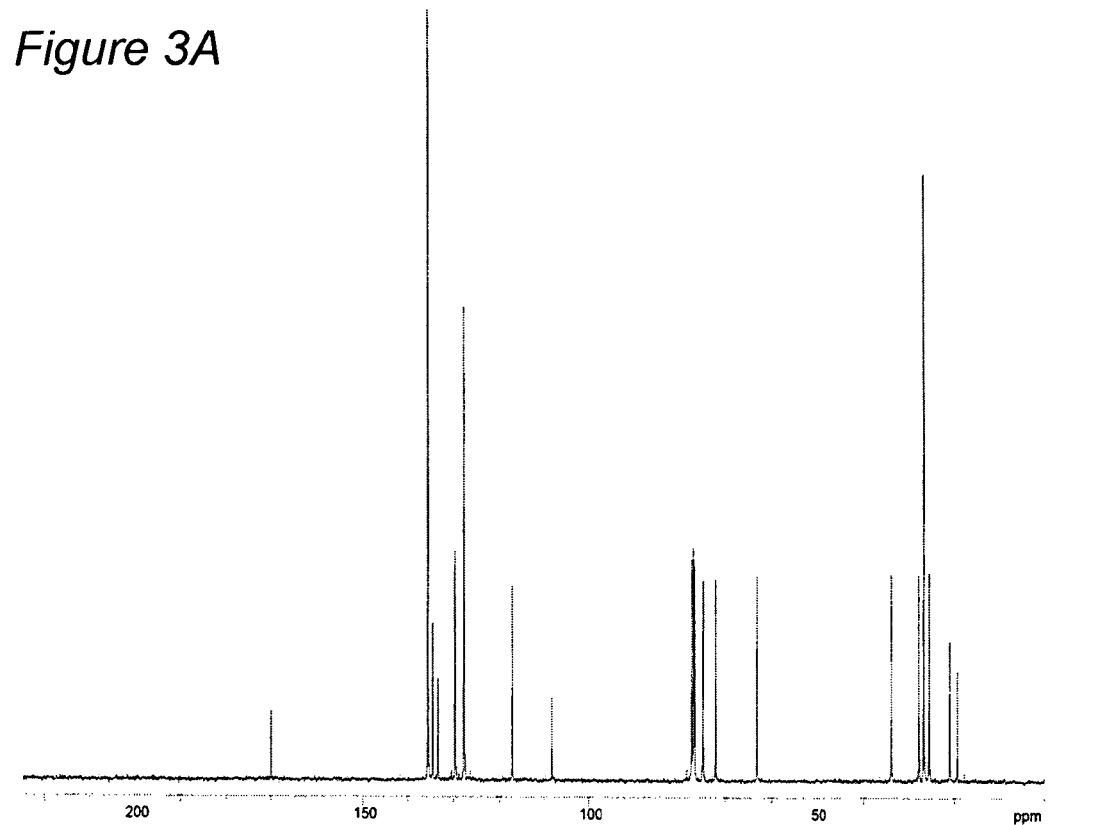
FIGS. 3-12 are 100 MHz $^{13}$C NMR (A) and 400 MHz $^1$H NMR (B) spectra of exemplary intermediates and an exemplary final product of the present invention in CDCl$_3$.
Figure 3B:
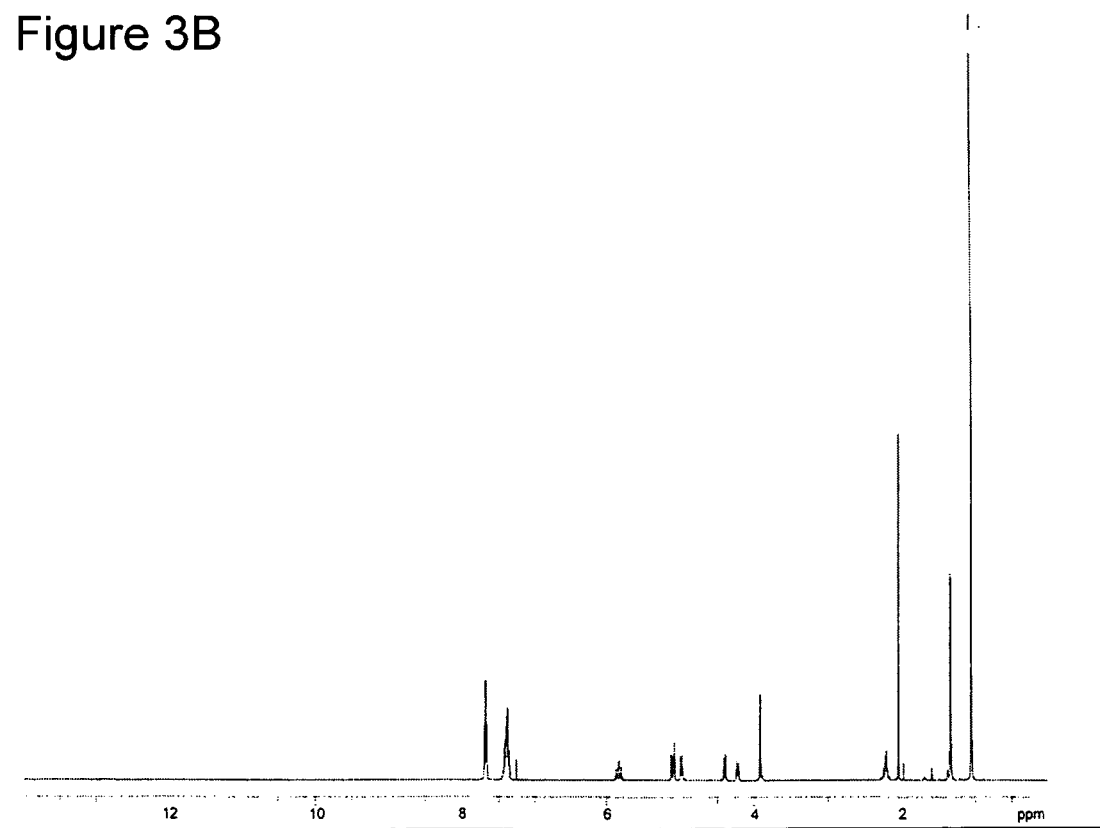

A reactor was charged with catalyst Pd(Ph$_3$P)$_4$ (0.02 wts), triethylamine (0.37 wts) and THF (3 vols). The solution was cooled to 5° C. Formic acid (0.17 vols) was then added. After the addition of formic acid was completed, a solution of diacetate (1 wts) in THF (1 vols) was added. The mixture was heated to reflux (65° C.) for 2 hours. Upon completion, the mixture was cooled to 0° C. and quenched with water (1.82 vols). Tert-butyl methyl ether (2.73 vols) was added and stirred for 15 minutes. After separating the aqueous layer, the solution was washed with 10 wt % aqueous cysteine (2.0 vols) and then saturated sodium chloride (1.82 vols). The organic phase was concentrated. The crude oil residue was dissolved in IPA/water (9:1) (5 vols), warmed to 70° C. and then cooled to −5° C. The crystalline acetate 002 was filtered. The cake was washed with cold IPA/water (9:1) (0.5 vols) and then dried (64.8% yield from 001; M.P. 64-67° C.). $^{13}$C and $^1$H NMR of 002 are depicted in FIGS. 3A and 3B.

Scheme 5: Conversion of Acetate to Primary Alcohol

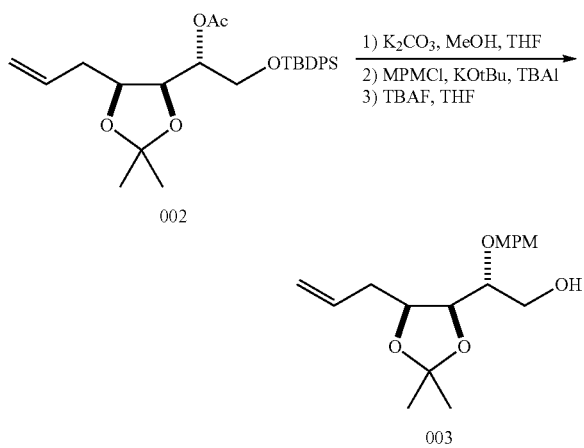

Acetate 002 (1 wt) was suspended in THF (4.7 vol) To the suspension was added MeOH (2.33 vol). To this resulting suspension was added a slurry of potassium carbonate (0.3 wts) in MeOH (2.33 vol). The mixture was cooled to 10° C. and then water (8.0 vol) and methyl tert-butyl ether (8 vol) were added. After agitation (15 minutes), the reaction was allowed to settle (15 minutes) and the organic layer was separated. The organic phase was then washed with brine (4 vol) and concentrated. The crude alcohol was used without purification.

The alcohol (1 wt.) was azeotroped with anhydrous THF (3×1.78 wts) until water levels were <0.03%. To the resulting oil was added a suspension of TBAI (0.17 wt) in DMF (1.05 wt). The mixture was then cooled to −15° C. The reactor was then charged with 20 wt % potassium tert-butoxide in THF (1.4 weights) diluted in anhydrous THF (0.94 wt). The mixture was stirred for 15 minutes. 4-methoxybenzyl chloride (0.43 wt) was then added. Upon completion, the reaction was quenched with a 0.5M solution of sodium methoxide in methanol (0.55 weight). The mixture was then allowed to stir at ambient temperature. The mixture was concentrated and the remaining oil was partitioned between water (5 weights) and tert-butyl methyl ether (3.7 weights). The organic layer was washed with saturated aqueous sodium chloride and was then concentrated. The crude oil was used with purification.

The silyl ether (1.0 wt) was dissolved in THF (2.3 weights). Tetrabutylammonium fluoride (1.0 M in THF) (1.9 wts) was added. Upon completion, 10% aqueous sodium bicarbonate (2.6 wts) was added and the mixture was extracted twice with tert-butyl methyl ether (1.9 wts). The combined organic layers were washed with saturated aqueous sodium chloride (2.6 wts). The organic layer was then concentrated to provide crude 003.

Figure 4A:
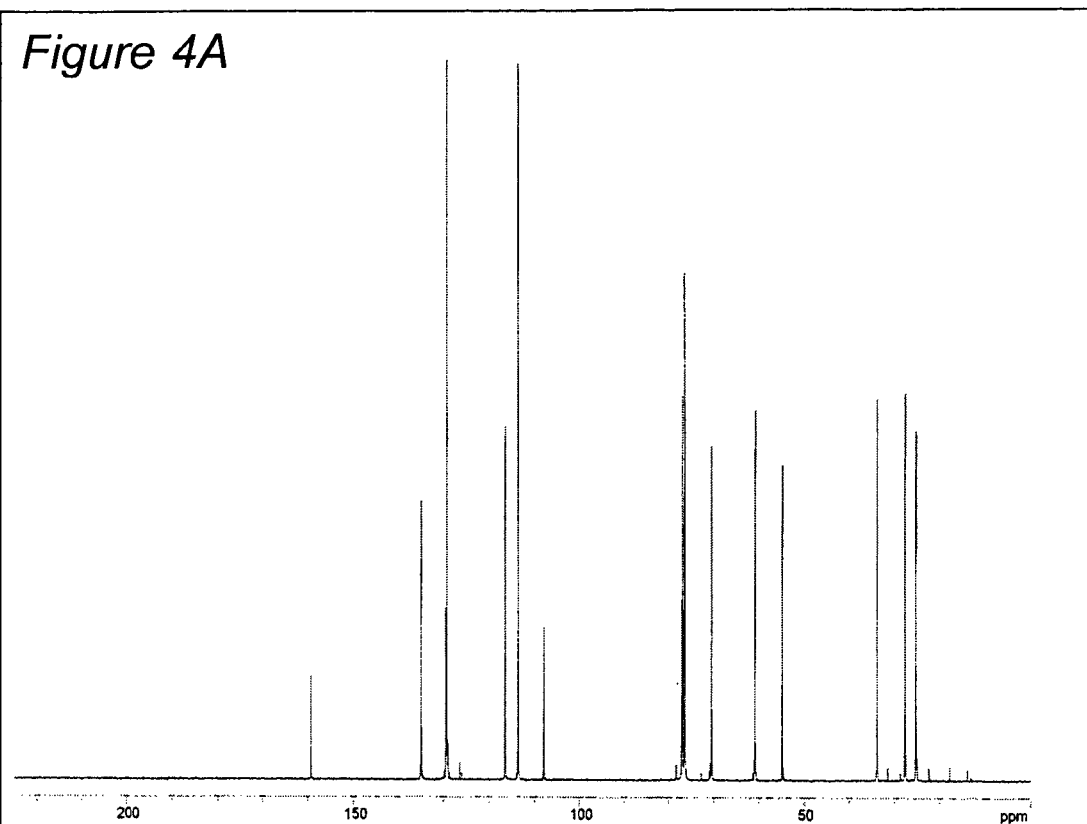
Figure 4B:
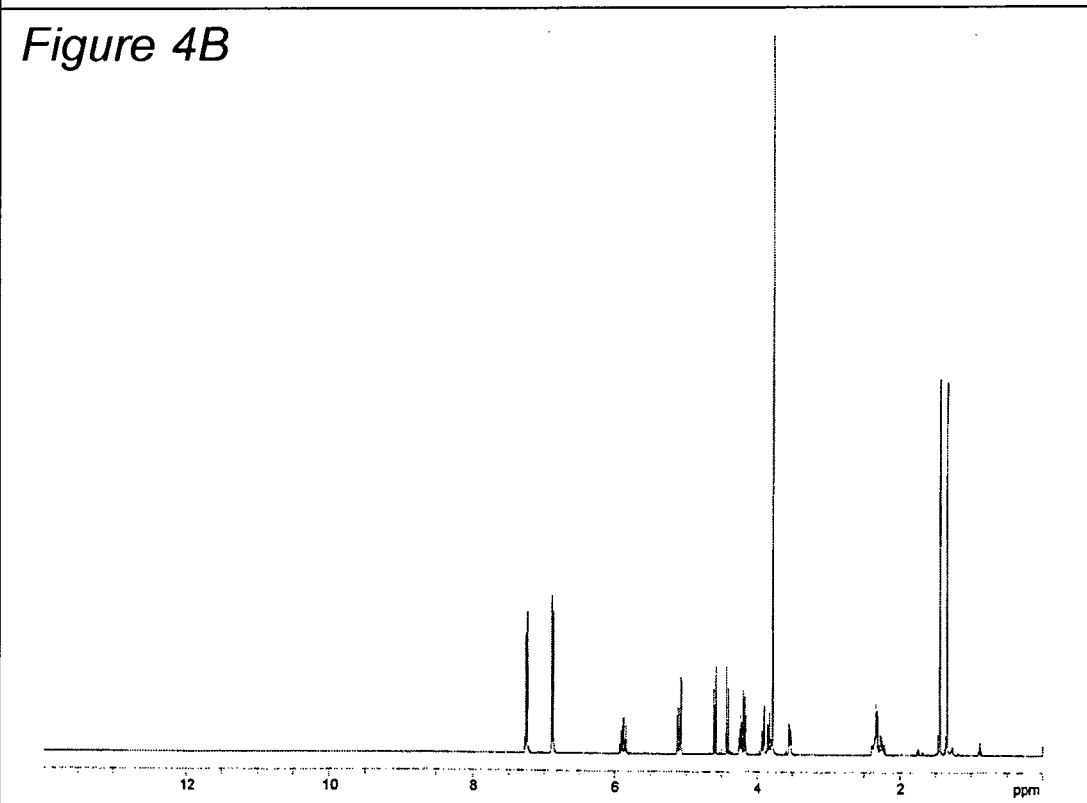

To the crude 003 (1.0 wt based on theoretical mass) was added TBME (2.95 wts), DMAP (0.04 wts), triethylamine (0.31 wts), and phthalic anhydride (0.69 wts). Upon completion compound 003a was extracted with 3% aqueous NaHCO$_3$ (9.98 weights). The combined aqueous sodium bicarbonate extractions were returned to the reactor and then washed twice with heptane (2.27 wts). Sodium hydroxide (1.23 wts) was then added. Upon conversion back to compound 003, the aqueous layer was extracted with TBME (2.73 wts). The TBME organic layers were then concentrated yielding a yellow orange oil of compound 003 (66.2% yield from 002). $^{13}$C and $^1$H NMR of 003 are depicted in FIGS. 4A and 4B.

Scheme 6: SO$_3$-pyridine oxidation

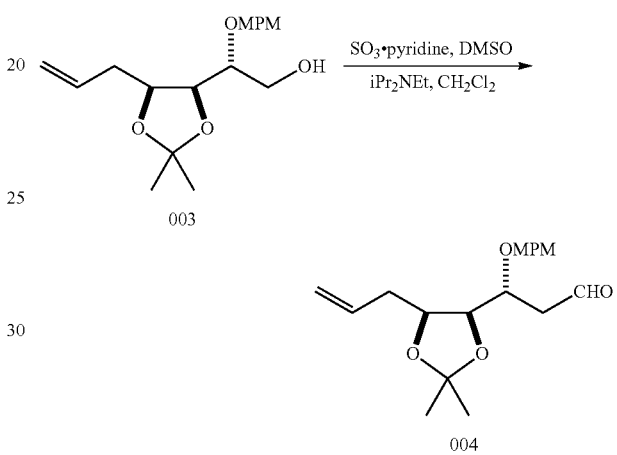

Primary alcohol 003 (1 wt.) was dissolved in anhydrous dichloromethane (5.0 vol.). The solution was cooled to 0° C., and then diisopropylethylamine (1.38 vol.) was added. Sulfur trioxide pyridine complex (1.29 wt.) was dissolved in anhydrous dimethylsulfoxide (5.00 vol.) in a separate reactor. The SO$_3$Py/DMSO solution was added alcohol/CH$_2$Cl$_2$ solution. Upon completion, the reaction mixture was quenched with cold water (6.4 vol.). The organic layer was separated. The aqueous phase was extracted with a mixture of heptane (4.50 vol.) and dichloromethane (0.30 vol.). The combined organic phases were washed with 5 wt % aqueous citric acid (5.0 vol.) until the pH value of the aqueous layer was <3. The organic phase was washed with 10 wt % aqueous sodium bicarbonate (2.50 vol.), and then saturated aqueous sodium chloride (4.80 vol.). The organic phase was concentrated and dried by azeotroping with heptane (2×4.0 vol.), providing aldehyde 004.

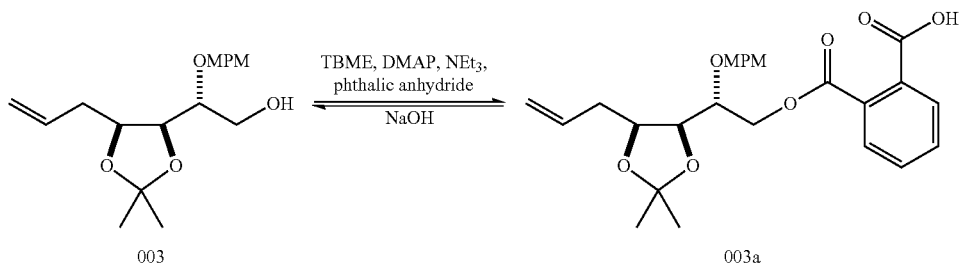

Scheme 7: Synthesis of Alcohol and Phosphonium Salt from Ethyl 3-(S)-hydroxybutyrate

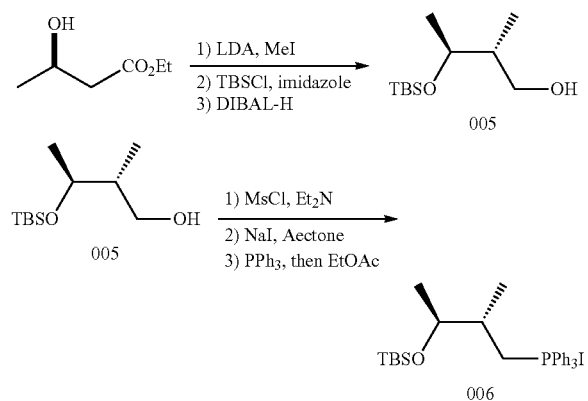

Ethyl 3-(S)-hydroxybutyrate (1 wt.) was added to a solution of 2.0 M lithium diisopropylamide (10 wt.) at 0° C. The mixture was stirred for 30 minutes, and then was cooled to −20° C. A solution of methyl iodide (1.8 wt.) in THF (3.4 wt) was added while maintaining a reaction temperature below −15° C. Upon completion, the reaction was quenched with saturated aqueous ammonium chloride (8 vol.). The mixture was extracted twice with ethyl acetate (6 vol. each). The combined ethyl acetate layers were washed twice with saturated aqueous sodium chloride (6 vol. each), then concentrated under reduced pressure. The crude mixture was dried by azeotroping with heptane and used directly in the next reaction.

The crude material (1 wt) was dissolved in anhydrous DMF (3.7 wt.). Imidazole (0.77 wt) and tert-butyldimethylsilyl chloride (1.25 wt) were added. Upon completion, the reaction was quenched with water (4 wt.) and extracted twice with heptane (4 wt. each). The heptane layers were concentrated under reduced pressure, then solvent exchanged to toluene and used directly in the next reaction.

The crude ester (1.0 wt) was dissolved in anhydrous toluene (1.22 wt.) and the solution was cooled to −10° C. A solution of diisobutylaluminum hydride in toluene (4.5 wt) was added maintaining a reaction temperature below 0° C. Upon reaction completion, methanol (0.4 wt) was added. The reaction mixture was transferred into a solution of cold aqueous hydrochloric acid (6.0 wt). The mixture was extracted twice with methyl tert-butyl ether (2.3 wt. each). The combined organic layers were concentrated under reduced pressure. The crude product 005 (68.7% yield from Ethyl 3-(S)-hydroxybutyrate starting material) was then purified by vacuum distillation (100-120° C. at 10 torr).

The alcohol 005 (1.0 wt) was dissolved in THF (3 wt) and cooled to 0° C. Triethylamine (0.51 wt) was added followed by methanesulfonyl chloride (0.55 wt.). Upon completion of the reaction, water (2.5 wt) was added followed by heptane (3.5 wt.). After phase separation, the heptane layer was washed with saturated sodium chloride (2.5 wt) and then concentrated under reduced pressure. The crude material was used directly in the next reaction.

The mesylate (1.0 wt) was dissolved in acetone (3.33 wt). Sodium iodide (1.0 wt) was added and the mixture was heated to reflux. Upon completion, the reaction was cooled to ambient temperature and water (2.8 wt) was added. The mixture was extracted with heptane (4.0 vol). The heptane layer was washed consecutively with saturated aqueous sodium bicarbonate (1 wt), saturated aqueous sodium thiosulfate (2.5 wt) and saturated aqueous sodium chloride (2.0 wt). The heptane layer was concentrated under reduced pressure and used directly in the next reaction.

Figure 5A:
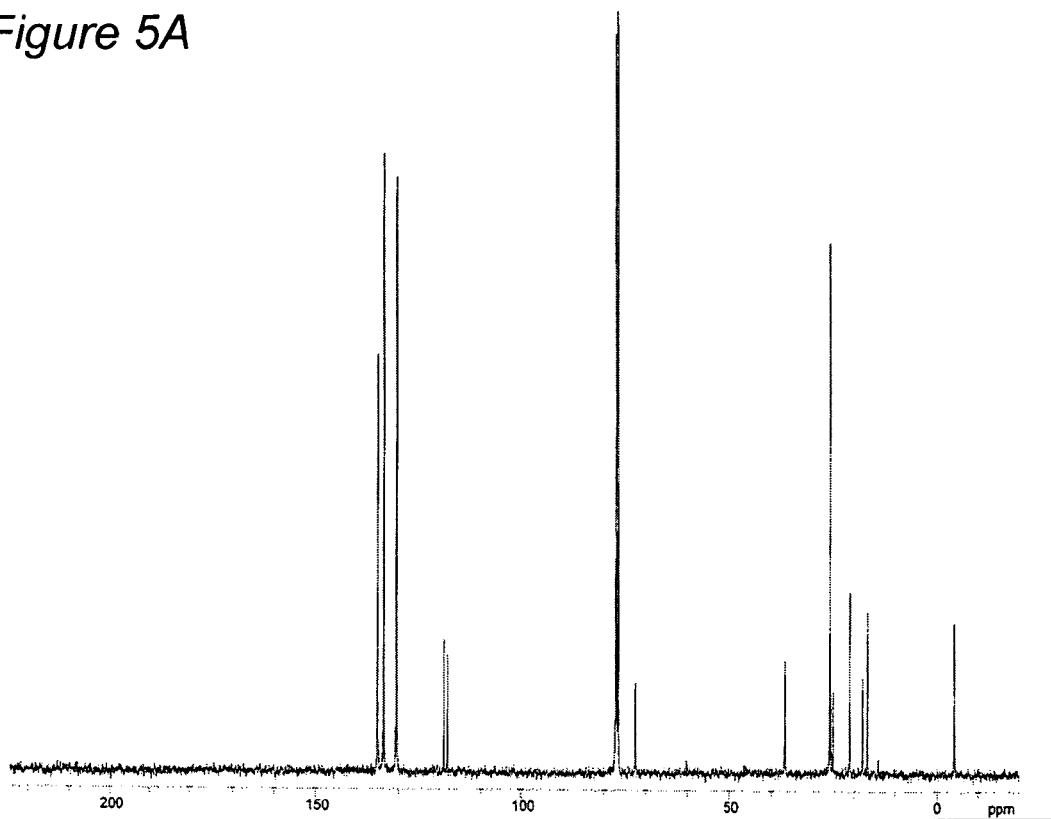
Figure 5B:
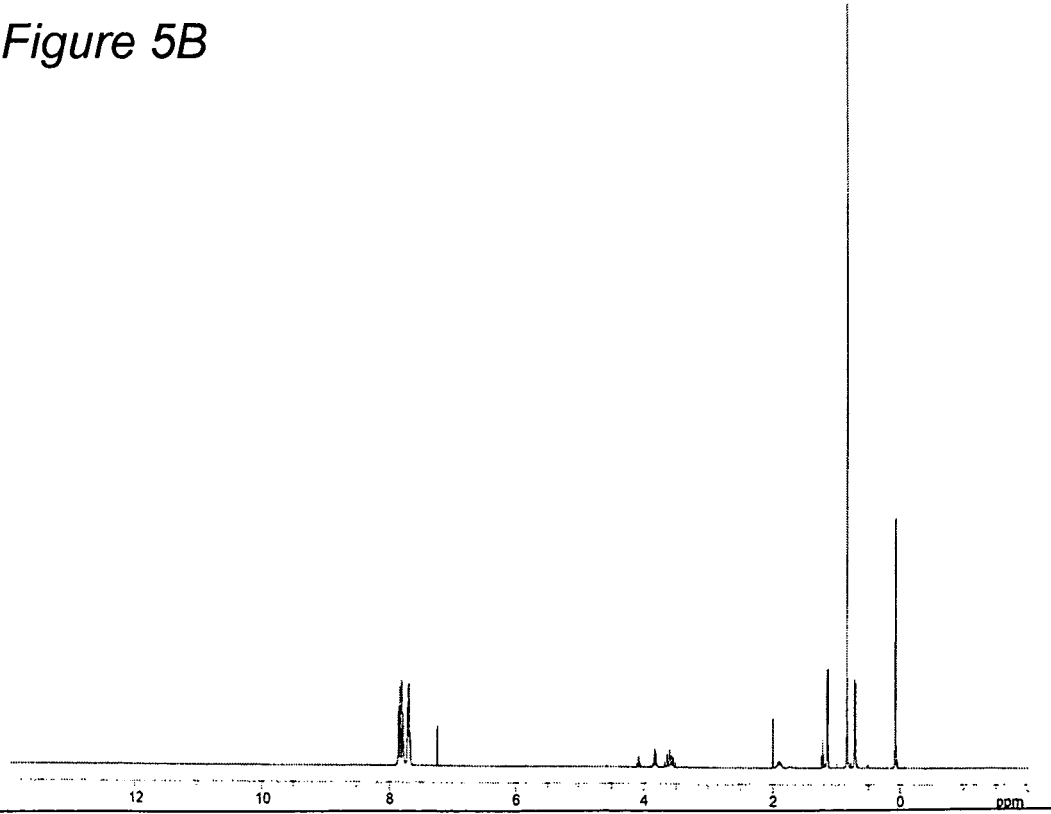

Triphenylphosphine (3.0 wt.) was heated to 100° C. The iodide (1.0 wt) was added and the mixture was stirred at 100° C. until the iodide was consumed. Ethyl acetate (5 wt) was added and the mixture was maintained at reflux for 20 minutes, and then cooled to 0° C. The resulting solid phosphonium salt 006 (72.4% yield from 005) was filtered, rinsed with additional ethyl acetate (7 vol) and then dried under nitrogen. $^{13}C$ and $^1H$ NMR of 006 are depicted in FIGS. 5A and 5B.

Scheme 9: Wittig Coupling

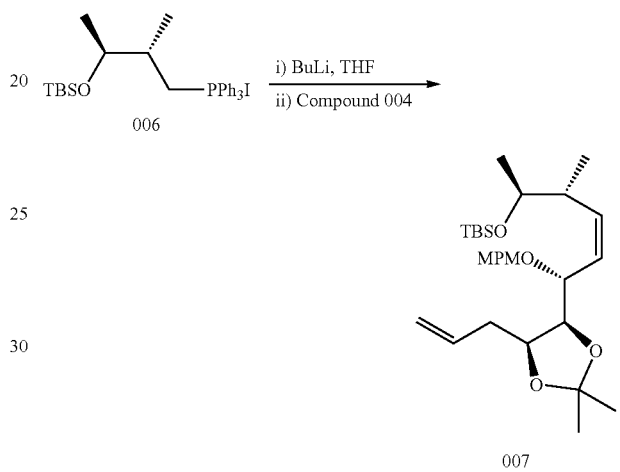

Figure 6A:
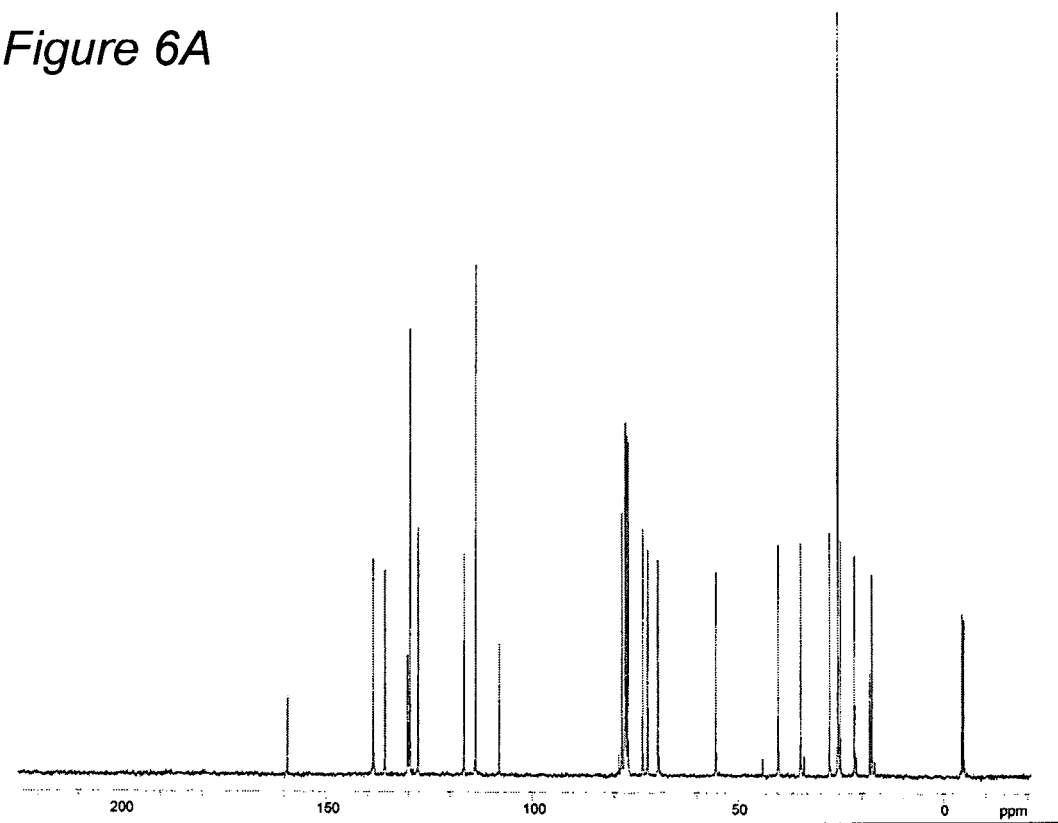
Figure 6B:
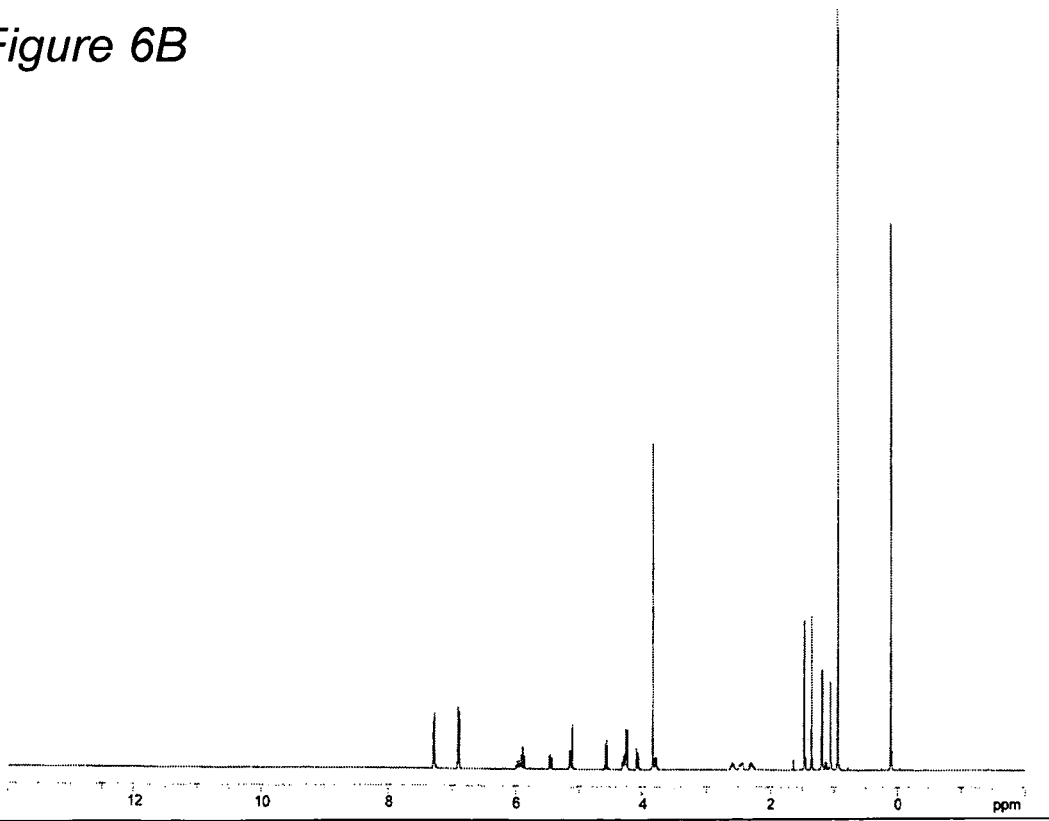

Phosphonium salt 006 (2.40 wts) was dried by azeotroping with anhydrous THF (9.60 vol.). Anhydrous THF was added (4.80 vol) and the mixture was cooled to 0° C. 1.6 M n-butyl lithium (2.42 vol.) was added, and the solution was stirred for 20 min. A solution of aldehyde 004 (1 wt.) in anhydrous THF (1 vol.) was added to the reaction mixture and the reaction was warmed to 20° C. Upon completion, Celite (1.3 wt.) was added followed by a solution of citric acid/D.I. water (0.13 wt./0.15 vol.). Heptane (3.90 vol.) was added and the mixture was filtered and washed with heptane (2×5.23 vol.). The combined filtrates were concentrated. Heptane (3.78 vol.) was added and the solution was filtered, rinsing with heptane (2×3.78 vol.). The combined filtrates were concentrated and the crude material was used without purification. $^{13}C$ and $^1H$ NMR of 007 are depicted in FIGS. 6A and 6B.

Scheme 10: Heck Reaction

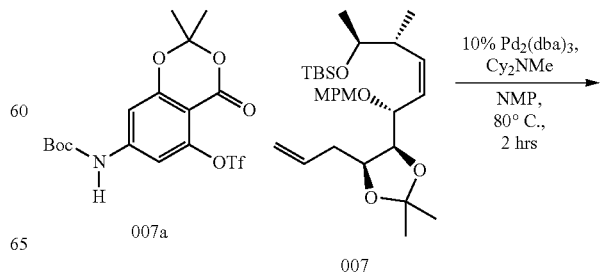

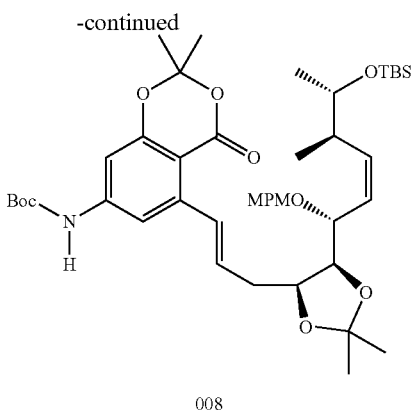

008

The triflate 007a (1.1 wt), olefin 007 (1.0 wt), and tris(dibenzylideneacetone)-dipalladium were combined in a reactor. N-methylpyrrolidinone (3.3 vol) and dicyclohexylmethylamine (0.77 wt) were added. The mixture was stirred at 80° C. Upon completion, the mixture was cooled to 20° C., and Celite (1.5 wt) and ethyl acetate (10 vol) were added. The mixture was filtered and the solids rinsed with ethyl acetate (30 vol). The filtrates were concentrated under reduced pressure. The crude concentrate was purified by silica gel chromatography, which afforded a 72.5% yield.

Scheme 11: Macrolactonization

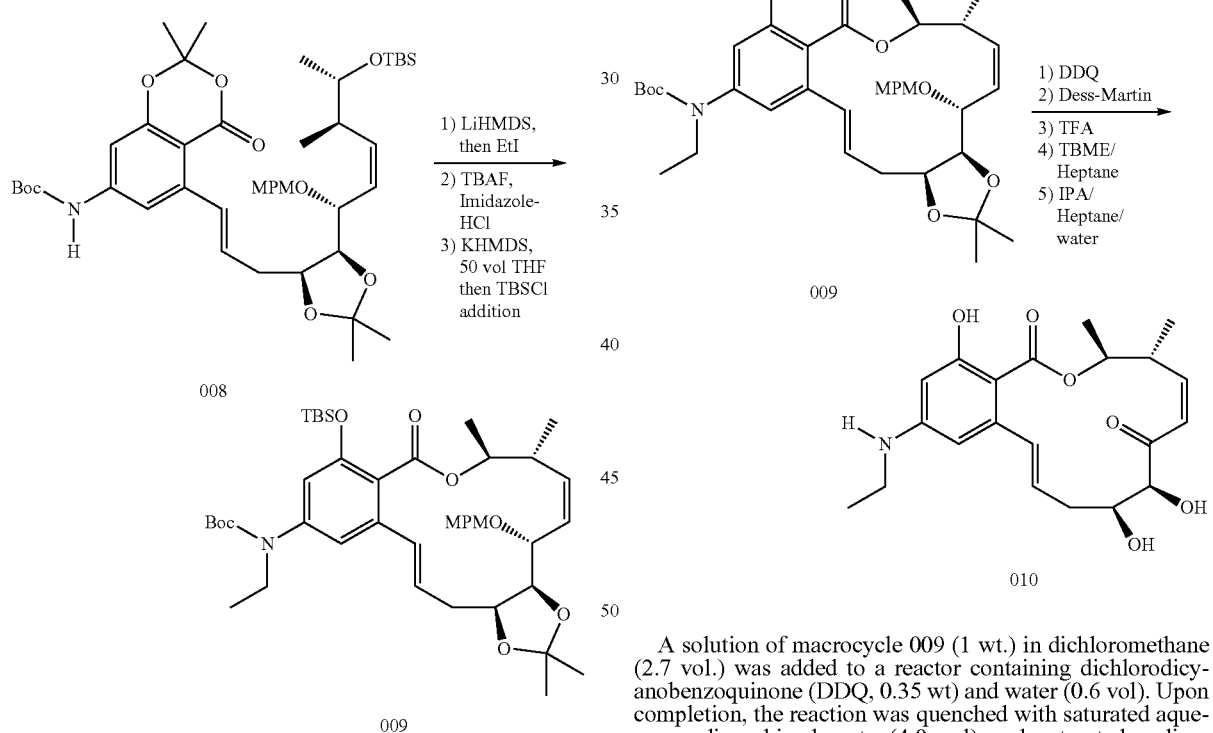

The Boc-amide 008 was dissolved in dimethyltetrahydropyrimidinone and cooled to 0° C. A 1.0 M solution of lithium bis(trimethylsilylamide) in THF (2.5 vol) was added. Iodoethane (1.2 wt) was added, then the mixture was warmed to 0° C. Upon completion, the mixture was cooled to 0° C. and was quenched with saturated aqueous ammonium chloride (25 vol). The mixture was extracted three times with a mixture of heptane (4.0 vol) and methyl tert-butyl ether (4.0 vol). The combined organic layers were washed with saturated aqueous sodium chloride (25 vol) and then concentrated under reduced pressure. The crude silyl ether concentrate was purified by silica gel chromatography, which afforded a 94% yield.

Imidazole hydrochloride (0.44 wt) was dissolved in 1.0 M tetrabutylammonium fluoride in THF (8.5 vol). A solution of the silyl ether (1.0 wt) in THF (4.8 vol) was added. Upon completion, the mixture was quenched with saturated aqueous ammonium chloride (15.0 vol) and extracted three times with methyl tert-butyl ether (10 vol each). The combined organic layers were washed with water (33 vol) and saturated aqueous sodium chloride (33 vol), and then concentrated under reduced pressure. The crude alcohol concentrate was purified by silica gel chromatography, which afforded a 51.6% yield.

Figure 7A:
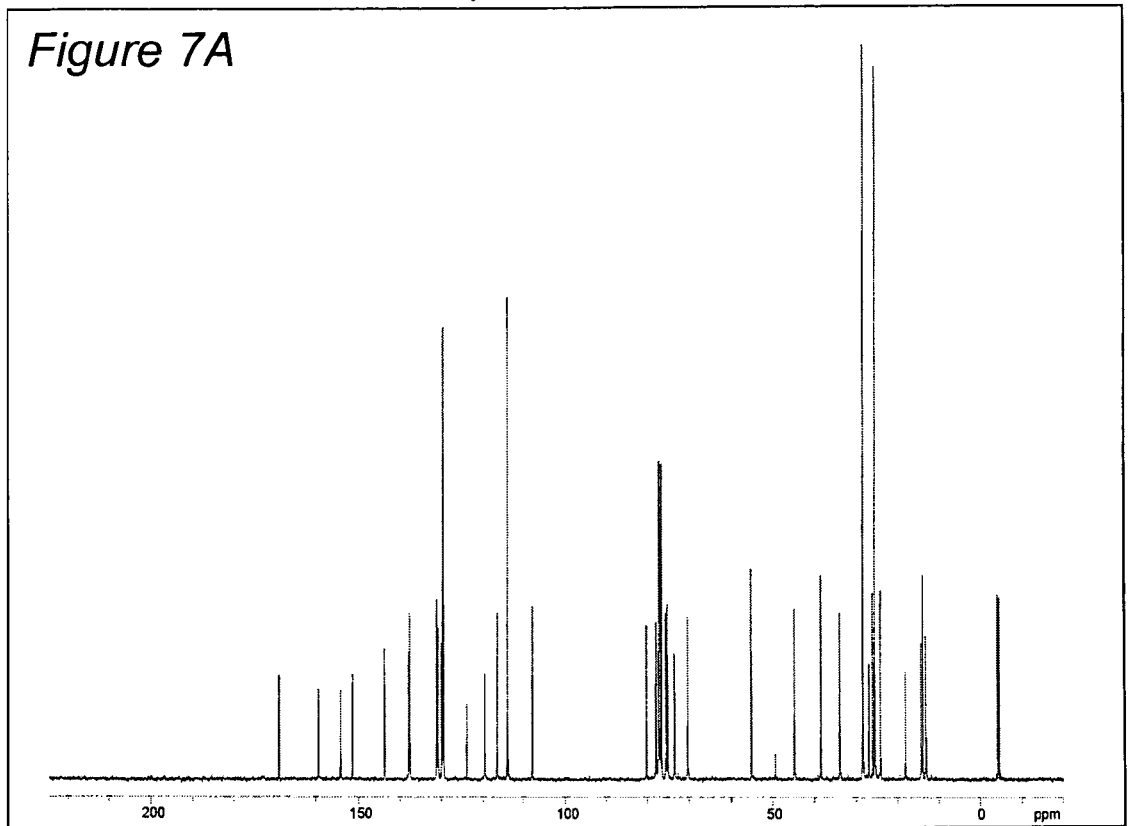
Figure 7B:
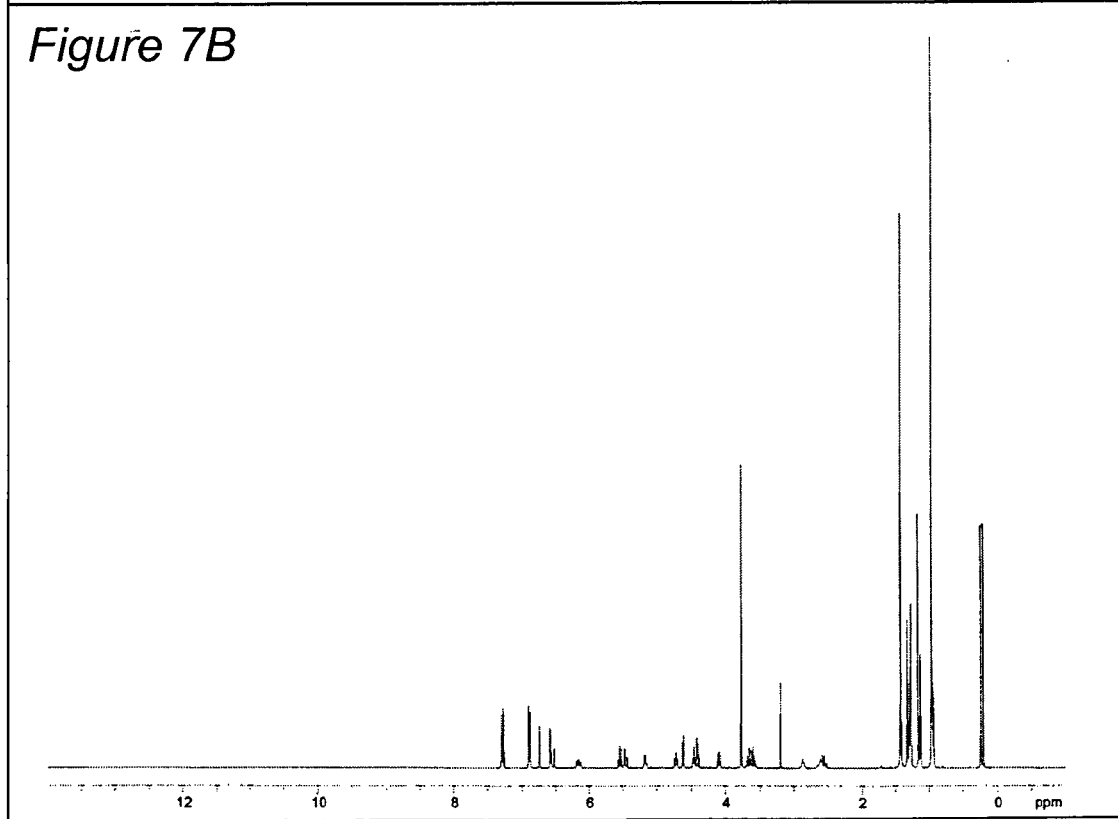

The alcohol (1.0 wt) was dissolved in THF (47 vol) and the solution was cooled to 0° C. A 0.5 M solution of potassium bis(trimethylsilyl)amide (3.0 vol) was added over a 3 hour period. Upon completion, a solution of tert-butyldimethylsilyl chloride (1.0 wt) in THF (1.0 vol) was added. Upon completion, saturated aqueous ammonium chloride (25 vol) and water (4 vol) were added. The mixture was extracted with tert-butyl methyl ether (25 vol). After removal of the aqueous layer, the organic layer was washed with saturated aqueous sodium chloride (25 vol). The combined organic layer was concentrated under reduced pressure. The crude concentrate was purified by silica gel chromatography, providing compound 009 (57.4% yield). $^{13}C$ and $^1H$ NMR of 009 are depicted in FIGS. 7A and 7B.

Scheme 12: Compound 010

A solution of macrocycle 009 (1 wt.) in dichloromethane (2.7 vol.) was added to a reactor containing dichlorodicyanobenzoquinone (DDQ, 0.35 wt) and water (0.6 vol). Upon completion, the reaction was quenched with saturated aqueous sodium bicarbonate (4.0 vol) and saturated sodium thiosulfate (1 vol). After phase separation, the aqueous layer was extracted with a mixture of ethyl acetate (1.3 vol) and heptane (2.6 vol). The combined organic layers were concentrated under reduced pressure. The crude concentrate was dissolved in ethyl acetate (1.6 vol) and the solution was added to a solution of semicarbazide hydrochloride (0.22 wt) and sodium acetate (0.54 wt) in water (0.96 vol). Upon completion, the solids were filtered and rinsed with ethyl acetate (3.34 vol). The aqueous phase was removed from the filtrates and the organic layer was concentrated under reduced pressure. The concentrate was dissolved in a mixture of heptane (2 vol) and dichloromethane (2.0 vol), polish filtered, and concentrated under reduced pressure, providing the allylic alcohol.

The allylic alcohol (1.0 wt) was dissolved in dichloromethane (4.0 vol). Dess-Martin periodinane (0.68 wt.) was added portionwise. Upon completion, the reaction was quenched with saturated aqueous sodium bicarbonate (7.0 vol.). A solution of 10 wt % aqueous sodium thiosulfate (5.5 vol.) was added. The organic phase was separated and the aqueous layer was extracted with a mixture of ethyl acetate (2.2 vol) and heptane (2.2 vol). The combined organic phases were concentrated under reduced pressure. The concentrate was dissolved in ethyl acetate (4.5 vol.), and was washed with saturated aqueous sodium chloride (1.5 vol.). The organic phase was concentrated under reduced pressure, providing the enone.

Figure 8A:
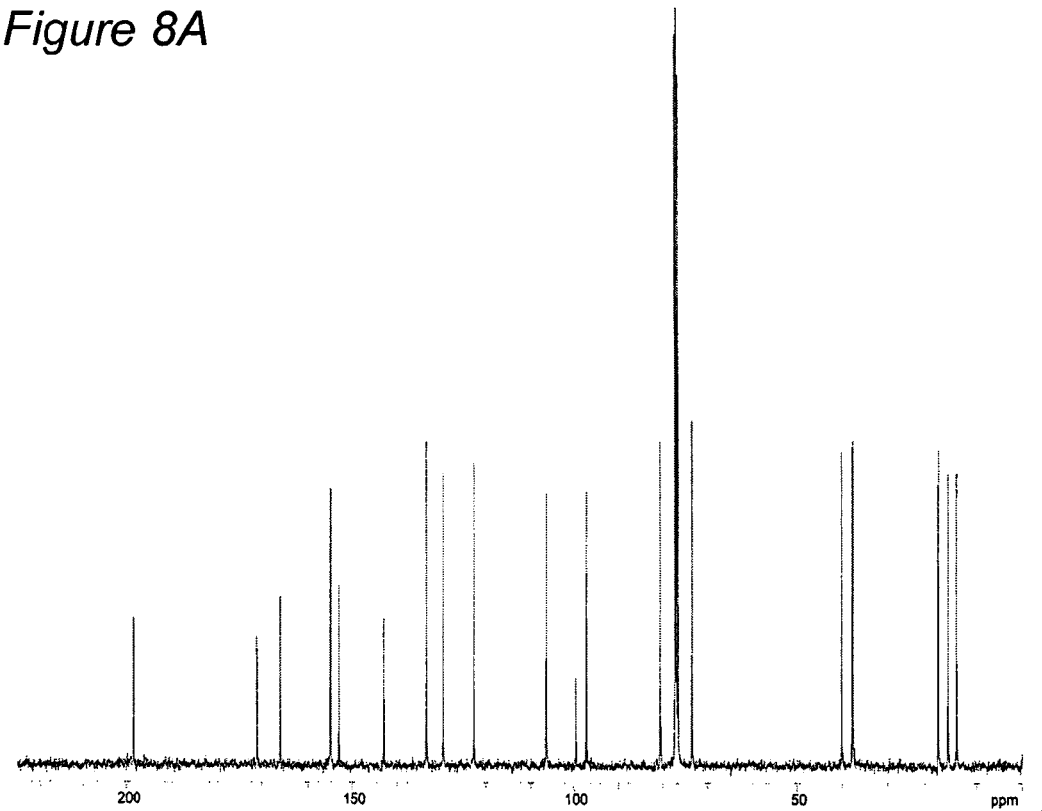
Figure 8B:
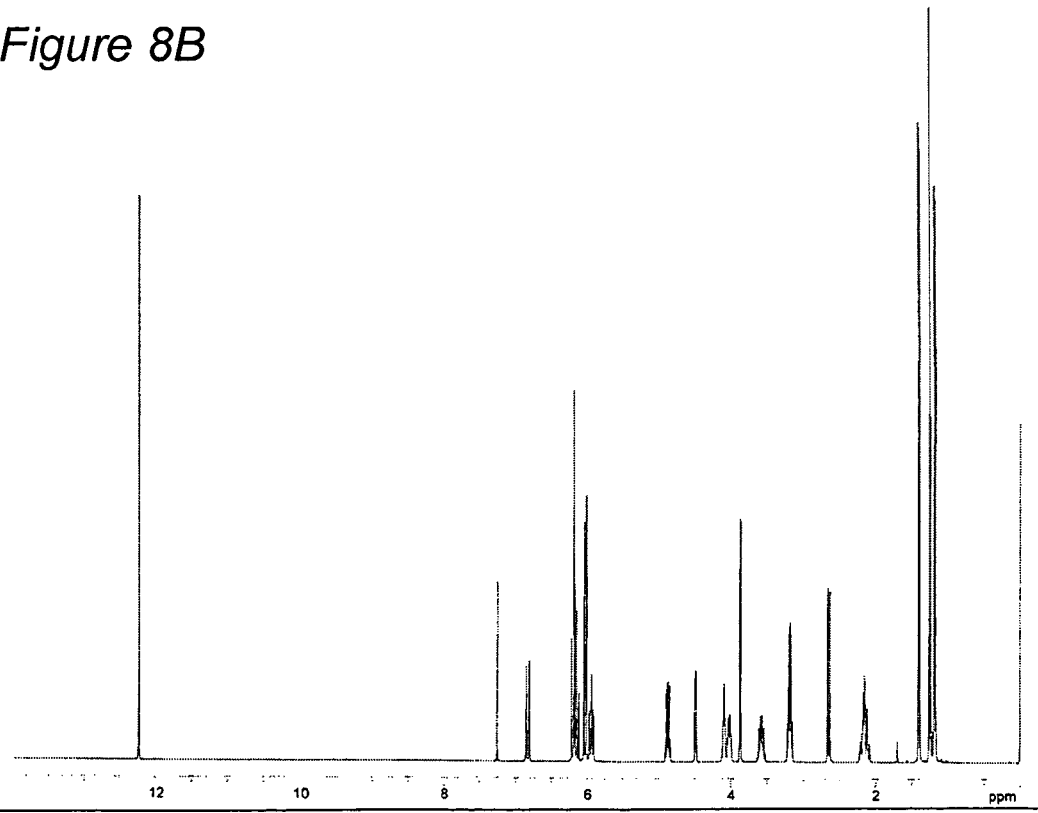

A solution of the enone (1.0 wt) in dichloromethane (6.5 vol) was added to a 0° C. solution of trifluoroacetic acid (6.1 vol) in water (0.3 vol). Upon completion, the reaction was quenched with chilled (0° C.) 15.0% aqueous ammonium hydroxide (11.0 vol). After separation of the organic layer, the aqueous layer was extracted with dichloromethane (2.3 vol). The combined organic layers were washed with saturated sodium chloride (4.6 vol). The organic phase was concentrated under reduced pressure. t-Butyl methyl ether (2.2 vol) was added and the mixture was warmed to 55° C. Heptane (2.2 vol) was gradually added, then the solution was cooled to 0° C. The solids were filtered and washed with a 0° C. mixture of heptane (1.4 vol) and t-butyl methyl ether (1.4 vol). The solid 010 was dried and then suspended in 2-propanol (5.0 vol) and warmed to 65° C. Water (0.1 vol) was added followed by gradual addition of heptane (7.5 vol). The mixture was then cooled to 0° C. and the solids of 010 (80.7% yield from 009; M.P. 157-159° C.) were filtered, rinsed with a mixture of heptane (2.4 vol) and 2-propanol (2.4 vol), and then dried. $^{13}$C and $^1$H NMR of 010 are depicted in FIGS. 8A and 8B.

Example 2

Synthesis of Compound 010

Scheme 13: Oxidation followed Wittig Coupling

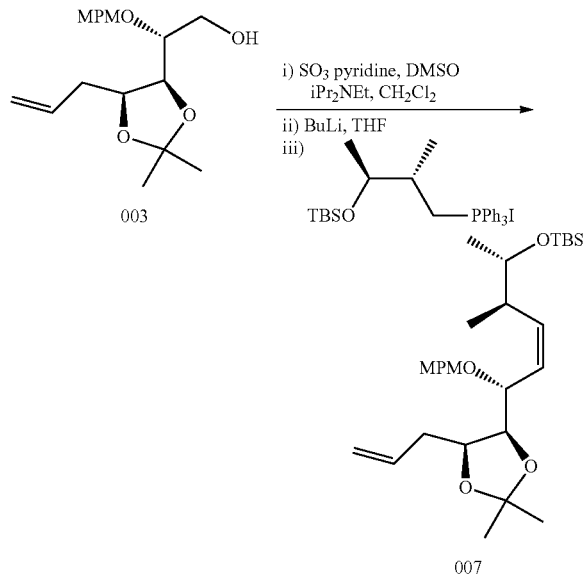

Compound 007 was synthesized from compound 003 as described above in Example 1.

Scheme 14: Crystalline intermediate 011.

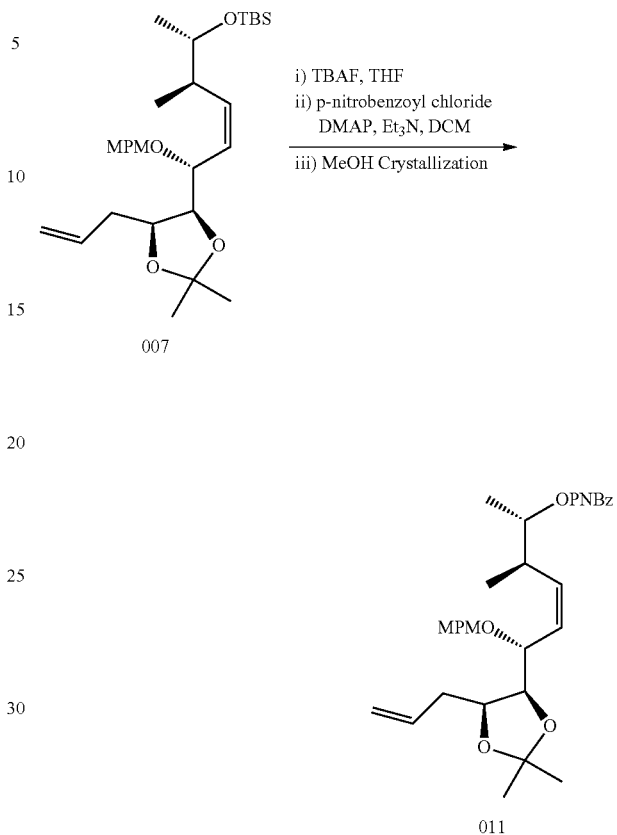

The TBS ether 007 (1 wt) was dissolved in THF (0.88 wt.). A 1.0 M solution of tetrabutylammonium fluoride in THF (2.1 wt.) was added. The solution was warmed to 50° C. Upon completion, the mixture was cooled to 20° C. 10 wt % aqueous sodium bicarbonate (3 vol) was added and the mixture was extracted with tert-butyl methyl ether (6 vol). The organic layer was washed with saturated aqueous sodium chloride (3 vol) and was then concentrated. The crude material was used without purification.

Figure 9A:
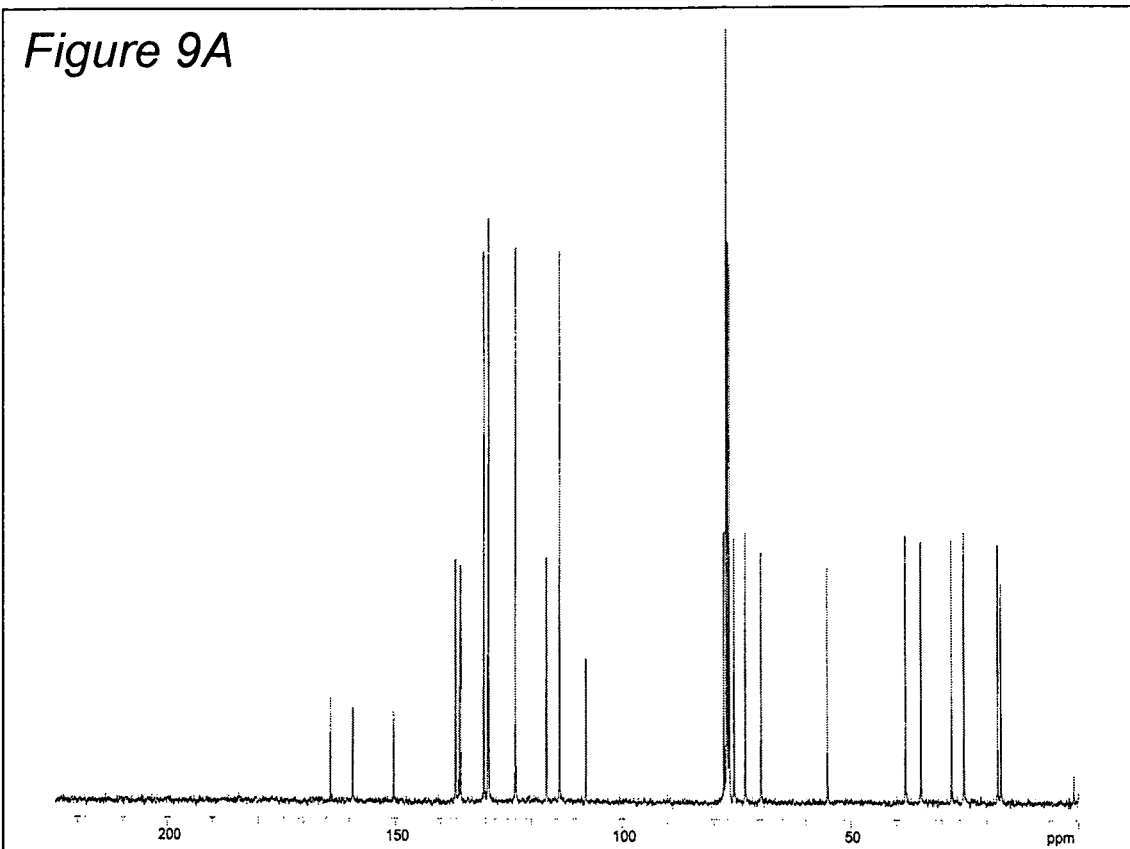
Figure 9B:
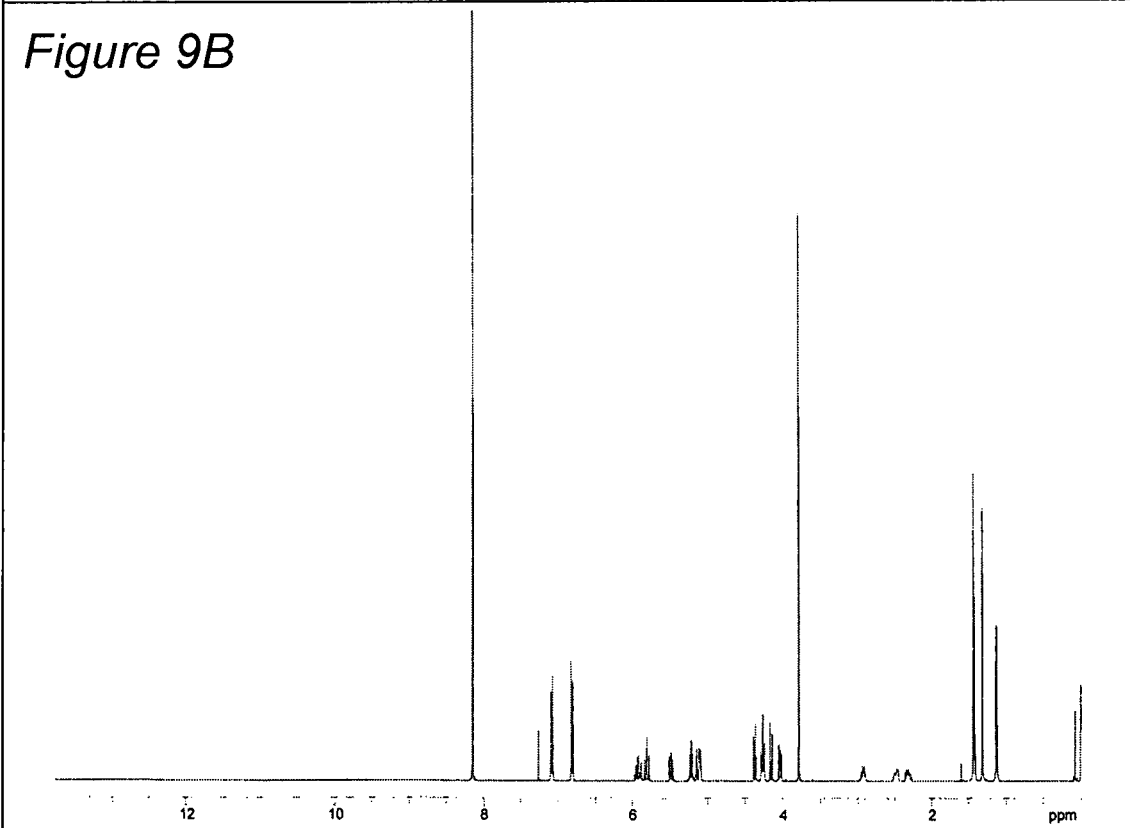

4-(dimethylamino)pyridine (0.03 wts) was added to a solution of the alcohol (1 wt) in anhydrous THF (9 vol.). Triethylamine (0.3 wts) was added and then 4-nitrobenzoyl chloride (0.5 wts) as a solution in THF (1.0 vol.). The reaction mixture was then stirred at 35° C. Upon completion, the reaction was cooled to 20° C. 5 wt % aqueous sodium bicarbonate (10 vol) was added followed by t-butyl methyl ether (15 vol). The organic phase was washed with 20 wt % aqueous sodium chloride (10 vol). The organic phase was concentrated and the solvent exchanged to methanol. Methanol (6 vol.) was added and the mixture was warmed to 50° C., followed by stirring at 50° C. for 30 minutes, and then cooling to 0° C. The crystalline solid (56.1% yield; M.P. 86-89° C.) was filtered, washed with cold methanol and dried. A single crystal of compound 011 was isolated, and the crystal structure is shown in FIG. 1. $^{13}$C and $^1$H NMR of 011 are depicted in FIGS. 9A and 9B.

Scheme 15: De-protection followed by Heck coupling

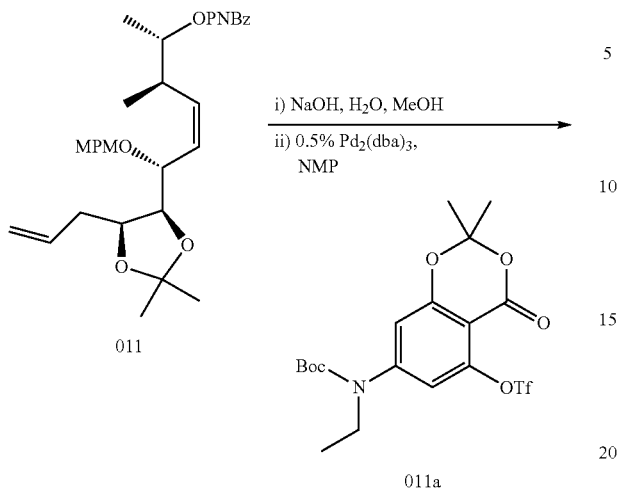

011

011a

Scheme 16: Macrolactonization

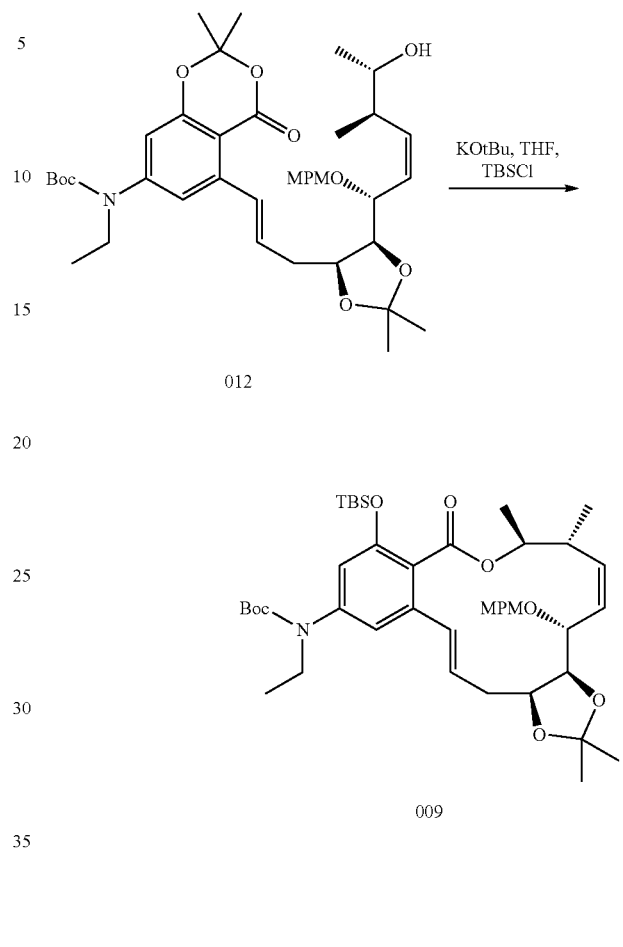

012

009

The p-nitrobenzoate ester 011 (1.0 wt.) was dissolved in THF (2.65 wt) and methanol (0.4 wt). A 10 wt % aqueous sodium hydroxide solution (1.65 wt) was added and the mixture was warmed to 35° C. Upon completion, the reaction was cooled to 20° C. Water (3.0 vol) was added followed by methyl tert-butyl ether (6 vol). After separation, the organic layer was washed with 25 wt % sodium chloride (4 vol). The solvent was removed under reduced pressure.

Figure 2:
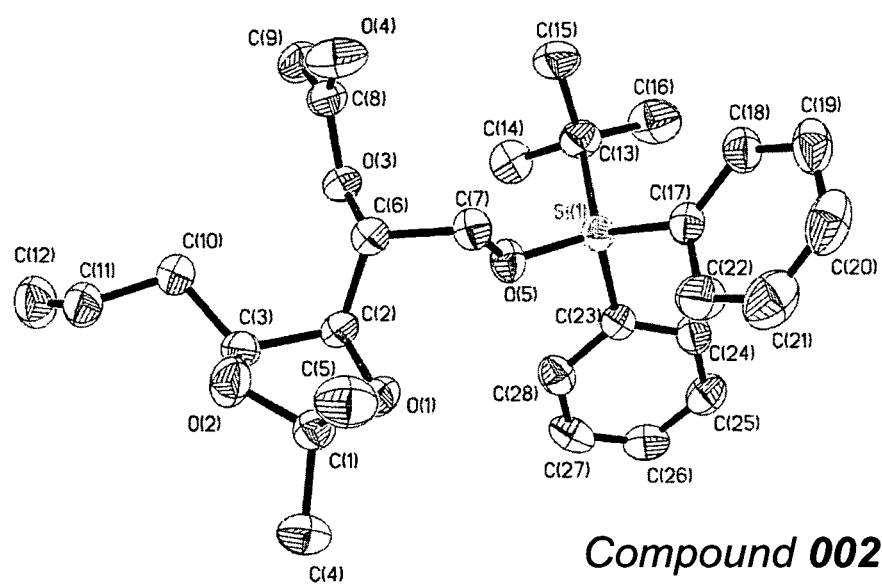
Figure 2:
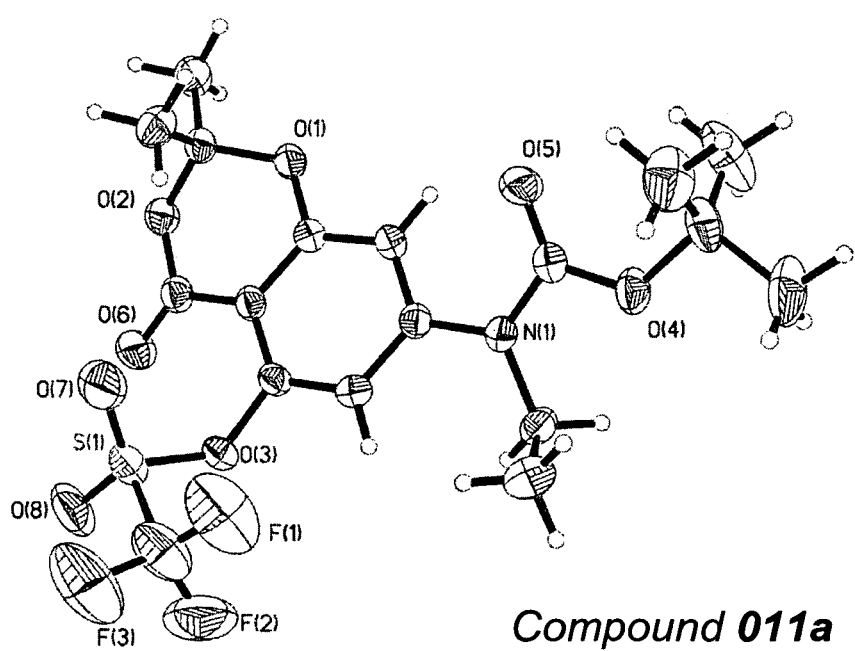
Figure 10A:
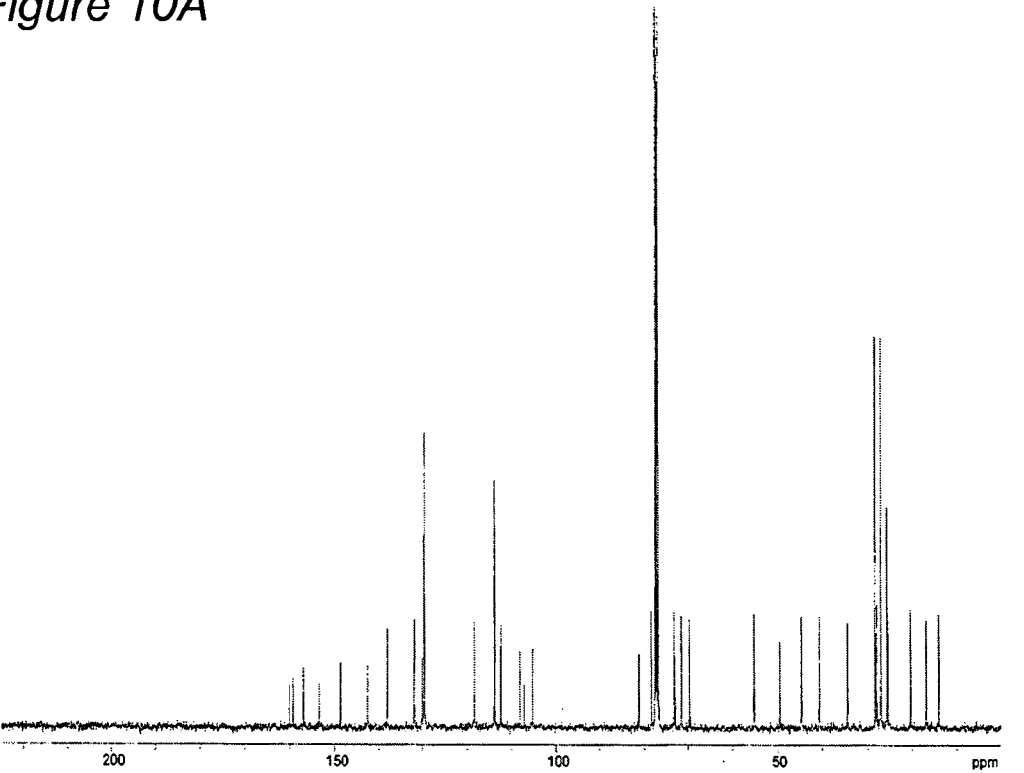
Figure 10B:
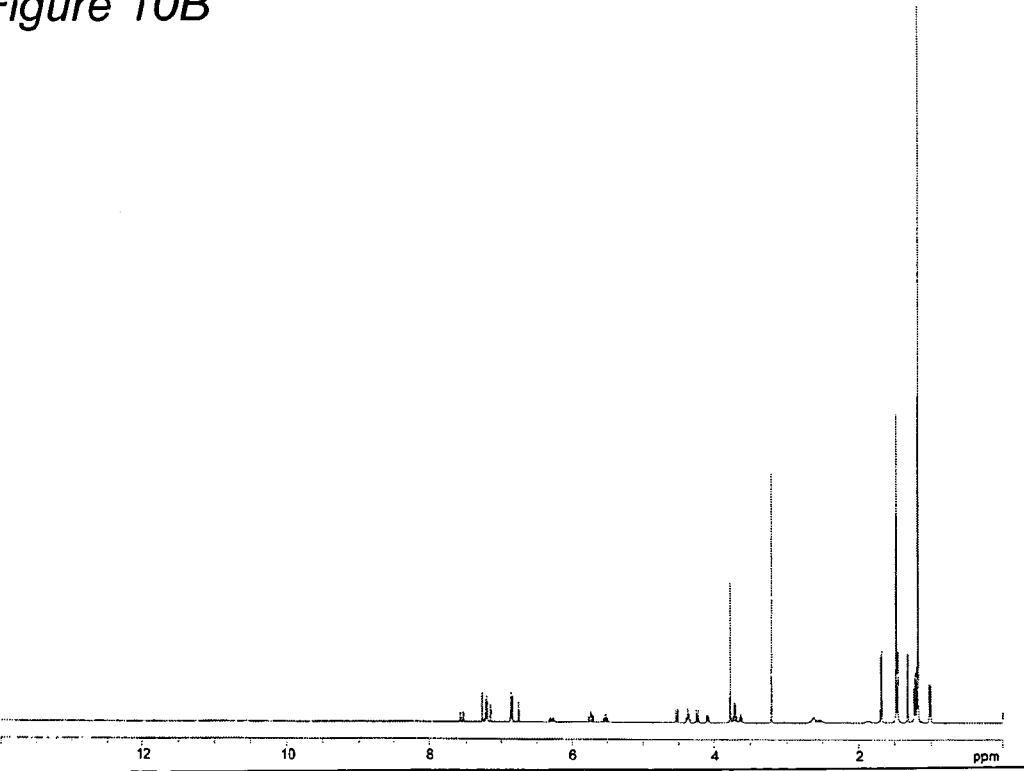
Figure 11A:
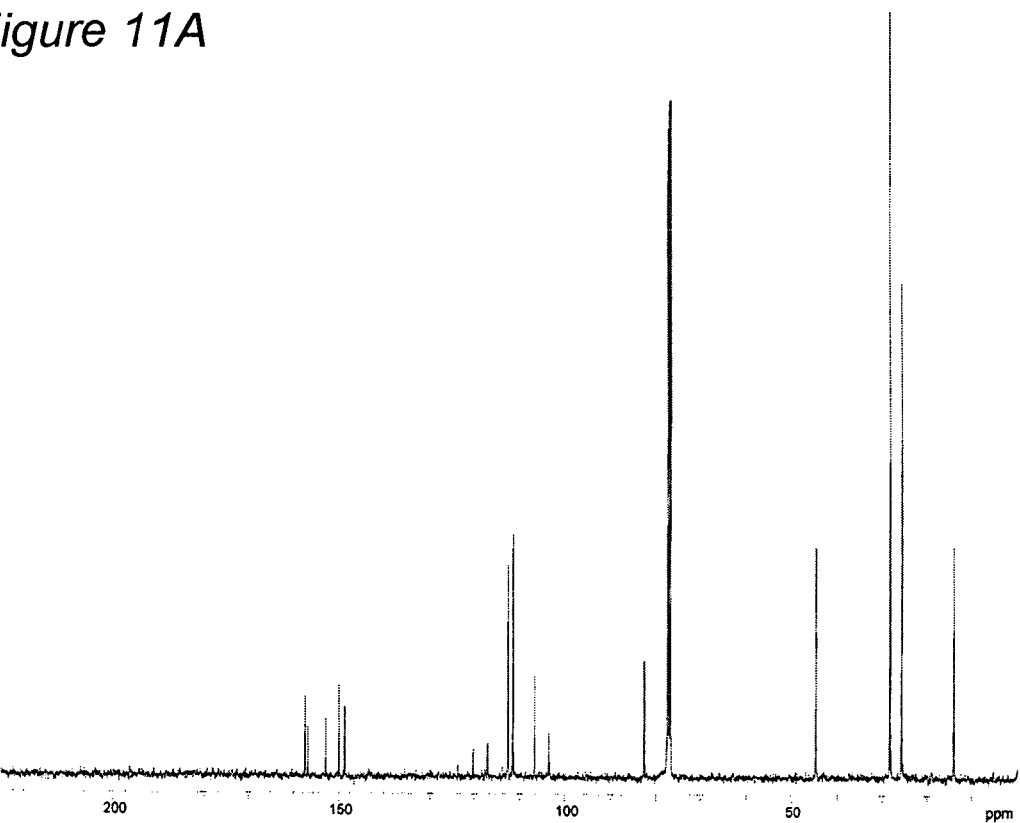
Figure 11B:
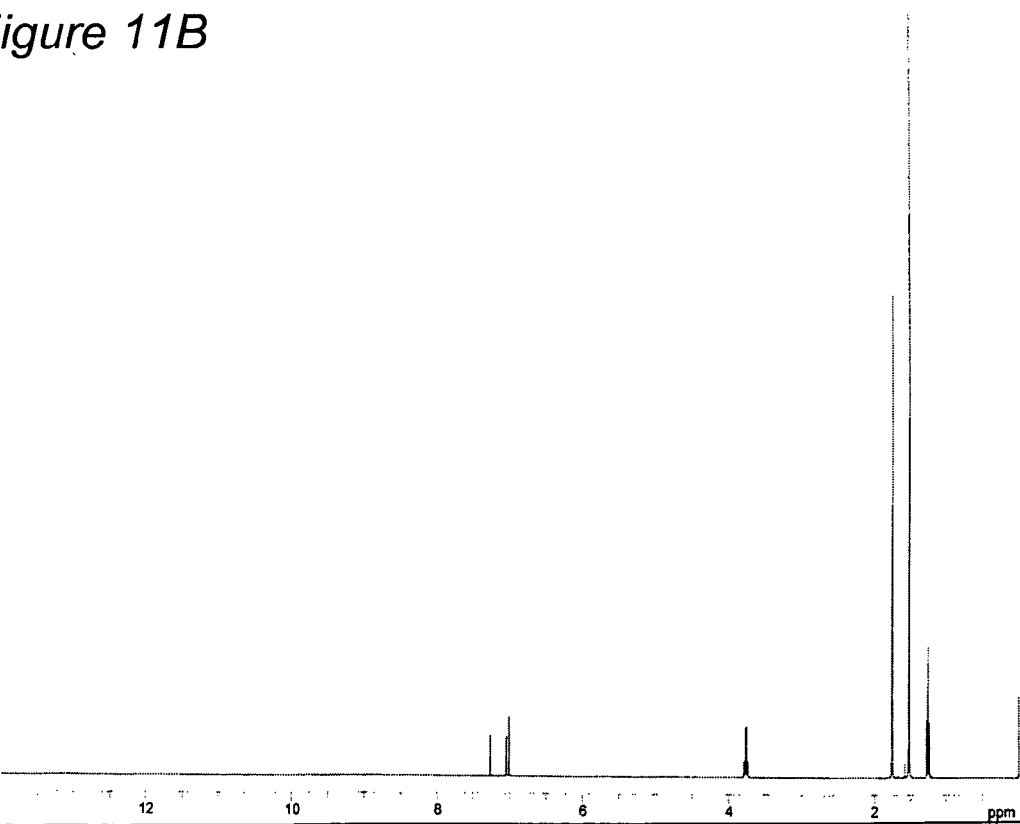

The aryl triflate 011a [1.26 wt.; prepared by treating 007a with LiHDMS and DMPU followed by a quench with Ethyl iodide; $^{13}C$ and $^1H$ NMR depicted in FIGS. 11A and 11B; single crystal X-ray depicted in FIG. 2] and tris(dibenzylidineacetone) dipalladium (0.12 wt.) were combined in a reactor. A solution of the olefin (1.0 wt) in N-methylpyrrolidinone (1.6 wt) was added followed by N-methyldicyclohexylamine (0.53 wt.). The mixture was heated to 80° C. Upon completion, the mixture was cooled to 20° C. A slurry of Celite (0.5 wt.) in MTBE (3.70 wt.) was added. The mixture was filtered and the solids were rinsed 3 times with MTBE (3.70 wt. each). The combined filtrates were washed with 1N aqueous hydrochloric acid (5.1 wt.), twice with 5 wt % aqueous L-cysteine (5 wt.), then 25 wt % aqueous sodium chloride (5.33 wt.). The solvent was concentrate under reduced pressure, providing compound 012. $^{13}C$ and $^1H$ NMR of 012 are depicted in FIGS. 10A and 10B.

The alcohol 012 (1 wt.) was dissolved in THF (23 vol) and added to a cold solution of 20 wt % potassium tert-butoxide in THF (0.88 vol) diluted with THF (19.7 vol.). Upon completion, a solution of tert-butyldimethylsilyl chloride (0.33 wt.) in THF (0.28 vol.) was added. Saturated aqueous sodium bicarbonate (3.5 vol.) was then added, and the solvent was removed under reduced pressure. The residue was dissolved with tert-butyl methyl ether (7 vol.) and the aqueous phase was separated. The organic phase was washed with 25 wt % aqueous sodium chloride (8.4 vol.). The solvent was evaporated under reduced pressure, providing macrocycle 009.

Scheme 17: Compound 010

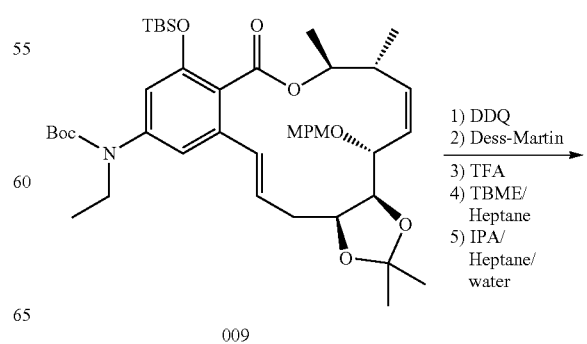

1) DDQ
2) Dess-Martin
3) TFA
4) TBME/ Heptane
5) IPA/ Heptane/ water

009

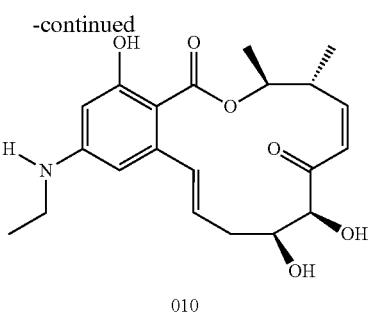

Compound 010 was synthesized from compound 009 as described above in Example 1.

Example 3

Deprotection of 009

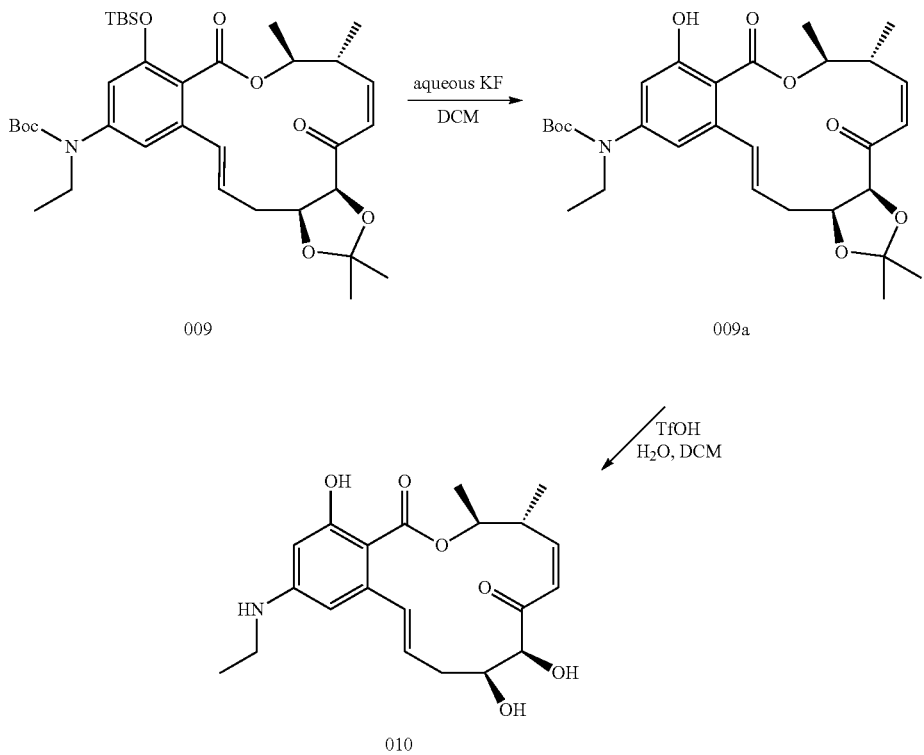

Figure 12A:
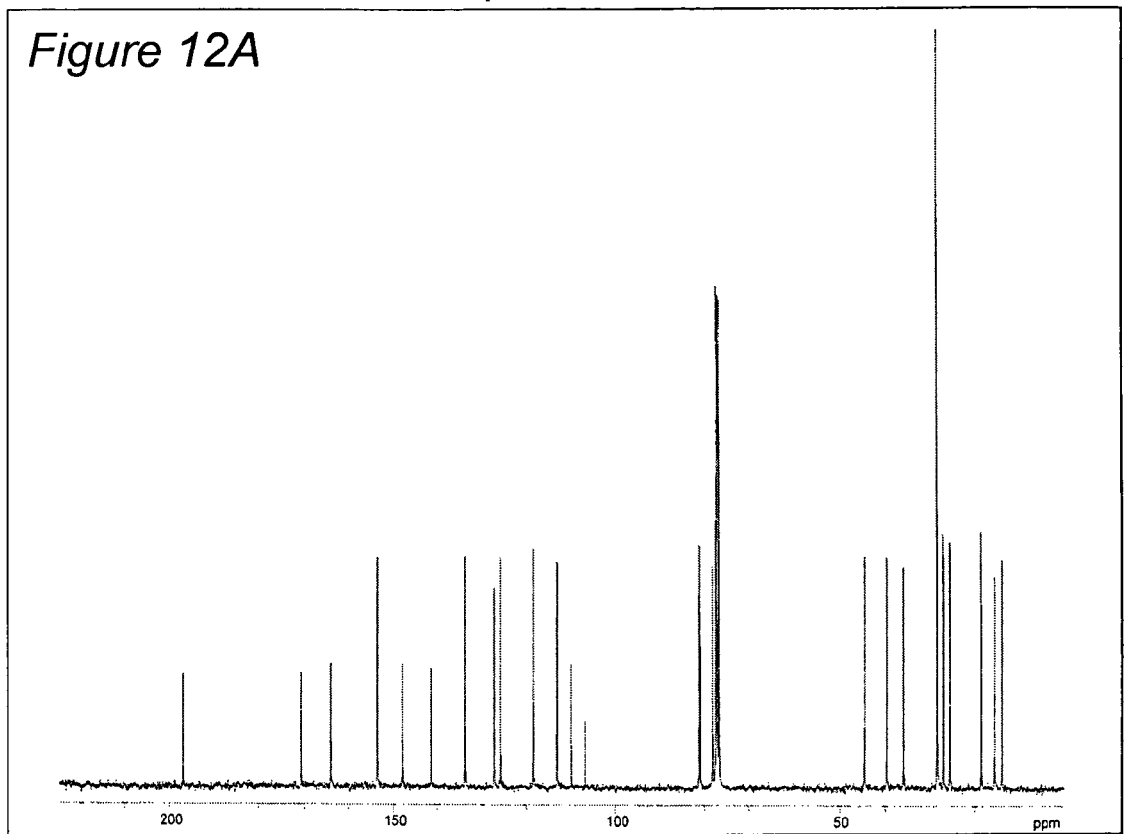
Figure 12B:
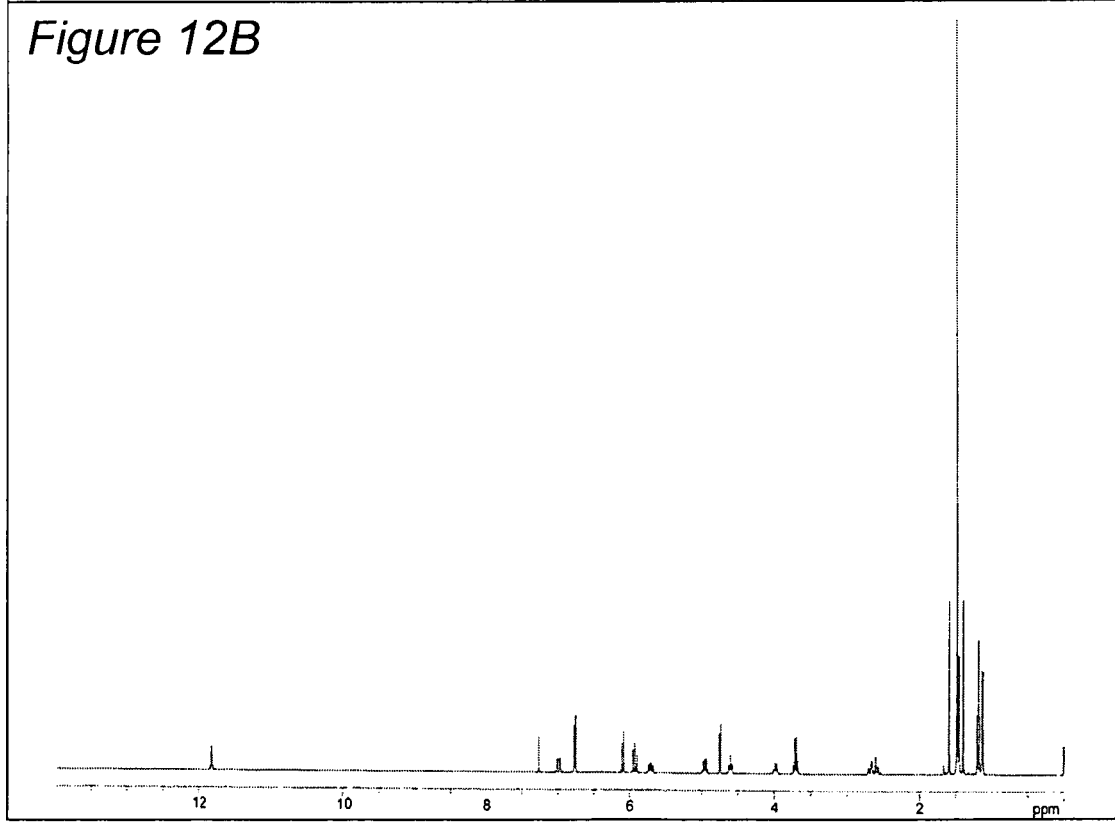

To a solution of enone 009 (1.0 wt) in dichloromethane (2.0 vol) and methanol (2.0 vol) was added potassium fluoride (0.16 wt). Upon completion, water (4.0 wt) and methyl tert-butyl ether (4.0 vol) were added. After separation of the aqueous layer, the organic phase was washed with 25 wt % aqueous sodium chloride, then concentrated under reduced pressure. The crude concentrate was solvent exchanged with 2-propanol (2.0 wt). The crude product 009a was slurried into methanol (5 vol) and heated to 65° C. The solution was cooled to −20° C. The solids (67% yield; M.P. 174-175° C.) were filtered and washed with methanol (5.0 vol) which was pre-chilled to −20° C. [Overall yield from 011 was 29%]. $^{13}$C and $^{1}$H NMR of 009a are depicted in FIGS. 12A and 12B.

To a solution of phenol 009a (1.0 wt) in dichloromethane (8.0 wt) and water (0.2 wt) was added trifluoromethanesulfonic acid (0.51 wt). The reaction mixture was warmed to 30° C. Upon completion, the reaction was quenched with aqueous sodium bicarbonate (5.0 wt), and tert-butyl methyl ether (6.0 wt) was added. The aqueous layer was removed. The organic phase was washed with water (4.0 wt) and 25 wt % aqueous sodium chloride (4.0 wt). The organic phase was polish filtered, then concentrated under reduced pressure. The crude product was solvent exchanged with 2-propanol (2.0 wt) and concentrated to dryness. The crude solid was slurried with 2-propanol (10 vol.). The mixture was heated to 65° C. The solution was then cooled to a temperature of 40° C. and seed crystals were added. The mixture was then cooled to 0° C., and then the solids were filtered. The solids were rinsed with 2-propanol (2.0 vol) pre-chilled to −20° C. The cake was then dried, providing compound 010 in 72.6% yield (M.P. 157-159° C.; Optical rotation +47° at 5 mg/mL in MeOH).

We claim:

1. A crystalline intermediate of formula (VII):

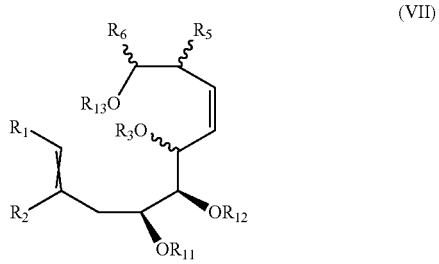

(VII)

wherein R₁ and R₂ are each independently selected from the group consisting of hydrogen, and $C_{1-6}$ alkyl;

R₃ is selected from benzoyl or benzyl, wherein the benzoyl or benzyl are each substituted with 0, 1, 2 or 3 substituents independently selected from —OH, —O($C_{1-4}$ alkyl), —NH₂, —NH($C_{1-4}$-alkyl), —N($C_{1-4}$-alkyl)₂, amides, —OCO($C_{1-4}$-alkyl) and ($C_{1-4}$-alkyl);

R₅ and R₆ are each independently selected from the group consisting of hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, phenyl and benzyl, wherein the phenyl or benzyl are substituted with 0, 1, 2, or 3 substituents independently selected from halogen, hydroxyl, $C_{1-3}$ alkyl, and NH₂; or R₅ and R₆ are taken together with the carbons on which they are attached to form a 5-6 unconjugated membered carbocyclic ring;

R₁₁ and R₁₂ are each independently selected from the group consisting of hydrogen and a base stable oxygen protecting group; or R₁₁ and R₁₂ are taken together to form a 5 membered heterocyclyldiyl of structure (a):

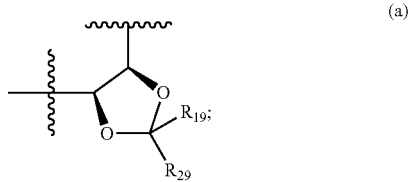

(a)

wherein R₁₉ and R₂₀ are each independently selected from the group consisting of hydrogen, $C_{1-6}$ alkyl, $C_{1-6}$ haloalkyl, $C_{1-6}$ alkoxy and phenyl, or R₁₉ and R₂₀ together represent a fluorenyl moiety of structure (b):

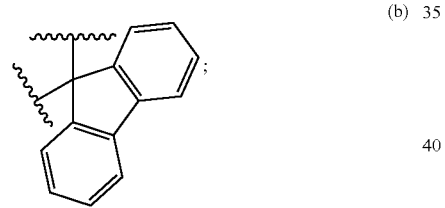

(b)

and R₁₃ is

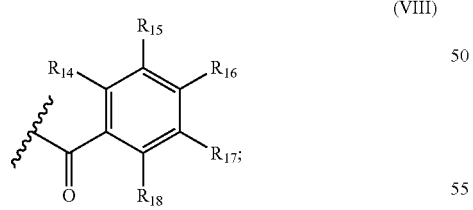

(VIII)

wherein

R₁₄, R₁₅, R₁₆, R₁₇, and R₁₈ are each independently selected from the group consisting of H, NO₂, —NH₃⁺, —COH, —CO($C_{1-4}$ alkyl), —COCl, —COOH, —COO($C_{1-4}$ alkyl), —NR₃⁺, —SO₃H, nitrile, —CF₃ and halogen, wherein at least one of R₁₄, R₁₅, R₁₆, R₁₇, and R₁₈ is selected from the group consisting of NO₂—NH₃⁺, —COH, —CO($C_{1-4}$ alkyl), —COCl, —COOH, —COO($C_{1-4}$ alkyl), —NR₃⁺, —SO₃H, nitrile, —CF₃ and halogen and the other of R₁₄, R₁₅, R₁₆, R₁₇ and R₁₈ are hydrogen.

2. The compound of claim 1, wherein R₁ is hydrogen.

3. The compound of claim 1, wherein R₂ is hydrogen.

4. The compound of claim 1, wherein R₃ is 4-methoxybenzyl.

5. The compound of claim 1, wherein R₅ is selected from the group consisting of hydrogen and $C_{1-6}$ alkyl.

6. The compound of claim 1, wherein R₆ is selected from the group consisting of hydrogen and $C_{1-6}$ alkyl.

7. The compound of claim 1, wherein R₅ is hydrogen or methyl.

8. The compound of claim 1, wherein R₆ is hydrogen or methyl.

9. The compound of claim 1, wherein one of R₁₄, R₁₅, R₁₆, R₁₇, and R₁₈ is selected from the group consisting of NO₂, —NH₃⁺, —COH, —CO($C_{1-4}$ alkyl), —COCl, —COOH, —COO($C_{1-4}$ alkyl), —NR₃⁺, —SO₃H, nitrile, —CF₃ and halogen and the other four of R₁₄, R₁₅, R₁₆, R₁₇, and R₁₈ are hydrogen.

10. The compound of claim 1, wherein R₁₆ is NO₂ and each of R₁₄, R₁₅, R₁₇, and R₁₈ are independently hydrogen.

11. The compound of claim 1, wherein the compound of formula (VII) is a compound of (VIIa):

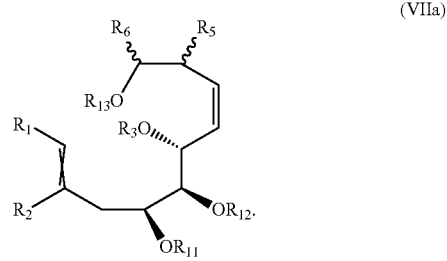

(VIIa)

12. The compound of claim 1, wherein the compound of formula (VII) is a compound of (VIIb):

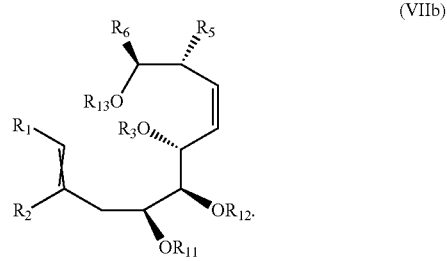

(VIIb)

13. A compound of formula (VIIc):

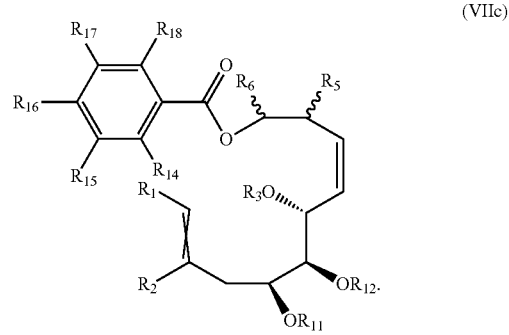

(VIIc)

wherein $R_1$ and $R_2$ are each independently selected from the group consisting of hydrogen and $C_{1-6}$ alkyl;

$R_3$ is selected from benzoyl or benzyl, wherein the benzoyl or benzyl are each substituted with 0, 1, 2 or 3 substituents independently selected from —OH, —O($C_{1-4}$ alkyl), —$NH_2$, —NH($C_{1-4}$alkyl), —N($C_{1-4}$-alkyl)$_2$, amides, —OCO($C_{1-4}$-alkyl) and ($C_{1-4}$alkyl);

$R_5$ and $R_6$ are each independently selected from the group consisting of hydrogen, halogen, $C_{1-6}$ alkyl, $C_{1-6}$ haloalkyl, and $C_{1-6}$ alkoxy;

$R_{11}$ and $R_{12}$ are each independently selected from the group consisting of hydrogen and a base stable oxygen protecting group; or $R_{11}$ and $R_{12}$ are taken together to form a 5 membered heterocyclyldiyl of structure (a):

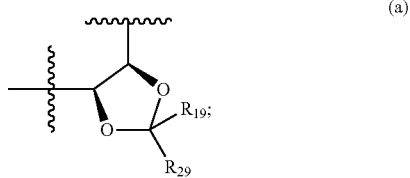

(a)

wherein $R_{19}$ and $R_{20}$ are each independently selected from the group consisting of hydrogen, $C_{1-6}$ alkyl, $C_{1-6}$ haloalkyl and $C_{1-6}$ alkoxy; and at least one of $R_{14}$, $R_{15}$, $R_{16}$, $R_{17}$, and $R_{18}$ is selected from the group consisting of —$NO_2$, —$NH_3^+$, —COH, —CO($C_{1-4}$ alkyl), —COCl, —COOH, —COO($C_{1-4}$ alkyl), —$NR_3^+$, —$SO_3H$, nitrile, —$CF_3$ and halogen and the remainder of $R_{14}$, $R_{15}$, $R_{16}$, $R_{17}$, and $R_{18}$ are each independently H.

14. The compound of claim 13, wherein $R_1$ and $R_2$ are each independently hydrogen.

15. The compound of claim 13, wherein $R_3$ is 4-methoxybenzyl.

16. The compound of claim 13, wherein $R_5$ and $R_6$ are each independently hydrogen or methyl.

17. The compound of claim 13, wherein $R_{16}$ is $NO_2$ and each of $R_{14}$, $R_{15}$, $R_{17}$, and $R_{18}$ are independently hydrogen.

18. The compound of claim 13 having the structure:

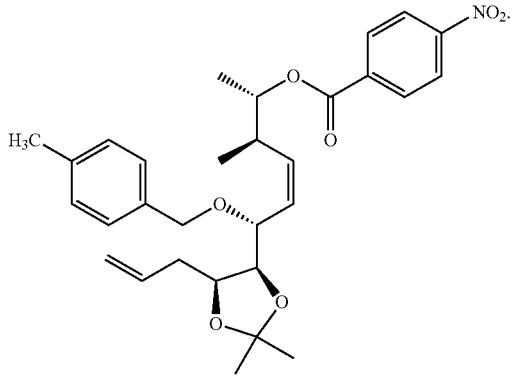 [SMILES: C=CC[C@@H]1OC(C)(C)O[C@@H]1[C@@H](/C=C\[C@@H](C)[C@H](C)OC(=O)c1ccc([N+](=O)[O-])cc1)OCc1ccc(C)cc1]

* * * * *